US010813983B2

(12) United States Patent
Schuch et al.

(10) Patent No.: US 10,813,983 B2
(45) Date of Patent: *Oct. 27, 2020

(54) BACTERIOPHAGE LYSIN AND ANTIBIOTIC COMBINATIONS AGAINST GRAM POSITIVE BACTERIA

(71) Applicant: CONTRAFECT CORPORATION, Yonkers, NY (US)

(72) Inventors: Raymond Schuch, Mountain Lakes, NJ (US); Robert C. Nowinski, New York, NY (US); Michael Wittekind, New Canaan, CT (US); Han Lee, Yonkers, NY (US); Brent Schneider, Glenmoore, PA (US)

(73) Assignee: CONTRAFECT CORPORATION, Yonkers, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/399,575

(22) PCT Filed: May 9, 2013

(86) PCT No.: PCT/US2013/040329
§ 371 (c)(1),
(2) Date: Nov. 7, 2014

(87) PCT Pub. No.: WO2013/170015
PCT Pub. Date: Nov. 14, 2013

(65) Prior Publication Data
US 2015/0290299 A1    Oct. 15, 2015

Related U.S. Application Data

(60) Provisional application No. 61/737,239, filed on Dec. 14, 2012, provisional application No. 61/644,944, filed on May 9, 2012.

(51) Int. Cl.
*A61K 38/46* (2006.01)
*C12N 9/50* (2006.01)
(Continued)

(52) U.S. Cl.
CPC .......... *A61K 38/46* (2013.01); *A61K 31/4188* (2013.01); *A61K 31/5377* (2013.01);
(Continued)

(58) Field of Classification Search
CPC .... A61K 2300/00; A61K 38/47; A61K 38/12; A61K 38/14; A61K 9/0019; A61K 45/06; A61K 38/16; A61K 38/05; A61K 38/08; A61K 38/10; A61K 41/0009; A61K 41/0057; A61K 41/0071; A61K 47/10; A61K 47/26; A61K 47/34; A61K 47/64; A61K 47/6911; A61K 8/64; A61K 9/0063; A61K 9/06; A61K 38/162; A61K 38/50; A61K 47/02; A61K 47/183; A61K 38/46; A61K 9/0043; A61K 9/0048;
A61K 31/4188; A61K 31/5377; A61K 38/164; A01N 37/46; A01N 25/10; A01N 35/06; A01N 43/24; A01N 43/42; A01N 43/90; A01N 63/00; A01N 63/02; C12Y 302/01017; C12Y 305/01028; C12Y 304/24075; A61Q 11/00; C07K 14/001; C07K 5/06104; C07K 5/1021; C07K 5/126; C07K 7/06; C07K 7/08; C07K 7/64; C07K 14/315; C07K 2319/01; C07K 2319/55; C07K 16/1271; C07K 2317/24; C07K 14/195; C07K 2317/76; C07K 2319/00; C07K 2319/70; C07K 16/00; C07K 16/08; C07K 16/12; C07K 16/1275; C07K 16/1278; C07K 2317/569; C07K 2318/20; C07K 2319/035; C07K 2319/30; G01N 33/569; G01N 33/56911; Y02A 50/47; Y02A 50/473; Y02A 50/481; C12N 9/503; C12N 9/2462; C12N 9/52; C12N 9/80; C12N 15/1037; C12N 15/52; C12N 15/85;
(Continued)

(56) References Cited

U.S. PATENT DOCUMENTS

| | | | |
|---|---|---|---|
| 5,604,109 A | 2/1997 | Fischetti et al. | |
| 5,912,226 A | 6/1999 | Baker et al. | |

(Continued)

FOREIGN PATENT DOCUMENTS

| | | | |
|---|---|---|---|
| CA | 2833409 A1 | 4/2012 | |
| WO | WO08018854 | 2/2008 | |

(Continued)

OTHER PUBLICATIONS

Schmitz, J.E., Expanding the Horizons of Enzybiotic Identification (2011), Student Theses and Dissertations, paper 138.*
Accession B9WWF8 Apr. 14, 2009.
Abad, CL et al (2011) Antimicrobial therapy of sepsis and septic shock—when are two drugs better than one? Crit Care Clinic 27(2):e1-27.
Aksoy, DY et al (2008) New antimicrobial agents for the treatment of Gram-positive bacterial infections Clin Microbiol Infect 14(5):411-420.

(Continued)

*Primary Examiner* — Deborah K Ware
(74) *Attorney, Agent, or Firm* — MH2 Technology Law Group, LLP

(57) ABSTRACT

The present invention provides compositions and methods for prevention, amelioration and treatment of gram positive bacteria, particularly *Staphylococcal* bacteria, with combinations of lysin, particularly Streptococcal lysin, particularly the lysin PlySs2, and one or more antibiotic, including daptomycin, vancomycin, oxacillin, linezolid, or related antibiotic(s).

8 Claims, 36 Drawing Sheets
Specification includes a Sequence Listing.

(51) Int. Cl.

| | | |
|---|---|---|
| *A61K 31/4188* | (2006.01) | |
| *A61K 31/5377* | (2006.01) | |
| *A61K 38/12* | (2006.01) | |
| *A61K 38/47* | (2006.01) | |
| *A61K 45/06* | (2006.01) | |
| *A61K 38/14* | (2006.01) | |

(52) U.S. Cl.
CPC .............. *A61K 38/12* (2013.01); *A61K 38/14* (2013.01); *A61K 38/47* (2013.01); *A61K 45/06* (2013.01); *C12N 9/503* (2013.01); *C12Y 302/01017* (2013.01)

(58) Field of Classification Search
CPC ......... A61L 2300/404; A61L 2300/406; A61L 2420/00; A61L 29/08; A61L 29/16; A61P 31/04; A61P 43/00; C12Q 1/18; C12Q 1/34; C40B 40/02; C40B 40/10
See application file for complete search history.

(56) References Cited

U.S. PATENT DOCUMENTS

| | | |
|---|---|---|
| 5,985,271 A | 11/1999 | Fischetti et al. |
| 6,017,528 A | 1/2000 | Fischetti et al. |
| 6,056,955 A | 5/2000 | Fischetti et al. |
| 6,248,324 B1 | 6/2001 | Fischetti et al. |
| 6,254,866 B1 | 7/2001 | Fischetti et al. |
| 6,264,945 B1 | 7/2001 | Fischetti et al. |
| 6,444,813 B2 | 9/2002 | Bergren |
| 7,402,309 B2 | 7/2008 | Fischetti et al. |
| 7,569,223 B2 | 8/2009 | Fischetti et al. |
| 7,582,291 B2 | 9/2009 | Yoong et al. |
| 7,638,600 B2 | 12/2009 | Fischetti et al. |
| 9,034,322 B2 * | 5/2015 | Fischetti ............... A61K 38/162 424/94.61 |
| 2006/0292135 A1 | 12/2006 | Loomis et al. |
| 2007/0254321 A1 | 11/2007 | Fischetti et al. |
| 2008/0221035 A1 | 9/2008 | Fischetti |
| 2009/0053149 A1 | 2/2009 | Corcoran et al. |
| 2010/0172918 A1 | 7/2010 | Yoon et al. |
| 2013/0302306 A1 | 11/2013 | Schuch et al. |
| 2014/0072549 A1 | 3/2014 | Fischetti et al. |
| 2014/0179594 A1 | 6/2014 | Fischetti et al. |

FOREIGN PATENT DOCUMENTS

| | | |
|---|---|---|
| WO | 2010002959 A2 | 1/2010 |
| WO | WO10002959 | 1/2010 |
| WO | 2011091412 | 7/2011 |
| WO | 2012145573 A2 | 10/2012 |
| WO | WO121456930 | 10/2012 |
| WO | WO2012145630 A2 | 10/2012 |
| WO | 2012146738 A1 | 11/2012 |
| WO | 2013170022 A1 | 11/2013 |

OTHER PUBLICATIONS

Baltz, RH (2009) Daptomycin: mechanisms of action and resistance, and biosynthetic engineering Curr Opin Chem Biol 13(2):144-151.
Beres, SB et al (2007) Contribution of exogenous genetic elements to the group A *Streptococcus* metagenome PLOS One 2(8):1-14.
Berti, AD et al (2012) Altering the proclivity towards daptomycin resistance in methicillin-resistant *Staphylococcus aureus* using combinations with other antibiotics Antimicrob Agents Chemother 56(10):5046-5053.
Blaser, M (2011) Antibiotic overuse: Stop the killing of beneficial bacteria Nature 476(7361):393-394.
Brink, AJ (2012) Does resistance in severe infections caused by methicillin-resistant *Staphylococcus aureus* give you the 'creeps'? Curr Opin Crit Care 18(5):451-459.
Chica, RA et al (2005) Semi-rational approaches to engineering enzyme activity: combining the benefits of directed evolution and rational design Curr Opin Biotechnol 16(4):378-384.
Cottarel, G et al (2007) Combination drugs, an emerging option for antibacterial therapy Trends Biotechnol 25 (12):547-555.
Crandon, JL et al (2010) Comparative efficacies of human simulated exposures of telavancin and vancomycin against methicillin-resistant *Staphylococcus aureus* with a range of vancomycin MICs in a murine pneumonia model Antimicrob Agents Chemother 54(12):5115-5119.
Daniel, A et al (2010) Synergism between a novel chimeric lysin and oxacillin protects against infection by methicillin-resistant *Staphylococcus aureus* Antimicrob Agents Chemother 54(4):1603-1612.
Dhand, A et al (2011) Use of antistaphylococcal beta-lactams to increase daptomycin activity in eradicating persistent bacteremia due to methicillin-resistant *Staphylococcus aureus*: role of enhanced daptomycin binding Clin infect Dis 53 (2):158-163.
Entenza, JM et al (2005) Therapeutic effects of bacteriophage Cpl-1 lysin against *Streptococcus pneumoniae* endocarditis in rats Antimicrob Agents Chemother 49(11):4789-4792.
Fenton, M et al (2010) Recombinant bacteriophage lysins as antibacterials Bioeng Bugs 1(1):9-16.
Fischbach, MA (2011) Combination therapies for combating antimicrobial resistance Curr Opin Microb 14(5):519-523.
Fischetti, VA et al (2006) Reinventing phage therapy: are the parts greater than the sum? Nat Biotechnol 24 (12):1508-1511.
Fischetti, VA (2008) Bacteriophage lysins as effective antibacterials Curr Opin Microb 11(5):393-400.
Ford, CW et al (1996) In vivo activities of U-100592 and U-100766, novel oxazolidinone antimicrobial agents, against experimental bacterial infections Antimicrob Agents Chemoth 40(6):1508-1513.
Friedman, L et al (2006) Genetic changes that correlate with reduced susceptibility to daptomycin in *Staphylococcus aureus* Antimicrob Agents Chemother 50(6):2137-2145.
Garcia, E et al (1988) Molecular evolution of lytic enzymes of *Streptococcus pneumoniae* and its bacteriophages Proc Natl Acad Sci USA 85(3):914-918.
Garcia, P et al (1990) Modular organization of the lytic enzymes of *Streptococcus pneumoniae* and its bacteriophages Gene 86(1):81-88.
Gill, SR et al (2005) Insights on evolution of virulence and resistance from the complete genome analysis of an early methicillin-resistant *Staphylococcus aureus* strain and a biofilm-producing methicillin-resistant *Staphylococcus epidermidis* strain J Bacteriol 187(7):2426-2438.
Gilmer, DB et al (2013) Novel Bacteriophage Lysin with Broad Lytic Activity Protects against mixed Infection by *Streptococcus pyogenes* and Methicillin-Resistant *Staphylococcus aureus* Antimicrob Agents Chemother 57 (6):2743-2750.
Grandgirard, D et al (2008) Phage lytic enzyme Cpl-1 for antibacterial therapy in experimental pneumococcal meningitis J infect Dis 197(11):1519-1522.
LaPlante, KL et al (2008) Activities of clindamycin, daptomycin, doxycycline, linezolid, trimethoprim-sulfamethoxazole, and vancomycin against community-associated methicillin-resistant *Staphylococcus aureus* with inducible clindamycin resistance in murine thigh infection and in vitro pharmacodynamic models Antimicrob Agents Chemother 52 (6):2156-2162.
Loeffler, JM et al (2001) Rapid killing of *Streptococcus pneumoniae* with a bacteriophage cell wall hydrolase Science 294(5549):2170-2172.
Loeffler, JM et al (2003) Phage Lytic Enzyme Cpl-1 as a Novel Antimicrobial for Pneumococcal Bacteremia Infect Immun 71(11):6199-6204.
Loessner, MJ et al (1995) Heterogeneous endolysins in Listeria monocytogenes bacteriophages: a new class of enzymes and evidence for conserved holin genes within the siphoviral lysis cassettes Mol Microbiol 16(6):1231-1241.
López, R et al (1992) Structural analysis and biological significance of the cell wall lytic enzymes of *Streptococcus pneumoniae* and its bacteriophage FEMS Microbiol Lett 100:439-448.

(56) References Cited

OTHER PUBLICATIONS

López, R et al (1997) The pneumococcal cell wall degrading enzymes: a modular design to create new lysins? Microb Drug Resist 3(2):199-211.
Manoharadas, S et al (2009) Antimicrobial activity of a chimeric enzybiotic towards *Staphylococcus aureus* Journal of biotechnology 139(1):118-123.
Massey, RC et al (2006) The evolution and maintenance of virulence in *Staphylococcus aureus*: a role for host-to-host transmission? Nat Rev Microbiol 4(12):953-958.
McCullers, JA et al (2007) Novel strategy to prevent otitis media caused by colonizing *Streptococcus pneumoniae* PLOS pathogens 3(3):e28-0001-0003.
Miao, V et al (2005) Daptomycin biosynthesis in Streptomyces roseosporus: cloning and analysis of the gene cluster and revision of peptide stereochemistry Microbiology 151(Pt5):1507-1523.
Moise, PA et al (2009) Susceptibility relationship between vancomycin and daptomycin in *Staphylococcus aureus*: facts and assumptions Lancet Infect Dis 9(10):617-624.
Mueller, M et al (2004) Issues in Pharmacokinetics and Pharmacodynamics of Anti-Infective Agents: Kill Curves versus MIC Antimicrob Agents Chemother 48(2):369-377.
Nelson, D et al (2001) Prevention and elimination of upper respiratory colonization of mice by group A streptococci by using a bacteriophage lytic enzyme Proc Natl Acad Sci USA 98(7):4107-4112.
Palmer, KL et al (2011) Genetic basis for daptomycin resistance in enterococci Antimicrob Agents Chemother 55 (7):3345-3356.
Pastagia, M et al (2011) A novel chimeric lysin shows superiority to mupirocin for skin decolonization of methicillin-resistant and -sensitive *Staphylococcus aureus* strains Antimicrob Agents Chemother 55(2):738-744.
Pereira, PM et al (2007) Fluorescence ratio imaging microscopy shows decreased access of vancomycin to cell wall synthetic sites in vancomycin-resistant *Staphylococcus aureus* Antimicrob Agents Chemother 51(10):3627-3633.
Fischetti VA (2010) Bacteriophage endolysins: a novel anti-infective to control Gram-positive pathogens Int J Med Microbiol 300(6):357-362.
Rashel, M et al (2007) Efficient elimination of multidrug-resistant *Staphylococcus aureus* by cloned lysin derived from bacteriophage phi MR11 J Infect Dis 196(8):1237-1247.
Romero, A et al (1990) Sequence of the *Streptococcus pneumoniae* bacteriophage HB-3 amidase reveals high homology with the major host autolysin J Bacteriol 172(9):5064-5070.
Ronda, C et al (1987) Biological role of the pneumococcal amidase. Cloning of the lytA gene in *Streptococcus pneumonia* Eur J Biochem 164(3):621-624.
Sánchez-Puelles, JM et al (1987) 3'-end modifications of the *Streptococcus pneumoniae* lytA gene: role of the carboxy terminus of the pneumococcal autolysin in the process of enzymatic activation (conversion) Gene 61(1):13-19.
Schweizer, ML et al (2011) Comparative effectiveness of nafcillin or cefazolin versus vancomycin in methicillin-susceptible *Staphylococcus aureus* bacteremia BMC Infect Dis 11:279.
Sen, S et al (2007) Developments in directed evolution for improving enzyme functions Appl Biochem Biotechnol 143 (3):212-223.
Silverman, JA et al (2005) Inhibition of daptomycin by pulmonary surfactant: in vitro modeling and clinical impact J Infect Dis 191(12):2149-2152.
Sopirala, MM et al (2010) Synergy testing by Etest, microdilution checkerboard, and time-kill methods for pan-drug-resistant Acinetobacter baumannii Antimicrob Agents Chemother 54(11):4678-4683.
Steenbergen, JN et al (2005) Daptomycin: a lipopeptide antibiotic for the treatment of serious Gram-positive infections J Antimicrob Chemother 55(3):283-288.
Swaney, SM et al (1998) The oxazolidinone linezolid inhibits initiation of protein synthesis in bacteria Antimicrob Agents Chemoth 42(12):3251-3255.

Tallarida, RJ (2012) Revisiting the isobole and related quantitative methods for assessing drug synergism J Pharmacology Exp Ther 342(1):2-8.
Wang, IN et al (2000) HOLINS: The Protein Clocks of Bacteriophage Infections Annu Rev Microbil 54:799-825.
Willing, BP et al (2011) Shifting the balance:antibiotic effects on host-microbiota mutualism Nat Rev Microbiol 9 (4):233-243.
Witzenrath, M et al (2009) Systemic use of the endolysin Cpl-1 rescues mice with fatal pneumococcal pneumonia Crit Care Med 37(2):642-649.
Bateman A et al (2003) The CHAP domain: a large family of amidases including GSP amidase and peptidoglycan hydrolases Trends Biochem Sci 28(5)234-237.
Ponting CP et al (1999) Eukaryotic signalling domain homologues in archaea and bacteria. Ancient ancestry and horizontal gene transfer J Mol Biol. 289(4):729-745.
Whisstock JC et al (1999) SH3 domains in prokaryotes Trends Biochem Sci 24(4):132-133.
Zou Y et al (2010) Systematic analysis of an amidase domain CHAP in 12 *Staphylococcus aureus* genomes and 44 staphylococcal phage genomes Comput Biol Chem. 34(4):251-257.
Kohanski MA, et al—Sub-lethal antibiotic treatment leads to multidrug resistance via radical-induced mutagenesis; Mol Cell 2010; 37(3): 311-320.
Notice of Reasons for Rejection issued in corresponding Japanese Patent Application No. 2015-511698 dated May 23, 2019, pp. 1-17 (with English translation).
Preliminary Rejection issued in corresponding Korean Patent Application No. 10-2014-7034614 dated Jun. 28, 2019, pp. 1-9 (with English translation).
Non-Final Rejection issued in U.S. Appl. No. 15/848,886 dated Jun. 27, 2019.
Singh et al., "Protein Engineering Approaches in the Post-Genomic Era", Current Protein and Peptide Science, vol. 18 (2017) pp. 1-11.
Canadian Office Action issued in corresponding Canadian Patent Application No. 2,872,902 dated Apr. 1, 2019, pp. 1-6.
Russian Office Action issued in corresponding Russian Patent Application No. 2014149351 dated May 16, 2017, pp. 1-17 (including English language translation).
Russian Office Action issued in corresponding Russian Patent Application No. 2014149351 dated Nov. 14, 2017, pp. 1-18 (including English language translation).
Australian Office Action issued in corresponding Australian Patent Application No. 2013259427 dated Feb. 3, 2017, pp. 1-5.
New Zealand Office Action issued in corresponding New Zealand Patent Application No. 702105 dated Dec. 9, 2015, pp. 1-6.
New Zealand Office Action issued in corresponding New Zealand Patent Application No. 702105 dated Aug. 1, 2016, pp. 1-5.
Mexican Office Action issued in corresponding MX/a/2014/013586 dated Feb. 22, 2018, pp. 1-12.
Mexican Office Action issued in corresponding MX/a/2014/013586 dated Oct. 4, 2018, pp. 1-8.
Mexican Office Action issued in corresponding MX/a/2014/013586 dated May 24, 2019, pp. 1-4.
Mexican Office Action issued in corresponding MX/a/2014/013586 dated Nov. 26, 2019, pp. 1-4.
Australian Office Action issued in corresponding Australian Patent Application No. 2018202845 dated Feb. 11, 2020, pp. 1-6.
Djurkovic et al., Synergistic Killing of *Streptococcus pneumoniae* with the Bacteriophage Lytic Enzyme Cpl-1 and Penicillin or Gentamicin Depends on the Level of Penicillin Resistance, 2005, Antimicrobial Agents and Chemotherapy, 49:1225-1228.
Pillai et al., Development of Reduced Vancomycin Susceptibility in Methicillin-Susceptible *Staphylococcus aureus*, 2009, Clinical Infectious Diseases, 49:1169-1174.
Rossi et al., Structural elucidation of the Cys-His-Glu-Asn proteolytic relay in the secreted CHAP domain enzyme from the human pathogen *Staphylococcus saprophyticus*, 2009, Proteins: Structure, Function, and Bioinformatics, 74: 515-519.
Document M07-A9, Methods for dilution antimicrobial susceptibility tests for bacteria that grow aerobically, 2012, (Wayne (PA): Clinical and Laboratory Standards Institute (US), 32:1-88.

(56) References Cited

OTHER PUBLICATIONS

Loessner et al., Modified Listeria bacteriophage lysin genes (ply) allow efficient overexpression and one-step purification of biochemically active fusion proteins, 1996, Applied and Environmental Microbiology, 62:3057-3060.
Garcia et al., Cloning, purification, and biochemical characterization of the pneumococcal bacteriophage Cp-1 lysin, 1987, Virology, 61:2573-2580.
Alignment including SEQ ID No. 3 of US 20140072549.
Karlin et al., Applications and statistics for multiple high-scoring segments in molecular sequences, 1993, Proceedings of the National Academy of Sciences (PNAS), 90:5873-5877.
Altschul et al., Gapped BLAST and PSI-BLAST: a new generation of protein database search programs, 1997, Nucleic Acids Research, 25:3389-3402.
Recsei et al., Cloning, sequence, and expression of the lysostaphin gene from *Staphylococcus simulans*, 1987, Proceedings of the National Academy of Sciences, 84:1127-1131.
Caldentey et al., The lytic enzyme of the Pseudomonas phage θ6, purification and biochemical characterization, 1992, Biochimica et Biophysica Acta, 1159:44-50.
Klevens et al., Invasive Methicillin-Resistant *Staphylococcus aureus* Infections in the United States, 2007, Journal of the American Medical Association (JAMA), 298:1763-1771.
Ben-David et al., Are there differences in hospital cost between patients with nosocomial methicillin-resistant *Staphylococcus aureus* bloodstream infection and those with methicillin-susceptible *S. aureus* bloodstream infection?, 2009, Infection Control and Hospital Epidemiology, 30:453-460.
Schuch et al. (2009). A Genetic Screen to Identify Bacteriophage Lysins. Methods in molecular biology (Clifton, N.J.). 502. 307-19. 10.1007/978-1-60327-565-1_18.
Donlan et al., Biofilms: Survival mechanisms of clinically relevant microorganisms, Clinical Microbiology Reviews, 2002,15:167-193.
Costerton et al., Bacterial biofilms: a common cause of persistent infections, Science, 1999, 284:1318-1322.
Kiedrowski et al., New approaches for treating staphylococcal biofilm infections, 2011, Annals of the New York Academy of Sciences, 1241:104-121.
Domenech et al., In vitro destruction of *Streptococcus pneumoniae* biofilms with bacterial and phage peptidoglycan hydrolases, 2011, Antimicrobial Agents and Chemotherapy, 2011, 55:4144-4148.
Meng et al., Application of a Bacteriophage Lysin to Disrupt Biofilms Formed by the Animal Pathogen *Streptococcus suis*, 2011, Applied and Environmental Microbiology, 77:8272-8279.
Schuch et al., A bacteriolytic agent that detects and kills Bacillus anthracis, 2002, Nature, 418:884-889.
Kokai-Kun et al., Lysostaphin as a treatment for systemic *Staphylococcus aureus* infection in a mouse model, 2007, Journal of Antimicrobial Chemotherapy, 60:1051-1059.
Matias et al., Cryo-electron microscopy of cell division in *Staphylococcus aureus* reveals a mid-zone between nascent aross walls, 2007, Molecular Microbiology, 64:195-206.
Kashyap et al., Peptidoglycan recognition proteins kill bacteria by activating protein-sensing two-component systems, Nature Medicine, 2011, 17:676-683.
Jobson et al., Retrospective observational study comparing vancomycin versus daptomycin as initial therapy for *Staphylococcus aureus* infections, 2011, Clinical Therapeutics, 33:1391-1399.
Mang, Y., I-TASSER server for protein 3D structure prediction, 2008, BMC Bioinformatics, 9:40, pp. 1-8.
Pettersen et al., UCSF Chimera—a visualization system for exploratory research and analysis, 2004, Journal of Computational Chemistry, 25:1605-612.
Schmitz, J., Expanding the Horizons of Enzybiotic Identification, Graduate School Student Theses, The Rockefeller University, Jun. 2011, [Retrieved from internet on Jan. 19, 2017] URL: http://hdl.handle.net/10209/448.
Australian Office Action issued in corresponding Australian Patent Application No. 2018202845 dated Jun. 3, 2019, pp. 1-4.
Brazilian Office Action issued in corresponding Brazilian Patent Application No. BR112014027842-3 dated Aug. 1, 2019, pp. 1-5 (including English language translation).
Chinese Office Action issued in corresponding Chinese Patent Application No. 201380036510.8 dated Jan. 22, 2016, pp. 1-18 (including English language translation).
Chinese Office Action issued in corresponding Chinese Patent Application No. 201380036510.8 dated Oct. 18, 2016, pp. 1-17 (including English language translation).
Chinese Office Action issued in corresponding Chinese Patent Application No. 201380036510.8 dated Jul. 3, 2017, pp. 1-33 (including English language translation).
Chinese Office Action issued in corresponding Chinese Patent Application No. 201380036510.8 dated Jan. 19, 2018, pp. 1-10 (including English language translation).
Chinese Office Action issued in corresponding Chinese Patent Application No. 201380036510.8 dated Sep. 27, 2018, pp. 1-15 (including English language translation).
Gilmer et al., Novel Bacteriophage Lysin with Broad Lytic Activity Protects against Mixed Infection by Methicillin-Resistant *Staphylococcus aureus* and *Streptococcus pyogenes*, 2013, Antimicrob. Agents Chemother., 57 (6):2743-2750, Epub Apr. 9, 2013.
Vouillamoz et al., Bactericidal synergism between daptomycin and the phage lysin cpl-1 in a mouse model of pneumococcal bacteremia, 2013, International Journal of Antimicrobial Agents, 42:416-421.
Supplementary European Search Report issued in corresponding European Patent Application No. 13787128.1 dated Dec. 9, 2015, pp. 1-3.
European Office Action issued in corresponding European Patent Application No. 13787128.1 dated Jan. 19, 2018, pp. 1-5.
European Office Action issued in corresponding European Patent Application No. 13787128.1 dated Dec. 6, 2018, pp. 1-4.
Extended European Search Report issued corresponding European Patent Application No. 13787128.1 dated Dec. 18, 2015, pp. 1-5.
International Preliminary Report on Patentability issued in corresponding International Application No. PCT/US2013/040329 dated Nov. 11, 2014, pp. 1-12.
International Search Report issued in corresponding International Application No. PCT/US2013/040329 dated Oct. 9, 2013, one page.
Israeli Office Action issued in corresponding Israeli Patent Application No. 235527 dated Sep. 17, 2018, pp. 1-5 (including partial English translation).
Israeli Office Action issued in corresponding Israeli Patent Application No. 235527 dated Jul. 3, 2017, pp. 1-6 (including partial English translation).
Indian Office Action issued in corresponding Indian Patent Application No. 2437/MUMNP/2014 dated Jun. 21, 2018, pp. 1-7.
Japanese Office Action issued in corresponding Japanese Patent Application No. 2015-511698 dated Feb. 2, 2017, pp. 1-17 (including English language translation).
Japanese Office Action issued in corresponding Japanese Patent Application No. 2015-511698 dated May 22, 2019, pp. 1-17 (including English language translation).
Japanese Office Action issued in corresponding Japanese Patent Application No. 2015-511698 dated Dec. 7, 2017, pp. 1-22 (including English language translation).
Korean Office Action issued in corresponding Korean Patent Application No. 10-2014-7034614 dated Jun. 28, 2019, pp. 1-18 (including English language translation).
Korean Office Action issued in corresponding Korean Patent Application No. 10-2014-7034614 dated Jan. 30, 2020, pp. 1-7 (including English language translation).
Israel Office Action issued in Israel Patent Application No. 235527 dated Jun. 8, 2020 and partial English language translation (7 pages).
Extended European Search Report issued in European Patent Application No. 20 158 873.8 dated Jun. 5, 2020 (9 pages).
Canadian Office Action issued in corresponding Canadian Patent Application No. 2872902 dated Jul. 21, 2020 (8 pages).

\* cited by examiner

FIGURE 5
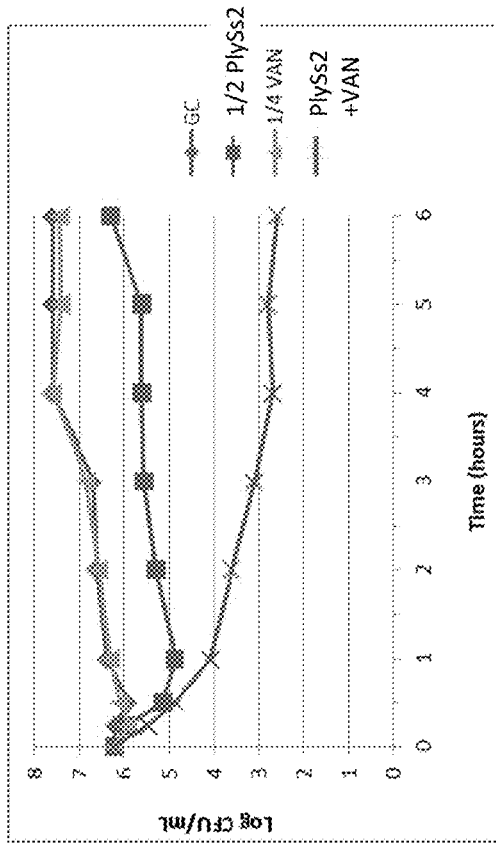
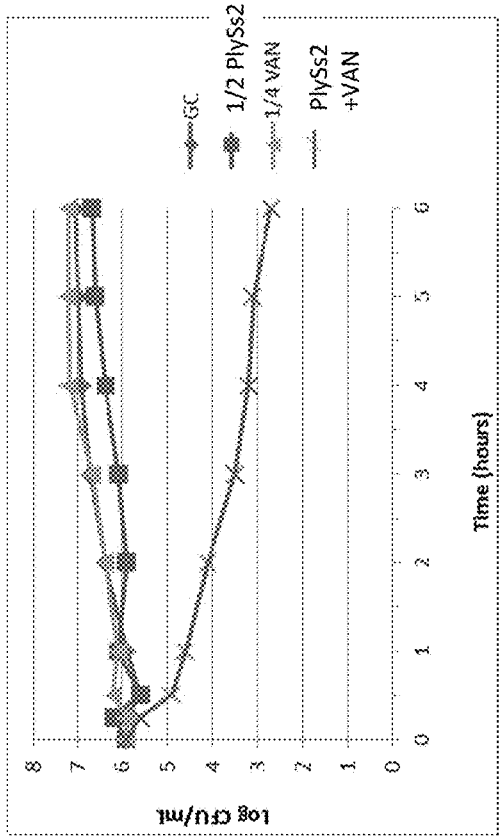

FIGURE 6
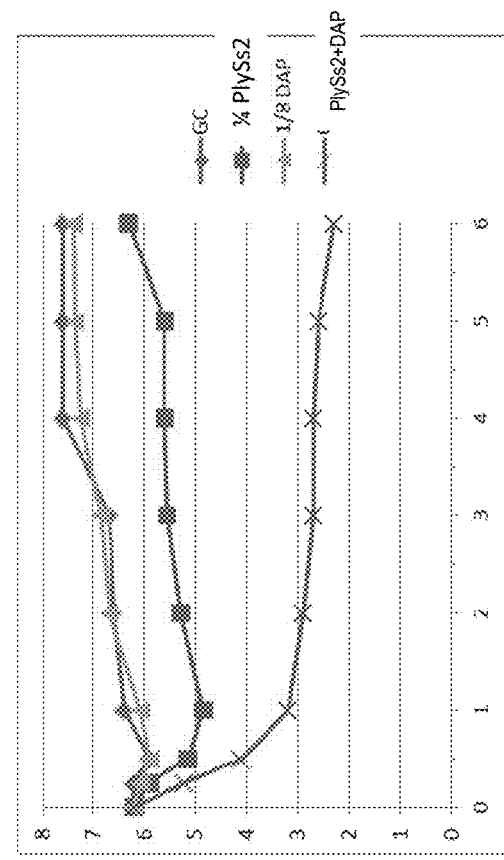
MRSA strain 269:
¼ MIC PlySs2
1/8 MIC daptomycin
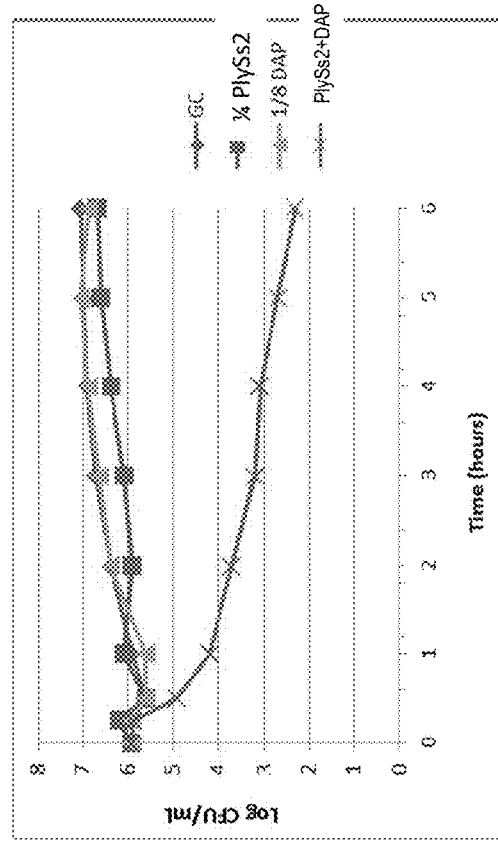
MRSA strain 553:
¼ MIC PlySs2
1/8 MIC daptomycin PlySs2 and Oxacillin Against MSSA Strain JMI 7140

PlySs2 and Oxacillin Against Methicillin-Susceptible *Staphylococcus aureus*

PlySs2 and Daptomycin Against MRSA Strain JMI 3345

FIGURE 13
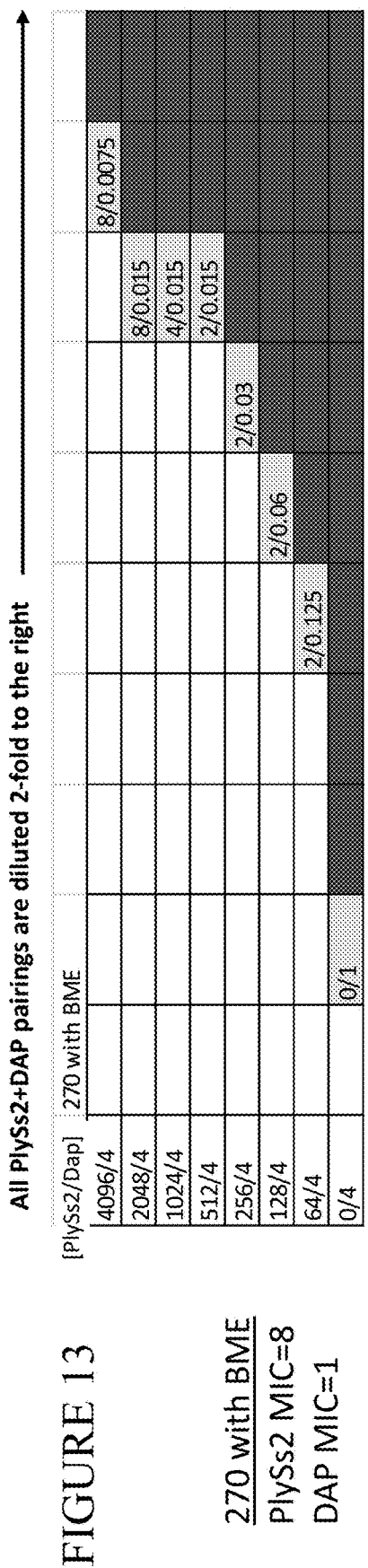
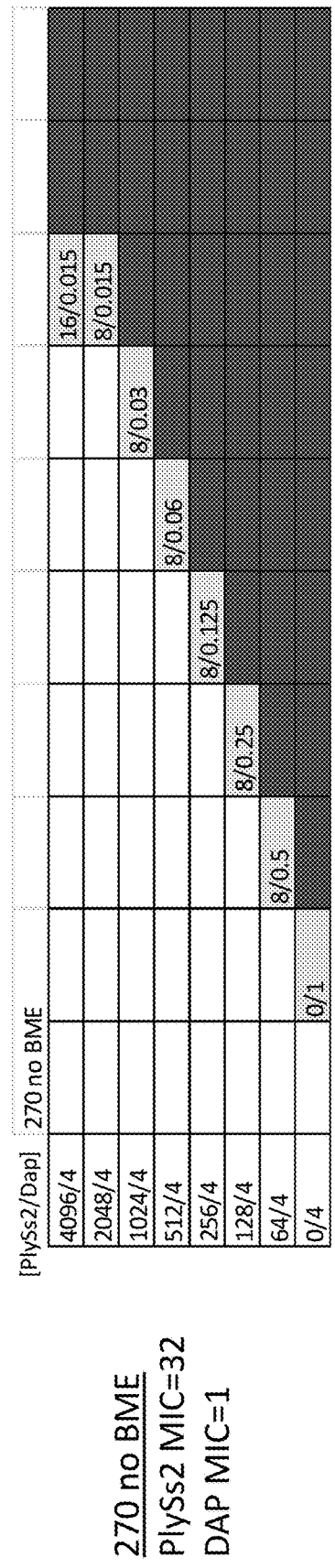
270 with BME
PlySs2 MIC=8
DAP MIC=1
- PlySs2 synergy dose is 2 (1/4 MIC)
- At PlySs2 2, DAP is effective to 0.015 (64X improvement)
270 no BME
PlySs2 MIC=32
DAP MIC=1
- PlySs2 synergy dose is 8 (1/4 MIC)
- At PlySs2 8, DAP is effective to 0.015 (64X improvement)

FIGURE 16
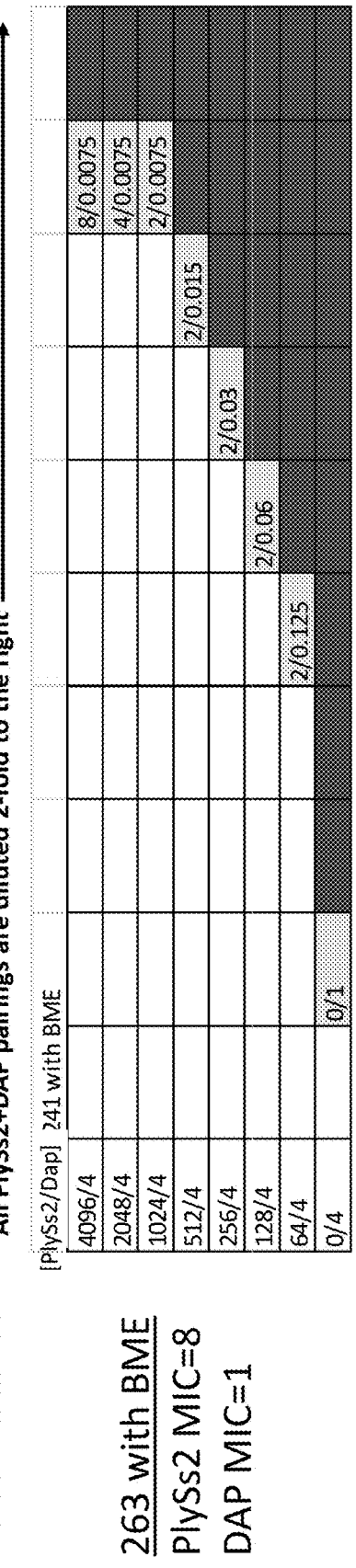
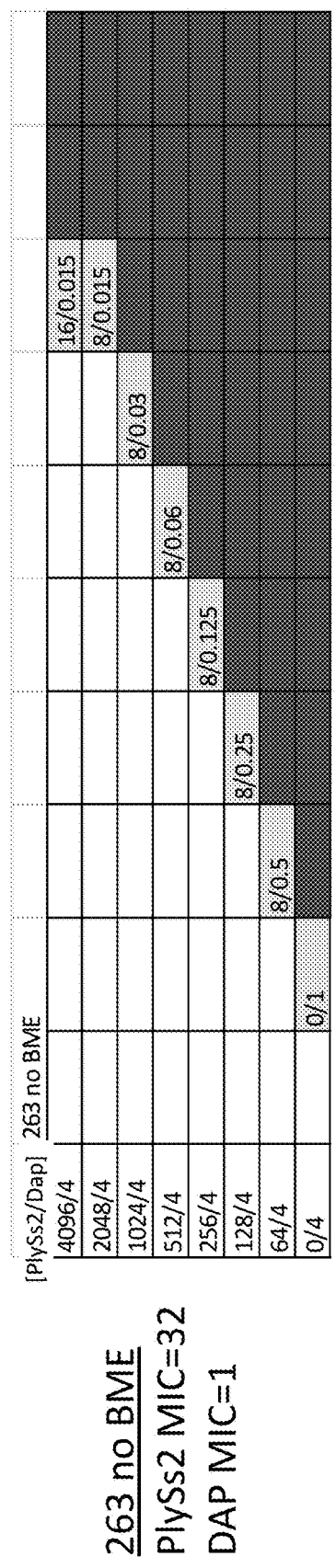
263 with BME
PlySs2 MIC=8
DAP MIC=1
- PlySs2 synergy dose is 2 (1/4 MIC)
- At PlySs2 2, DAP is effective to 0.0075 (128X improvement)
263 no BME
PlySs2 MIC=32
DAP MIC=1
- PlySs2 synergy dose is 8 (1/4 MIC)
- At PlySs2 8, DAP is effective to 0.015 (64X improvement)

FIGURE 17

All PlySs2+DAP pairings are diluted 2-fold to the right →

650 with BME

| [PlySs2]/[Dap] | 650 with BME | | | | | | | | |
|---|---|---|---|---|---|---|---|---|---|
| 4096/4 | | | | | | | | | 8/0.0075 |
| 2048/4 | | | | | | | | 8/0.015 | |
| 1024/4 | | | | | | | | 4/0.015 | |
| 512/4 | | | | | | | 4/0.03 | | |
| 256/4 | | | | | | 4/0.06 | | | |
| 128/4 | | | | | 4/0.125 | | | | |
| 64/4 | | | | 4/0.25 | | | | | |
| 0/4 | 0/1 | | | | | | | | |

650 with BME
PlySs2 MIC=8
DAP MIC=1

- PlySs2 synergy dose is 4 (1/2 MIC)
- At PlySs2 4, DAP is effective to 0.015 (64X improvement)

650 no BME

| [PlySs2]/[Dap] | 650 no BME | | | | | | | | |
|---|---|---|---|---|---|---|---|---|---|
| 4096/4 | | | | | | | | | 32/0.015 |
| 2048/4 | | | | | | | | 32/0.03 | |
| 1024/4 | | | | | | | 32/0.06 | | |
| 512/4 | | | | | | 32/0.125 | | | |
| 256/4 | | | | | 32/0.5 | | | | |
| 128/4 | 32/1 | | | | | | | | |
| 64/4 | 16/1 | | | | | | | | |
| 0/4 | 0/1 | | | | | | | | |

650 no BME
PlySs2 MIC=64
DAP MIC=1

- PlySs2 synergy dose is 32 (1/2 MIC)
- At PlySs2 32, DAP is effective to <0.015 (>32X improvement)

FIGURE 19
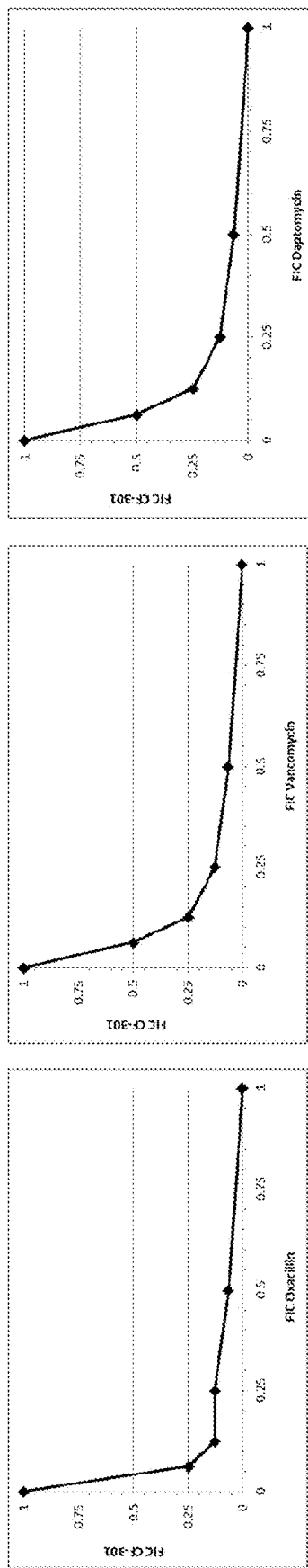
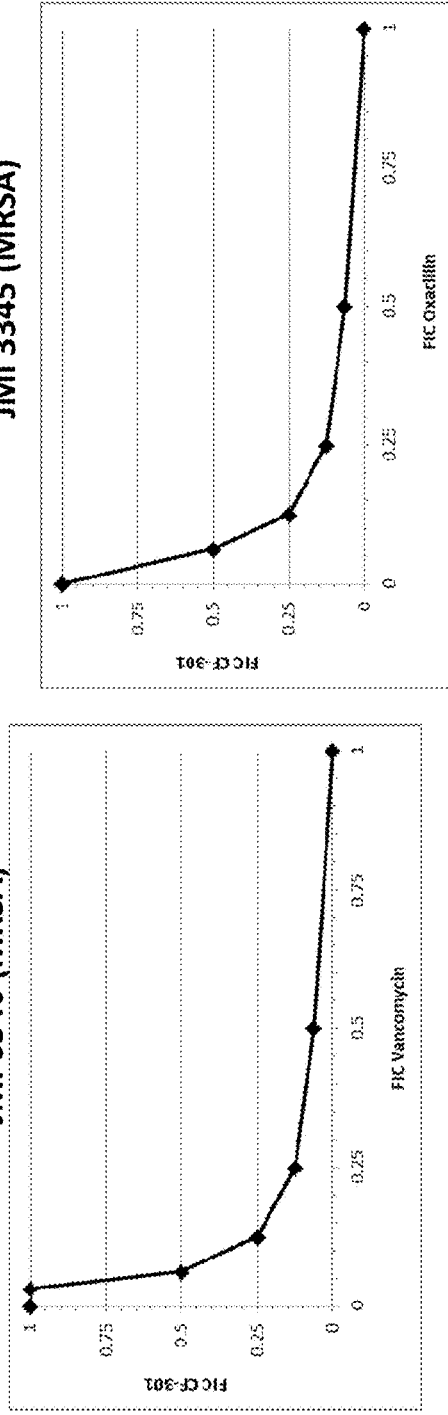

FIGURE 21
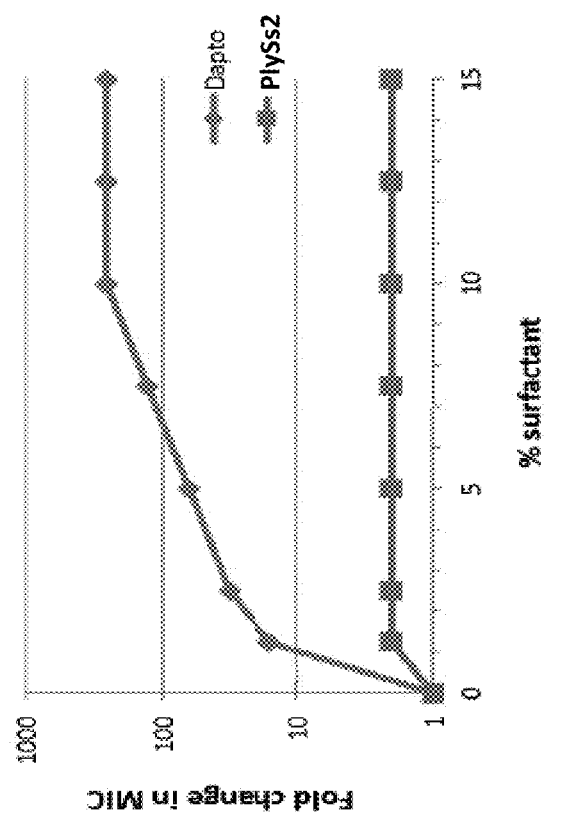
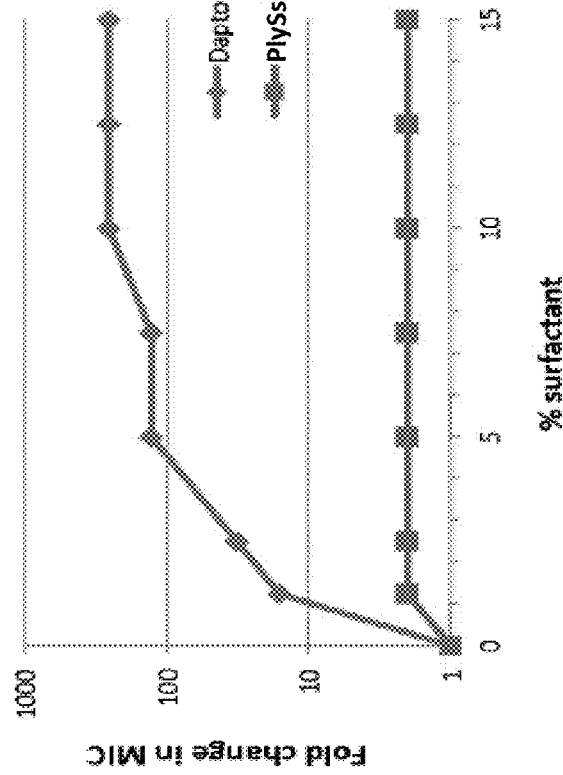

FIGURE 29

MTTVNEALNN VRAQVGSGVS VGNGECYALA SMYERMISPD ATVGLGAGVG WVSGAIGDTI SAKNIGSSYN
WQANGWTVST SGPFKAGQIV TLGATPGNPY GHVVIVEAVD GDRLTILEQN YGGKRYPVRN YYSAASYRQQ
VVHYITPPGT VAQSAPNLAG SRSYRETGTM TVTVDALNVR RAPNTSGEIV AVYKRGESFD YDTVIIDVNG
YVWVSYIGGS GKRNYVATGA TKDGKRFGNA WGTFK

CHAP Domain in green LNNVR...VVHYIT
SH3-5 Domain in red RSYRE...GKRNYVAT

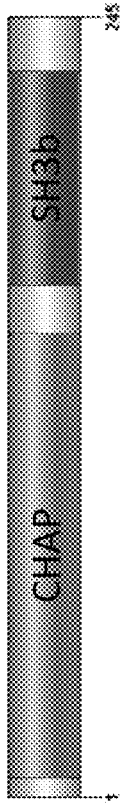

ATGACAACAG TAAATGAAGC ATTAAATAAT GTAAGAGCTC AGGTTGGGTC CGGTGTGTCT GTTGGCAACG
GCGAATGCTA CGCTTTGGCT AGTTGGTACG AGCGCATGAT TAGTCCGGAT GCAACTGTCG GACTTGGCGC
TGGTGTGGGC TGGGTCAGCG GTGCAATACG CGATACAATC TCTGCCAAAA ACATCGGCTC ATCATACAAC
TGGCAAGCTA ACGGCTGGAC AGTTTCCACA AGTTTCCCAT TTAAAGCAGG TCAGATTGTG ACGCTTGGGG
CAACACCAGG AAACCCTTAC GGACATGTGG TAATCGTCGA AGCAGTGGAC GGCGATAGAT TGACTATTTT
GGAGCAAAAC TACGGCGGGA AACGTTATCC CGTCCGTAAT CGTCAAGCTA TCGTCAACAG
GTCGTGCATT ACATCACACC GCCTGGCACG ACTGTCTCT CAATGTTCGC AGGGGCCAA ATACTTCAGG
ATCGCGAGAC GGGCACTATG GCAGTATACA AGCGTGGTGA TATGATACTG TCATCATCGA TGTCAATGCT
CGAGATTGTA GCAGTATACA AGCGTGGTGA TATGATACTG TCATCATCGA TGTCAATGCT
TATGTCTGGG TGTCTTACAT AGGCGGCAGC ATCATTTGAC ACTACGTTGC GACGGGCGCT ACCAAAGACG
GTAAGCCGTT CGGCAATGCT TGGGGTACAT TTAAATAA

BACTERIOPHAGE LYSIN AND ANTIBIOTIC COMBINATIONS AGAINST GRAM POSITIVE BACTERIA

CROSS REFERENCE TO RELATED APPLICATIONS

The present application is a § 371 of PCT Application No. PCT/US2013/040329 filed May 9, 2013, which in turn, claims priority from U.S. Provisional Application Ser. No. 61/644,944 filed May 9, 2012 and U.S. Provisional Application Ser. No. 61/737,239 filed Dec. 14, 2012, the entire disclosures of the applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Sep. 3, 2020, is named 0341.0007_ST25.txt and is 8,031 bytes in size.

FIELD OF THE INVENTION

The present invention relates generally to prevention, amelioration and treatment of gram positive bacteria, including Staphylococcal bacteria, with combinations of lysin, particularly Streptococcal lysin, particularly the lysin PlySs2, and one or more antibiotic.

BACKGROUND OF THE INVENTION

The development of drug resistant bacteria is a major problem in medicine as more antibiotics are used for a wide variety of illnesses and other conditions. The use of more antibiotics and the number of bacteria showing resistance has prompted longer treatment times. Furthermore, broad, non-specific antibiotics, some of which have detrimental effects on the patient, are now being used more frequently. A related problem with this increased use is that many antibiotics do not penetrate mucus linings easily.

Gram-positive bacteria are surrounded by a cell wall containing polypeptides and polysaccharide. Gram-positive bacteria include but are not limited to the genera *Actinomyces, Bacillus, Listeria, Lactococcus, Staphylococcus, Streptococcus, Enterococcus, Mycobacterium, Corynebacterium,* and *Clostridium*. Medically relevant species include *Streptococcus pyogenes, Streptococcus pneumoniae, Staphylococcus aureus,* and *Enterococcus faecalis. Bacillus* species, which are spore-forming, cause anthrax and gastroenteritis. Spore-forming *Clostridium* species are responsible for botulism, tetanus, gas gangrene and pseudomembranous colitis. *Corynebacterium* species cause diphtheria, and *Listeria* species cause meningitis.

Novel antimicrobial therapy approaches include enzyme-based antibiotics ("enzybiotics") such as bacteriophage lysins. Phages use these lysins to digest the cell wall of their bacterial hosts, releasing viral progeny through hypotonic lysis. A similar outcome results when purified, recombinant lysins are added externally to Gram-positive bacteria. The high lethal activity of lysins against gram-positive pathogens makes them attractive candidates for development as therapeutics (Fischetti, V. A. (2008) Curr Opinion Microbiol 11:393-400; Nelson, D. L. et al (2001) Proc Natl Acad Sci USA 98:4107-4112). Bacteriophage lysins were initially proposed for eradicating the nasopharyngeal carriage of pathogenic streptococci (Loeffler, J. M. et al (2001) Science 294: 2170-2172; Nelson, D. et al (2001) Proc Natl Acad Sci USA 98:4107-4112). Lysins are part of the lytic mechanism used by double stranded DNA (dsDNA) phage to coordinate host lysis with completion of viral assembly (Wang, I. N. et al (2000) Annu Rev Microbiol 54:799-825). Lysins are peptidoglycan hydrolases that break bonds in the bacterial wall, rapidly hydrolyzing covalent bonds essential for peptidoglycan integrity, causing bacterial lysis and concomitant progeny phage release.

Lysin family members exhibit a modular design in which a catalytic domain is fused to a specificity or binding domain (Lopez, R. et al (1997) Microb Drug Resist 3:199-211). Lysins can be cloned from viral prophage sequences within bacterial genomes and used for treatment (Beres, S. B. et al (2007) PLoS ONE 2(8):1-14). When added externally, lysins are able to access the bonds of a Gram-positive cell wall (Fischetti, V. A. (2008) Curr Opinion Microbiol 11:393-400). Bacteriophage lytic enzymes have been established as useful in the assessment and specific treatment of various types of infection in subjects through various routes of administration. For example, U.S. Pat. No. 5,604,109 (Fischetti et al.) relates to the rapid detection of Group A streptococci in clinical specimens, through the enzymatic digestion by a semi-purified Group C streptococcal phage associated lysin enzyme. This enzyme work became the basis of additional research, leading to methods of treating diseases. Fischetti and Loomis patents (U.S. Pat. Nos. 5,985,271, 6,017,528 and 6,056,955) disclose the use of a lysin enzyme produced by group C streptococcal bacteria infected with a C1 bacteriophage. U.S. Pat. No. 6,248,324 (Fischetti and Loomis) discloses a composition for dermatological infections by the use of a lytic enzyme in a carrier suitable for topical application to dermal tissues. U.S. Pat. No. 6,254,866 (Fischetti and Loomis) discloses a method for treatment of bacterial infections of the digestive tract which comprises administering a lytic enzyme specific for the infecting bacteria. The carrier for delivering at least one lytic enzyme to the digestive tract is selected from the group consisting of suppository enemas, syrups, or enteric coated pills. U.S. Pat. No. 6,264,945 (Fischetti and Loomis) discloses a method and composition for the treatment of bacterial infections by the parenteral introduction (intramuscularly, subcutaneously, or intravenously) of at least one lytic enzyme produced by a bacteria infected with a bacteriophage specific for that bacteria and an appropriate carrier for delivering the lytic enzyme into a patient.

Phage associated lytic enzymes have been identified and cloned from various bacteriophages, each shown to be effective in killing specific bacterial strains. U.S. Pat. Nos. 7,402,309, 7,638,600 and published PCT Application WO2008/018854 provides distinct phage-associated lytic enzymes useful as antibacterial agents for treatment or reduction of *Bacillus anthraces* infections. U.S. Pat. No. 7,569,223 describes lytic enzymes for *Streptococcus pneumoniae*. Lysin useful for *Enterococcus (E. faecalis* and *E. faecium*, including vancomycin resistant strains) are described in U.S. Pat. No. 7,582,291. U.S. 2008/0221035 describes mutant Ply GBS lysins highly effective in killing Group B streptococci. A chimeric lysin denoted ClyS, with activity against Staphylococci bacteria, including *Staphylococcus aureus*, is detailed in WO 2010/002959.

Based on their rapid, potent, and specific cell wall-degradation and bactericidal properties, lysins have been suggested as antimicrobial therapeutics to combat Gram-positive pathogens by attacking the exposed peptidoglycan cell walls from outside the cell (Fenton, M et al (2010)

Bioengineered Bugs 1:9-16; Nelson, D et al (2001) Proc Natl Acad Sci USA 98:4107-4112). Efficacies of various lysins as a single agents have been demonstrated in rodent models of pharyngitis (Nelson, D et al (2001) Proc Natl Acad Sci USA 98:4107-4112), pneumonia (Witzenrath, M et al (2009) Crit Care Med 37:642-649), otitis media (McCullers, J. A. et al (2007) PLOS pathogens 3:0001-0003), abscesses (Pastagia, M et al Antimicrobial agents and chemotherapy 55:738-744) bacteremia (Loeffler, J. M. et al (2003) Infection and Immunity 71:6199-6204), endocarditis (Entenza, J. M. et al (2005) Antimicrobial agents and chemotherapy 49:4789-4792), and meningitis (Grandgirard, D et al (2008) J Infect Dis 197:1519-1522). In addition, lysins are generally specific for their bacterial host species and do not lyse non-target organisms, including human commensal bacteria which may be beneficial to gastrointestinal homeostasis (Blaser, M. (2011) Nature 476:393-394; Willing, B. P. et al (2011) Nature reviews. Microbiology 9:233-243)

Antibiotics in clinical practice include several which commonly affect cell wall peptidoglycan biosynthesis in gram positive bacteria. These include glycopeptides, which as a class inhibit peptidoglycan synthesis by preventing the incorporation of N-acetylmuramic acid (NAM) and N-acetylglucosamine (NAG) peptide subunits into the peptidoglycan matrix. Available glycopeptides include vancomycin and teicoplanin, with vancomycin a primary drug of choice and clinical application in bacteremia, particularly Staphylococcal infections. Penicillins act by inhibiting the formation of peptidoglycan cross-links. Common penicillins include oxacillin, ampicillin and cloxacillin. Linezolid (Zyvox) is a protein synthesis inhibitor and in a class of antibacterials called oxazolidinones (Ford C W et al (1996) Antimicrob Agents Chemoth 40(6):1508-1513; Swaney S M et al (1998) Antimicrob Agents Chemoth 42(12):3251-3255; U.S. Pat. No. 6,444,813).

Daptomycin (Cubicin), also denoted LY 146032, is a lipopeptide antibacterial agent consisting of a 13-member amino acid peptide linked to a 10-carbon lipophilic tail (Miao V et al (2005) Microbiology 151(Pt5):1507-1523; Steenbergen J N et al (2005) J Antimicrob Chemother 55(3):283-288; and described in U.S. Pat. No. 5,912,226). This structure results in a novel mechanism of action, the disruption of the bacterial membrane through the formation of transmembrane channels, which cause leakage of intracellular ions leading to depolarizing the cellular membrane and inhibition of macromolecular synthesis. Daptomycin's spectrum of activity is limited to Gram-positive organisms, including a number of highly resistant species (methicillin-resistant *S. aureus* (MRSA), vancomycin intermediate-sensitive *S. aureus* (VISA), vancomycin-resistant *S. aureus* (VRSA), vancomycin-resistant *Enterococcus* (VRE)). In studies it appears to be more rapidly bactericidal than vancomycin. Its approved dosing regimen is 4 mg/kg IV once daily. Dose adjustment is necessary in renal dysfunction. Daptomycin's primary toxicity is reversible dose-related myalgias and weakness. Daptomycin has been approved for the treatment of complicated skin and soft tissue infections caused by gram positive bacteria, *Staphylococcus aureus* bacteremia and right-sided *S. aureus* endocarditis. Trials assessing daptomycin's efficacy in treating complicated urinary tract infections and endocarditis/bacteremia are ongoing. Its approved dosing regimen is 4 mg/kg IV once daily. Dose adjustment is necessary in renal dysfunction. Daptomycin's primary toxicity is reversible dose-related myalgias and weakness. Resistance to daptomycin has been encountered both in vitro and in vivo after exposure to daptomycin. The mechanism(s) of resistance are not fully defined but likely relate to alterations of the cellular membrane. Multiple passages of Staphylococci and Enterococci in subinhibitory drug concentrations resulted in MIC increases in a stepwise fashion. Daptomycin binds avidly to pulmonary surfactant and cannot be effectively used in treatment of pneumonia (Baltz R H (2009) Curr Opin Chem Biol 13(2):144-151).

The broad spectrum antibiotics in clinical use for treatment of gram positive infections, particularly including critical care antibiotics such as vancomycin, are limited in use and application by their side effects of gastrointestinal upset and diarrhea and the development of resistance, particularly in connection with continued or long-term use.

It is evident from the deficiencies and problems associated with current traditional antibacterial agents that there still exists a need in the art for additional specific bacterial agents, combinations and therapeutic modalities, particularly without high risks of acquired resistance. Accordingly, there is a commercial need for new antibacterial approaches, especially those that operate via new modalities or provide new combinations to effectively kill pathogenic bacteria.

The citation of references herein shall not be construed as an admission that such is prior art to the present invention.

SUMMARY OF THE INVENTION

The present application relates to combinations of bacteriophage lysin(s) with antibiotic for rapid and effective killing of gram positive bacteria. In accordance with the invention, the lysin PlySs2, which demonstrates broad killing activity against multiple bacteria, particularly gram-positive bacteria, including *Staphylococcus* and *Streptococcus* bacterial strains, provides remarkable synergy in combination with antibiotic(s) and can significantly reduce the effective MIC doses required for antibiotic(s).

The lysin may be combined with broad spectrum gram positive antibiotic(s), including one or more of vancomycin, daptomycin, linezolid or oxacillin, including related or similar antibiotics. In a particular aspect, PlySs2 lysin is combined with daptomycin to provide synergistic killing activity against gram-positive bacteria, including Staphylococci, particularly including MRSA. In a particular aspect, PlySs2 lysin is combined with vancomycin to provide synergistic killing activity against Streptococci, including MRSA. In a particular aspect, PlySs2 lysin is combined with linezolid to provide synergistic killing activity against Streptococci, including MRSA. In an aspect of the invention, combination with PlySs2 lysin significantly reduces the dose of antibiotic required to kill a gram positive bacteria, such as *S. aureus*.

In accordance with the invention, combinations of PlySs2 lysin and antibiotic, including antibiotic of distinct type or class, particularly including daptomycin, vancomycin, linezolid or oxacillin are effective to kill gram positive bacteria, including *S. aureus*, at lower doses or with lower MIC than either alone. In an aspect of the invention, lower dose formulations of lysin and of antibiotic, including suitable for administration in combination or separately simultaneously or in series, are provided wherein the dose for effective killing or decolonization of a gram positive infection are lower than the dose required if either are provided alone. In particular, low dose formulations of antibiotic are provided for administration in combination with lysin, particularly PlySs2 lysin, administered simultaneously or in series, wherein the dose for effective killing or decolonization of a gram positive infection of the antibiotic are lower in combination with the lysin than the dose required if antibiotic is provided or administered alone.

In an aspect of the invention, lysins effective against Staphylococci are combined with one or more of daptomycin, vancomycin, linezolid or oxacillin, or related antibiotic compounds, to kill gram positive bacteria, including *S. aureus*, at lower doses or with lower MIC than either alone. In an aspect of the invention, lysins effective against Staphylococci are combined with daptomycin, or related antibiotic compounds, to kill gram positive bacteria, including *S. aureus*, at lower doses or with lower MIC than either alone. In an aspect of the invention, lysins effective against Staphylococci are combined with one or more of vancomycin, or related antibiotic compounds, to kill gram positive bacteria, including *S. aureus*, at lower doses or with lower MIC than either alone. In a particular aspect the antibiotic is combined with PlySs2 lysin or a variant thereof. In an aspect of the invention, the combination of lysin with daptomycin circumvents the effect of surfactant to reduce daptomycin activity. In combination with lysin, such as PlySs2 lysin, daptomycin is rendered effective in killing *S. aureus* and in treating or ameliorating bacteremia in an animal. Thus, in an aspect of the invention, a method is provided for decolonization, inhibition or treatment of a *S. aureus* infection in an animal comprising administering to an animal a composition comprising or a combination of PlySs2 lysin and daptomycin.

In accordance with the present invention, compositions and methods comprising PlySs2 and one or more antibiotic are provided for the prevention, disruption and treatment of bacterial infection or colonization. In its broadest aspect, the present invention provides use and application of a lysin having broad killing activity against multiple bacteria, particularly gram-positive bacteria, including *Staphylococcus, Streptococcus, Enterococcus* and *Listeria* bacterial strains, in combination with antibiotic, particularly in combination with daptomycin, vancomycin, linezolid or oxacillin, or a related antibiotic, for the prevention, amelioration or treatment of gram positive bacteria or gram positive bacterial infections. The invention thus contemplates treatment, decolonization, and/or decontamination of bacteria by administration of or contact with a combination of PlySs2 lysin and one or more antibiotic wherein one or more gram positive bacteria, particularly one or more of *Staphylococcus, Streptococcus, Enterococcus* and *Listeria* bacteria, is suspected or present. In one such aspect, PlySs2 lysin is combined with daptomycin. In a further aspect, PlySs2 lysin is combined with vancomycin. In another aspect, PlySs2 lysin is combined with linezolid. In an additional aspect, PlySs2 lysin is combined with oxacillin. In each instance the antibiotic includes or encompasses related antibiotics, including those of the same class or family or with similar or related structures.

In accordance with the present invention, bacteriophage lysin derived from *Streptococcus suis* bacteria are utilized in the methods and compositions of the invention. The lysin polypeptide(s) of use in the present invention, particularly PlySs2 lysin as provided herein and in FIG. 29 (SEQ ID NO: 1), are unique in demonstrating broad killing activity against multiple bacteria, particularly gram-positive bacteria, including *Staphylococcus, Streptococcus, Enterococcus* and *Listeria* bacterial strains. In one such aspect, the PlySs2 lysin is capable of killing *Staphylococcus aureus* strains and bacteria in combination with antibiotic, particularly in combination with daptomycin, vancomycin, oxacillin or linezolid, as demonstrated herein. PlySs2 is effective against antibiotic-resistant *Staphylococcus aureus* such as methicillin-resistant *Staphylococcus aureus* (MRSA), vancomycin resistant *Staphylococcus aureus* (VRSA), daptomycin-resistant *Staphylococcus aureus* (DRSA) and linezolid-resistant *Staphylococcus aureus* (LRSA). PlySs2 is effective against vancomycin intermediate-sensitivity *Staphylococcus aureus* (VISA).

In an aspect of the invention, a method is provided of killing gram-positive bacteria comprising the step of contacting the bacteria with a combination of PlySs2 lysin and one or more antibiotic, the combination comprising an amount of an isolated lysin polypeptide effective to kill gram-positive bacteria, including *S. aureus*, the isolated lysin polypeptide comprising the PlySs2 lysin polypeptide or variants thereof effective to kill gram-positive bacteria, wherein the amount of PlySs2 required to be effective to kill gram-positive bacteria, including *S. aureus*, in the presence of antibiotic is significantly less than in the absence of antibiotic. The isolated PlySs2 lysin polypeptide may comprise the amino acid sequence provided in FIG. 29 (SEQ ID NO: 1) or variants thereof having at least 80% identity, 85% identity, 90% identity, 95% identity or 99% identity to the polypeptide of FIG. 29 (SEQ ID NO: 1) and effective to kill the gram-positive bacteria.

In an aspect of the invention, a method is provided of killing gram-positive bacteria comprising the step of contacting the bacteria with a combination of PlySs2 lysin and one or more antibiotic, the combination comprising an amount of an isolated lysin polypeptide effective to kill gram-positive bacteria, including *S. aureus*, the isolated lysin polypeptide comprising the PlySs2 lysin polypeptide or variants thereof effective to kill gram-positive bacteria, wherein the amount of antibiotic required to be effective to kill gram-positive bacteria, including *S. aureus*, in the presence of PlySs2 is significantly less than in the absence of PlySs2.

As demonstrated in accordance with the present invention, lysin as provided herein, particularly including lysin with activity against *Staphylococcus* and *Streptococcus* bacteria, particularly including PlySs2, acts synergistically with antibiotics, particularly antibiotics of different class and anti-bacterial mechanism. Thus, in accordance with the invention PlySs2 lysins or active variants thereof demonstrate enhanced activity in combination with antibiotics, including each of antibiotics affecting cell wall synthesis such as glycopeptides, penicillins which inhibit formation of peptidoglycan, protein synthesis inhibitors, and lipopeptide antibiotic. In each instance the antibacterial activity of both lysin and antibiotic is significantly enhanced in combination. Combination with glycopeptides antibiotic is evidenced by vancomycin, combination with penicillin class is evidenced by oxacillin, combination with protein synthesis inhibitor antibiotic including the class of oxazolidinone is evidenced by linezolid, and combination with lipopeptide antibiotic is evidenced by daptomycin. The present invention includes and contemplates combinations and enhanced activity with the demonstrated antibiotics as well as alternative members of their class or a related antibiotic.

Thus, in an aspect of the invention, a method is provided of killing gram-positive bacteria comprising the step of contacting the bacteria with a combination of lysin and daptomycin or a related antibiotic, the combination comprising an amount of an isolated lysin polypeptide effective to kill gram-positive bacteria, including *S. aureus*, wherein the amount of daptomycin or related antibiotic required to be effective to kill gram-positive bacteria, including *S. aureus*, in the presence of lysin is significantly less than in the absence of lysin.

In a further aspect, a method is provided of killing gram-positive bacteria comprising the step of contacting the bacteria with a combination of lysin and vancomycin or a related antibiotic, the combination comprising an amount of an isolated lysin polypeptide effective to kill gram-positive bacteria, including *S. aureus*, wherein the amount of vancomycin or related antibiotic required to be effective to kill gram-positive bacteria, including *S. aureus*, in the presence of lysin is significantly less than in the absence of lysin.

In a further aspect, a method is provided of killing gram-positive bacteria comprising the step of contacting the bacteria with a combination of lysin and oxacillin or a related antibiotic, the combination comprising an amount of an isolated lysin polypeptide effective to kill gram-positive bacteria, including *S. aureus*, wherein the amount of oxacillin or related antibiotic required to be effective to kill gram-positive bacteria, including *S. aureus*, in the presence of lysin is significantly less than in the absence of lysin.

In a further aspect, a method is provided of killing gram-positive bacteria comprising the step of contacting the bacteria with a combination of lysin and linezolid or a related antibiotic, the combination comprising an amount of an isolated lysin polypeptide effective to kill gram-positive bacteria, including *S. aureus*, wherein the amount of linezolid or related antibiotic required to be effective to kill gram-positive bacteria, including *S. aureus*, in the presence of lysin is significantly less than in the absence of lysin.

The invention also provides a method of killing antibiotic-resistant gram positive bacteria comprising contacting the antibiotic-resistant bacteria with a lysin capable of killing Staphylococcal bacteria. In one such aspect, the antibiotic-resistant bacteria is contacted with lysin, particularly PlySs2, in combination with an antibiotic to which the bacteria are sensitive to, or in combination with antibiotic to which the bacteria are resistant. In one such aspect of the method, the lysin is PLySs2. In one such aspect, the lysin is a polypeptide comprising the amino acid sequence provided in FIG. 29 (SEQ ID NO: 1) or variants thereof having at least 80% identity, 85% identity, 90% identity, 95% identity or 99% identity to the polypeptide of FIG. 29 (SEQ ID NO: 1) and effective to kill gram-positive bacteria, particularly *S. aureus*.

The invention provides such a method of killing daptomycin resistant gram positive bacteria comprising contacting the daptomycin resistant bacteria with a lysin capable of killing Staphylococcal bacteria. Such method may include combination of the lysin with daptomycin and/or with another antibiotic. In one such aspect of the method, the lysin is PLySs2 as provided herein.

The invention further provides such a method of killing vancomycin resistant gram positive bacteria comprising contacting the vancomycin resistant bacteria with a lysin capable of killing Staphylococcal bacteria. Such method may include combination of the lysin with vancomycin and/or with another antibiotic. In one such aspect of the method, the lysin is PLySs2.

In an aspect of the above methods, the methods are performed in vitro, ex vivo, or along with implantation or placement of a device in vivo so as to sterilize or decontaminate a solution, material or device, particularly intended for use by or in a human.

In a further aspect, a method is provided of enhancing antibiotic effectiveness in killing or decolonizing gram-positive bacteria comprising the step of contacting the bacteria with a combination of lysin, particularly PlySs2, and one or more antibiotic, wherein the amount of antibiotic required to be effective to kill or decolonize the gram-positive bacteria, including *S. aureus*, in the presence of lysin is significantly less than in the absence of lysin. In one such aspect, a method is providing for enhancing or facilitating the effectiveness of daptomycin or a related antibiotic against Streptococcal pneumonia comprising administering a lysin, particularly PlySs2, in combination with daptomycin. In a particular such method or aspect, daptomycin is effective against Streptococcal pneumonia when administered in combination with or subsequent to administration of lysin, particularly PlySs2, at a daptomycin dose which is ineffective in the absence of lysin, particularly PlySs2.

The invention provides a method for reducing a population of gram-positive bacteria comprising the step of contacting the bacteria with a composition comprising an amount of an isolated lysin polypeptide independently ineffective to kill the gram-positive bacteria and an amount of antibiotic independently ineffective to kill the gram-positive bacteria. The antibiotic may be a glycopeptide, penicillin, protein synthesis inhibitor, ozalidinone or lipopeptide. Such method may include an antibiotic selected from vancomycin, daptomycin, linezolid and oxacillin. In an aspect, the isolated lysin polypeptide comprises the amino acid sequence of FIG. 29 or SEQ ID NO: 1) or variants thereof having at least 80% identity to the polypeptide of FIG. 29 or SEQ ID NO: 1 and effective to kill the gram-positive bacteria.

The invention provides a method for reducing a population of gram-positive bacteria comprising the step of contacting the bacteria with a composition comprising an amount of an isolated lysin polypeptide independently ineffective to kill the gram-positive bacteria and an amount of daptomycin independently ineffective to kill the gram-positive bacteria. In an aspect, the isolated lysin polypeptide comprises the amino acid sequence of FIG. 29 (SEQ ID NO: 1) or variants thereof having at least 80% identity to the polypeptide of FIG. 29 (SEQ ID NO:1) and effective to kill the gram-positive bacteria.

In any such above method or methods, the susceptible, killed, dispersed or treated bacteria may be selected from *Staphylococcus aureus, Listeria monocytogenes, Staphylococcus simulans, Streptococcus suis, Staphylococcus epidermidis, Streptococcus equi, Streptococcus equi zoo, Streptococcus agalactiae* (GBS), *Streptococcus pyogenes* (GAS), *Streptococcus sanguinis, Streptococcus gordonii, Streptococcus dysgalactiae*, Group G *Streptococcus*, Group E *Streptococcus, Enterococcus faecalis* and *Streptococcus pneumonia*.

In accordance with any of the methods of the invention, the susceptible bacteria may be an antibiotic resistant bacteria. The bacteria may be methicillin-resistant *Staphylococcus aureus* (MRSA), vancomycin intermediate-sensitivity *Staphylococcus aureus* (VISA), vancomycin resistant *Staphylococcus aureus* (VRSA), daptomycin-resistant *Staphylococcus aureus* (DRSA), or linezolid-resistant *Staphylococcus aureus* (LRSA). The susceptible bacteria may be a clinically relevant or pathogenic bacteria, particularly for humans. In an aspect of the method(s), the lysin polyp eptide(s) is effective to kill *Staphylococcus, Streptococcus, Enterococcus* and *Listeria* bacterial strains.

In an additional aspect or embodiment of the methods and compositions provided herein, another distinct staphylococcal specific lysin is used herein alone or in combination with the PlySs2 lysin as provided and described herein. In one such aspect or embodiment of the methods and compositions provided herein, the staphylococcal specific lysin ClyS is used herein alone or in combination with the PlySs2 lysin as provided and described herein.

The invention provides methods for enhancing or facilitating antibiotic activity comprising administering a combination together or in series of lysin, particularly PlySs2 lysin, and one or more antibiotic. In an aspect thereof, antibiotic activity is enhanced or facilitated by at least 10 fold, at least 16 fold, at least 20 fold, at least 24 fold, at least 30 fold, at least 40 fold, at least 50 fold, at least 70 fold, at least 80 fold at least 100 fold, more than 10 fold, more than 20 fold, more than 50 fold, more than 100 fold. The invention provides methods for enhancing or facilitating lysin activity, particularly PlySs2 lysin, comprising administering a combination together or in series of lysin, particularly PlySs2 lysin, and one or more antibiotic. In an aspect thereof, the activity of lysin, particularly PlySs2 is enhanced at least 2 fold, at least 4 fold, at least 8 fold, at least 10 fold, up to 10 fold, up to 16 fold, up to 20 fold.

The invention includes a method of potentiating antibiotic activity against gram-positive bacteria in biological fluids having surfactant-like activity comprising administering antibiotic in combination with PlySs2 lysin comprising the amino acid sequence provided in FIG. 29 (SEQ ID NO: 1) or variants thereof having at least 80% identity, 85% identity, 90% identity, 95% identity or 99% identity to the polypeptide of FIG. 29 (SEQ ID NO: 1) and effective to kill gram-positive bacteria, wherein the antibiotic is effective in combination with PlySs2 at doses that the antibiotic is ineffective in the absence of PlySs2. In an aspect of the method, the antibiotic is daptomycin or a related compound. In an aspect, the bacteria is *S. pneumoniae*.

Other objects and advantages will become apparent to those skilled in the art from a review of the following description which proceeds with reference to the following illustrative drawings.

BRIEF DESCRIPTION OF THE DRAWINGS

FIG. 5 shows time kill curves for MRSA strains treated with PlySs2 and vancomycin alone or in combination at the noted sub MIC doses.

FIG. 6 shows time kill curves for MRSA strains treated with PlySs2 and daptomycin alone or in combination at the noted sub MIC doses.

FIG. 13 provides a panel of dose dilutions of pairings of daptomycin and PlySs2 at the noted concentrations on MRSA strain 270 in the presence and absence of BME.

FIG. 16 provides a panel of dose dilutions of pairings of daptomycin and PlySs2 at the noted concentrations on MRSA strain 263 in the presence and absence of BME.

FIG. 17 provides a panel of dose dilutions of pairings of daptomycin and PlySs2 at the noted concentrations on MRSA strain 650 in the presence and absence of BME.

FIG. 19 depicts representative isobolograms depicting FIC values of lysin PlySs2 versus FIC values of antibiotic. PlySs2 versus antibiotics oxacillin, vancomycin and daptomycin are depicted against MSSA strains and MRSA strains as noted. Oxacillin and PlySs2 are evaluated versus MSSA strain JMI 33611. PlySs2 and vancomycin are evaluated versus MSSA strain JMI 9365 and MRSA strain JMI 6456. Daptomycin and PlySs2 are evaluated versus MSSA strain JMI 33611 and MRSA JMI 3345.

FIG. 21 depicts the fold change in MIC value against MRSA strain MW2 and MSSA strain ATCC 29213 treated with PlySs2 or daptomycin in the presence of varying amounts of surfactant (from 1.25 to 15% surfactant).

FIG. 29 provides the amino acid sequence (SEQ ID NO: 1) and encoding nucleic acid sequence (SEQ ID NO: 2) of the lysin PlySs2. The N-terminal CHAP domain and the C-terminal SH-3 domain of the PlySs2 lysin are shaded, with the CHAP domain (SEQ ID NO: 3) starting with LNN . . . and ending with . . . YIT and the SH-3 domain (SEQ ID NO: 4) starting with RSY . . . and ending with . . . VAT. The CHAP domain active-site residues ($Cys_{26}$, $His_{102}$, $Glu_{118}$, and $Asn_{120}$) identified by homology to PDB 2K3A (Rossi P et al (2009) Proteins 74:515-519) are underlined.

DETAILED DESCRIPTION

Figure 1:
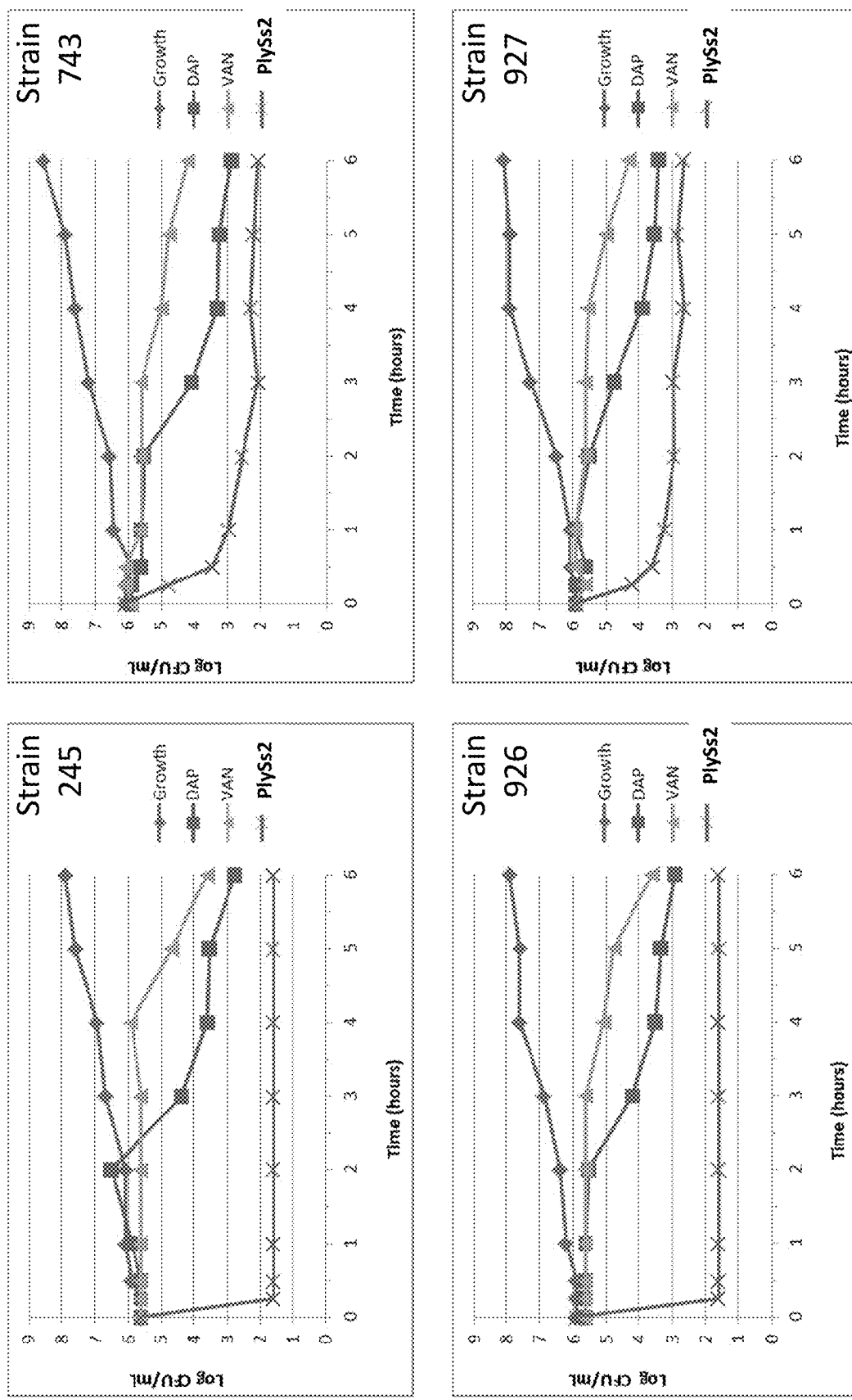
FIG. 1 depicts time kill curves of various MRSA strains in the presence of added daptomycin, vancomycin or PlySs2 lysin.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]1; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "PlySs lysin(s)", "PlySs2 lysin", "PlySs2" and any variants not specifically listed, may be used herein interchangeably, and as used throughout the present application and claims refer to proteinaceous material including single or multiple proteins, and extends to those proteins having the amino acid sequence data described herein and presented in FIG. 29 and SEQ ID NO: 1, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "PlySs lysin(s)", "PlySs2 lysin", "PlySs2" are intended to include within their scope proteins specifically recited herein as well as all substantially homologous analogs, fragments or truncations, and allelic variations. PlySs2 lysin is described in U.S. Patent Application 61/477,836 and PCT Application PCT/US2012/34456. A more recent paper Gilmer et al describes PlySs2 lysin (Gilmer D B et al (2013) Antimicrob Agents Chemother Epub 2013 Apr. 9 [PMID 23571534]).

The term "ClyS", "ClyS lysin" refers to a chimeric lysin ClyS, with activity against Staphylococci bacteria, including Staphylococcus aureus, is detailed in WO 2010/002959 and also described in Daniel et al (Daniel, A et al (2010) Antimicrobial Agents and Chemother 54(4):1603-1612). Exemplary ClyS amino acid sequence is provided in SEQ ID NO: 5.

A "lytic enzyme" includes any bacterial cell wall lytic enzyme that kills one or more bacteria under suitable conditions and during a relevant time period. Examples of lytic enzymes include, without limitation, various amidase cell wall lytic enzymes. In a particular aspect, a lytic enzyme refers to a bacteriophage lytic enzyme. A "bacteriophage lytic enzyme" refers to a lytic enzyme extracted or isolated from a bacteriophage or a synthesized lytic enzyme with a similar protein structure that maintains a lytic enzyme functionality.

A lytic enzyme is capable of specifically cleaving bonds that are present in the peptidoglycan of bacterial cells to disrupt the bacterial cell wall. It is also currently postulated that the bacterial cell wall peptidoglycan is highly conserved among most bacteria, and cleavage of only a few bonds to may disrupt the bacterial cell wall. Examples of lytic enzymes that cleave these bonds are muramidases, glucosaminidases, endopeptidases, or N-acetyl-muramoyl-L-alanine amidases. Fischetti et al (1974) reported that the C1 streptococcal phage lysin enzyme was an amidase. Garcia et al (1987, 1990) reported that the Cpl lysin from a *S. pneumoniae* from a Cp-1 phage was a lysozyme. Caldentey and Bamford (1992) reported that a lytic enzyme from the phi 6 *Pseudomonas* phage was an endopeptidase, splitting the peptide bridge formed by melo-diaminopimilic acid and D-alanine. The *E. coli* T1 and T6 phage lytic enzymes are amidases as is the lytic enzyme from *Listeria* phage (ply) (Loessner et al, 1996). There are also other lytic enzymes known in the art that are capable of cleaving a bacterial cell wall.

A "lytic enzyme genetically coded for by a bacteriophage" includes a polypeptide capable of killing a host bacteria, for instance by having at least some cell wall lytic activity against the host bacteria. The polypeptide may have a sequence that encompasses native sequence lytic enzyme and variants thereof. The polypeptide may be isolated from a variety of sources, such as from a bacteriophage ("phage"), or prepared by recombinant or synthetic methods. The polypeptide may, for example, comprise a choline-binding portion at the carboxyl terminal side and may be characterized by an enzyme activity capable of cleaving cell wall peptidoglycan (such as amidase activity to act on amide bonds in the peptidoglycan) at the amino terminal side. Lytic enzymes have been described which include multiple enzyme activities, for example two enzymatic domains, such as PlyGBS lysin. Further, other lytic enzymes have been described containing only a catalytic domain and no cell wall binding domain.

"A native sequence phage associated lytic enzyme" includes a polypeptide having the same amino acid sequence as an enzyme derived from a bacterial genome (i.e., a prophage). Such native sequence enzyme can be isolated or can be produced by recombinant or synthetic means.

The term "native sequence enzyme" encompasses naturally occurring forms (e.g., alternatively spliced or altered forms) and naturally-occurring variants of the enzyme. In one embodiment of the invention, the native sequence enzyme is a mature or full-length polypeptide that is genetically coded for by a gene from a bacteriophage specific for *Streptococcus suis*. Of course, a number of variants are possible and known, as acknowledged in publications such as Lopez et al., Microbial Drug Resistance 3: 199-211 (1997); Garcia et al., Gene 86: 81-88 (1990); Garcia et al., Proc. Natl. Acad. Sci. USA 85: 914-918 (1988); Garcia et al., Proc. Natl. Acad. Sci. USA 85: 914-918 (1988); Garcia et al., Streptococcal Genetics (J. J. Ferretti and Curtis eds., 1987); Lopez et al., FEMS Microbiol. Lett. 100: 439-448 (1992); Romero et al., J. Bacteriol. 172: 5064-5070 (1990); Ronda et al., Eur. J. Biochem. 164: 621-624 (1987) and Sanchez et al., Gene 61: 13-19 (1987). The contents of each of these references, particularly the sequence listings and associated text that compares the sequences, including statements about sequence homologies, are specifically incorporated by reference in their entireties.

"A variant sequence lytic enzyme" includes a lytic enzyme characterized by a polypeptide sequence that is different from that of a lytic enzyme, but retains functional activity. The lytic enzyme can, in some embodiments, be genetically coded for by a bacteriophage specific for *Streptococcus suis* as in the case of PlySs2 having a particular amino acid sequence identity with the lytic enzyme sequence(s) hereof, as provided in FIG. 29 and in SEQ ID NO: 1. For example, in some embodiments, a functionally active lytic enzyme can kill *Streptococcus suis* bacteria, and other susceptible bacteria as provided herein, including as shown in TABLE 1, 2 and 3, by disrupting the cellular wall of the bacteria. An active lytic enzyme may have a 60, 65, 70, 75, 80, 85, 90, 95, 97, 98, 99 or 99.5% amino acid sequence identity with the lytic enzyme sequence(s) hereof, as provided in FIG. 29 (SEQ ID NO: 1, SEQ ID NO: 3 or SEQ ID NO: 4). Such phage associated lytic enzyme variants include, for instance, lytic enzyme polypeptides wherein one or more amino acid residues are added, or deleted at the N or C terminus of the sequence of the lytic enzyme sequence(s) hereof, as provided in FIG. 29 (SEQ ID NO: 1).

In a particular aspect, a phage associated lytic enzyme will have at least about 80% or 85% amino acid sequence identity with native phage associated lytic enzyme sequences, particularly at least about 90% (e.g. 90%) amino acid sequence identity. Most particularly a phage associated lytic enzyme variant will have at least about 95% (e.g. 95%) amino acid sequence identity with the native phage associated the lytic enzyme sequence(s) hereof, as provided in FIG. 29 (SEQ ID NO: 1) for PlySs2 lysin, or as previously described for ClyS including in WO 2010/002959 and also described in Daniel et al (Daniel, A et al (2010) Antimicrobial Agents and Chemother 54(4):1603-1612) and SEQ ID NO: 5.

"Percent amino acid sequence identity" with respect to the phage associated lytic enzyme sequences identified is defined herein as the percentage of amino acid residues in a candidate sequence that are identical with the amino acid residues in the phage associated lytic enzyme sequence, after aligning the sequences in the same reading frame and introducing gaps, if necessary, to achieve the maximum percent sequence identity, and not considering any conservative substitutions as part of the sequence identity.

"Percent nucleic acid sequence identity" with respect to the phage associated lytic enzyme sequences identified herein is defined as the percentage of nucleotides in a candidate sequence that are identical with the nucleotides in the phage associated lytic enzyme sequence, after aligning the sequences and introducing gaps, if necessary, to achieve the maximum percent sequence identity.

To determine the percent identity of two nucleotide or amino acid sequences, the sequences are aligned for optimal comparison purposes (e.g., gaps may be introduced in the sequence of a first nucleotide sequence). The nucleotides or amino acids at corresponding nucleotide or amino acid positions are then compared. When a position in the first sequence is occupied by the same nucleotide or amino acid as the corresponding position in the second sequence, then the molecules are identical at that position. The percent identity between the two sequences is a function of the number of identical positions shared by the sequences (i.e., % identity=# of identical positions/total # of positions×100).

The determination of percent identity between two sequences may be accomplished using a mathematical algorithm. A non-limiting example of a mathematical algorithm utilized for the comparison of two sequences is the algorithm of Karlin et al., Proc. Natl. Acad. Sci. USA, 90:5873-5877 (1993), which is incorporated into the NBLAST program which may be used to identify sequences having the desired identity to nucleotide sequences of the invention. To obtain gapped alignments for comparison purposes, Gapped BLAST may be utilized as described in Altschul et al., Nucleic Acids Res, 25:3389-3402 (1997). When utilizing BLAST and Gapped BLAST programs, the default parameters of the respective programs (e.g., NBLAST) may be used. See the programs provided by National Center for Biotechnology Information, National Library of Medicine, National Institutes of Health.

"Polypeptide" includes a polymer molecule comprised of multiple amino acids joined in a linear manner. A polypeptide can, in some embodiments, correspond to molecules encoded by a polynucleotide sequence which is naturally occurring. The polypeptide may include conservative substitutions where the naturally occurring amino acid is replaced by one having similar properties, where such conservative substitutions do not alter the function of the polyp eptide.

The term "altered lytic enzymes" includes shuffled and/or chimeric lytic enzymes.

Phage lytic enzymes specific for bacteria infected with a specific phage have been found to effectively and efficiently break down the cell wall of the bacterium in question. The lytic enzyme is believed to lack proteolytic enzymatic activity and is therefore non-destructive to mammalian proteins and tissues when present during the digestion of the bacterial cell wall. Furthermore, because it has been found that the action of phage lytic enzymes, unlike antibiotics, was rather specific for the target pathogen(s), it is likely that the normal flora will remain essentially intact (M. J. Loessner, G. Wendlinger, S. Scherer, Mol Microbiol 16, 1231-41. (1995) incorporated herein by reference). In fact, the PlySs2 lysin, while demonstrating uniquely broad bacterial species and strain killing, is comparatively and particularly inactive against bacteria comprising the normal flora, including E. coli, as described herein.

A lytic enzyme or polypeptide of use in the invention may be produced by the bacterial organism after being infected with a particular bacteriophage or may be produced or prepared recombinantly or synthetically as either a prophylactic treatment for preventing those who have been exposed to others who have the symptoms of an infection from getting sick, or as a therapeutic treatment for those who have already become ill from the infection. In as much the lysin polypeptide sequences and nucleic acids encoding the lysin polypeptides are described and referenced to herein, the lytic enzyme(s)/polypeptide(s) may be preferably produced via the isolated gene for the lytic enzyme from the phage genome, putting the gene into a transfer vector, and cloning said transfer vector into an expression system, using standard methods of the art, including as exemplified herein. The lytic enzyme(s) or polypeptide(s) may be truncated, chimeric, shuffled or "natural," and may be in combination. Relevant U.S. Pat. No. 5,604,109 is incorporated herein in its entirety by reference. An "altered" lytic enzyme can be produced in a number of ways. In a preferred embodiment, a gene for the altered lytic enzyme from the phage genome is put into a transfer or movable vector, preferably a plasmid, and the plasmid is cloned into an expression vector or expression system. The expression vector for producing a lysin polypeptide or enzyme of the invention may be suitable for E. coli, Bacillus, or a number of other suitable bacteria. The vector system may also be a cell free expression system. All of these methods of expressing a gene or set of genes are known in the art. The lytic enzyme may also be created by infecting Streptococcus suis with a bacteriophage specific for Streptococcus suis, wherein said at least one lytic enzyme exclusively lyses the cell wall of said Streptococcus suis having at most minimal effects on other, for example natural or commensal, bacterial flora present.

A "chimeric protein" or "fusion protein" comprises all or (preferably a biologically active) part of a polypeptide of use in the invention operably linked to a heterologous polypeptide. Chimeric proteins or peptides are produced, for example, by combining two or more proteins having two or more active sites. Chimeric protein and peptides can act independently on the same or different molecules, and hence have a potential to treat two or more different bacterial infections at the same time. Chimeric proteins and peptides also may be used to treat a bacterial infection by cleaving the cell wall in more than one location, thus potentially providing more rapid or effective (or synergistic) killing from a single lysin molecule or chimeric peptide.

A "heterologous" region of a DNA construct or peptide construct is an identifiable segment of DNA within a larger DNA molecule or peptide within a larger peptide molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA or peptide as defined herein.

The term "operably linked" means that the polypeptide of the disclosure and the heterologous polypeptide are fused in-frame. The heterologous polypeptide can be fused to the N-terminus or C-terminus of the polypeptide of the disclosure. Chimeric proteins are produced enzymatically by chemical synthesis, or by recombinant DNA technology. A number of chimeric lytic enzymes have been produced and studied. One example of a useful fusion protein is a GST fusion protein in which the polypeptide of the disclosure is fused to the C-terminus of a GST sequence. Such a chimeric protein can facilitate the purification of a recombinant polypeptide of the disclosure.

In another embodiment, the chimeric protein or peptide contains a heterologous signal sequence at its N-terminus. For example, the native signal sequence of a polypeptide of the disclosure can be removed and replaced with a signal sequence from another known protein.

The fusion protein may combine a lysin polypeptide with a protein or polypeptide of having a different capability, or providing an additional capability or added character to the lysin polypeptide. The fusion protein may be an immunoglobulin fusion protein in which all or part of a polypeptide of the disclosure is fused to sequences derived from a member of the immunoglobulin protein family. The immunoglobulin may be an antibody, for example an antibody directed to a surface protein or epitope of a susceptible or target bacteria. The immunoglobulin fusion protein can alter bioavailability of a cognate ligand of a polypeptide of the disclosure. Inhibition of ligand/receptor interaction may be useful therapeutically, both for treating bacterial-associated diseases and disorders for modulating (i.e. promoting or inhibiting) cell survival. The fusion protein may include a means to direct or target the lysin, including to particular tissues or organs or to surfaces such as devices, plastic, membranes. Chimeric and fusion proteins and peptides of the disclosure can be produced by standard recombinant DNA techniques.

A modified or altered form of the protein or peptides and peptide fragments, as disclosed herein, includes protein or peptides and peptide fragments that are chemically synthesized or prepared by recombinant DNA techniques, or both. These techniques include, for example, chimerization and shuffling. As used herein, shuffled proteins or peptides, gene products, or peptides for more than one related phage protein or protein peptide fragments have been randomly cleaved and reassembled into a more active or specific protein. Shuffled oligonucleotides, peptides or peptide fragment molecules are selected or screened to identify a molecule having a desired functional property. Shuffling can be used to create a protein that is more active, for instance up to 10 to 100 fold more active than the template protein. The template protein is selected among different varieties of lysin proteins. The shuffled protein or peptides constitute, for example, one or more binding domains and one or more catalytic domains. When the protein or peptide is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

The present invention also pertains to other variants of the polypeptides useful in the invention. Such variants may have an altered amino acid sequence which can function as either agonists (mimetics) or as antagonists. Variants can be generated by mutagenesis, i.e., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein. Variants of a protein of use in the disclosure which function as either agonists (mimetics) or as antagonists can be identified by screening combinatorial libraries of mutants, such as truncation mutants, of the protein of the disclosure. In one embodiment, a variegated library of variants is generated by combinatorial mutagenesis at the nucleic acid level and is encoded by a variegated gene library. There are a variety of methods which can be used to produce libraries of potential variants of the polypeptides of the disclosure from a degenerate oligonucleotide sequence. Libraries of fragments of the coding sequence of a polypeptide of the disclosure can be used to generate a variegated population of polypeptides for screening and subsequent selection of variants, active fragments or truncations. Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. In this context, the smallest portion of a protein (or nucleic acid that encodes the protein) according to embodiments is an epitope that is recognizable as specific for the phage that makes the lysin protein. Accordingly, the smallest polypeptide (and associated nucleic acid that encodes the polypeptide) that can be expected to bind a target or receptor, such as an antibody, and is useful for some embodiments may be 8, 9, 10, 11, 12, 13, 15, 20, 25, 30, 35, 40, 45, 50, 55, 60, 65, 75, 85, or 100 amino acids long. Although small sequences as short as 8, 9, 10, 11, 12 or 15 amino acids long reliably comprise enough structure to act as targets or epitopes, shorter sequences of 5, 6, or 7 amino acids long can exhibit target or epitopic structure in some conditions and have value in an embodiment. Thus, the smallest portion of the protein(s) or lysin polypeptides provided herein, including as set out in FIG. 29 (SEQ ID NO: 1) includes polypeptides as small as 5, 6, 7, 8, 9, 10, 12, 14 or 16 amino acids long.

Biologically active portions of a protein or peptide fragment of the embodiments, as described herein, include polypeptides comprising amino acid sequences sufficiently identical to or derived from the amino acid sequence of the lysin protein of the disclosure, which include fewer amino acids than the full length protein of the lysin protein and exhibit at least one activity of the corresponding full-length protein. Typically, biologically active portions comprise a domain or motif with at least one activity of the corresponding protein. An exemplary domain sequence for the N terminal CHAP domain of the lysin of the present invention is provided in FIG. 29 and SEQ ID NO: 3. An exemplary domain sequence for the C terminal SH3 domain of the lysin of the present invention is provided in FIG. 29 and SEQ ID NO: 4. A biologically active portion of a protein or protein fragment of the disclosure can be a polypeptide which is, for example, 10, 25, 50, 100 less or more amino acids in length. Moreover, other biologically active portions, in which other regions of the protein are deleted, or added can be prepared by recombinant techniques and evaluated for one or more of the functional activities of the native form of a polypeptide of the embodiments.

Homologous proteins and nucleic acids can be prepared that share functionality with such small proteins and/or nucleic acids (or protein and/or nucleic acid regions of larger molecules) as will be appreciated by a skilled artisan. Such small molecules and short regions of larger molecules that may be homologous specifically are intended as embodiments. Preferably the homology of such valuable regions is at least 50%, 65%, 75%, 80%, 85%, and preferably at least 90%, 95%, 97%, 98%, or at least 99% compared to the lysin polypeptides provided herein, including as set out in FIG. 29. These percent homology values do not include alterations due to conservative amino acid substitutions.

Two amino acid sequences are "substantially homologous" when at least about 70% of the amino acid residues (preferably at least about 80%, at least about 85%, and preferably at least about 90 or 95%) are identical, or represent conservative substitutions. The sequences of comparable lysins, such as comparable PlySs2 lysins, or comparable ClyS lysins, are substantially homologous when one or more, or several, or up to 10%, or up to 15%, or up to 20% of the amino acids of the lysin polypeptide are substituted with a similar or conservative amino acid substitution, and wherein the comparable lysins have the profile of activities, anti-bacterial effects, and/or bacterial specificities of a lysin, such as the PlySs2 lysin and/or ClyS lysin, disclosed herein.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

Mutations can be made in the amino acid sequences, or in the nucleic acid sequences encoding the polypeptides and lysins herein, including in the lysin sequences set out in FIG. 29 (SEQ ID NO: 1), or in active fragments or truncations thereof, such that a particular codon is changed to a codon which codes for a different amino acid, an amino acid is substituted for another amino acid, or one or more amino acids are deleted. Such a mutation is generally made by making the fewest amino acid or nucleotide changes possible. A substitution mutation of this sort can be made to change an amino acid in the resulting protein in a non-conservative manner (for example, by changing the codon from an amino acid belonging to a grouping of amino acids having a particular size or characteristic to an amino acid belonging to another grouping) or in a conservative manner (for example, by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

Thus, one of skill in the art, based on a review of the sequence of the PlySs2 lysin polypeptide provided herein and on their knowledge and the public information available for other lysin polypeptides, can make amino acid changes or substitutions in the lysin polypeptide sequence. Amino acid changes can be made to replace or substitute one or more, one or a few, one or several, one to five, one to ten, or such other number of amino acids in the sequence of the lysin(s) provided herein to generate mutants or variants thereof. Such mutants or variants thereof may be predicted for function or tested for function or capability for killing bacteria, including *Staphylococcal, Streptococcal, Listeria*, or *Enterococcal* bacteria, and/or for having comparable activity to the lysin(s) as described and particularly provided herein. Thus, changes can be made to the sequence of lysin, and mutants or variants having a change in sequence can be tested using the assays and methods described and exemplified herein, including in the examples. One of skill in the art, on the basis of the domain structure of the lysin(s) hereof can predict one or more, one or several amino acids suitable for substitution or replacement and/or one or more amino acids which are not suitable for substitution or replacement, including reasonable conservative or non-conservative substitutions.

In this regard, and with exemplary reference to PlySs2 lysin it is pointed out that, although the PlySs2 polypeptide lysin represents a divergent class of prophage lytic enzyme, the lysin comprises an N-terminal CHAP domain (cysteine-histidine amidohydrolase/peptidase) (SEQ ID NO: 3) and a C-terminal SH3-type 5 domain (SEQ ID NO: 4) as depicted in FIG. 29. The domains are depicted in the amino acid sequence in distinct shaded color regions, with the CHAP domain corresponding to the first shaded amino acid sequence region starting with LNN . . . and the SH3-type 5 domain corresponding to the second shaded region starting with RSY . . . CHAP domains are included in several previously characterized streptococcal and staphylococcal phage lysins. Thus, one of skill in the art can reasonably make and test substitutions or replacements to the CHAP domain and/or the SH-3 domain of PlySs2. Sequence comparisons to the Genbank database can be made with either or both of the CHAP and/or SH-3 domain sequences or with the PlySs2 lysin full amino acid sequence, for instance, to identify amino acids for substitution. For example, the CHAP domain contains conserved cysteine and histidine amino acid sequences (the first cysteine and histidine in the CHAP domain) which are characteristic and conserved in CHAP domains of different polypeptides. It is reasonable to predict, for example, that the conserved cysteine and histidine residues should be maintained in a mutant or variant of PlySs2 so as to maintain activity or capability. It is notable that a mutant or variant having an alanine replaced for valine at valine amino acid 19 in the PlySs2 amino acid sequence of FIG. 29 (SEQ ID NO: 1) is active and capable of killing gram positive bacteria in a manner similar to and as effective as the FIG. 29 (SEQ ID NO: 1) PlySs2 lysin.

The following is one example of various groupings of amino acids:
Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at pH 6.0)
Aspartic acid, Glutamic acid
Basic Amino Acids (Positively Charged at pH 6.0)
Lysine, Arginine, Histidine (at pH 6.0)

Another grouping may be those amino acids with phenyl groups:
Phenylalanine, Tryptophan, Tyrosine Another grouping may be according to molecular weight (i.e., size of R groups):

| | | | |
|---|---|---|---|
| Glycine | 75 | Alanine | 89 |
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free NH$_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

In accordance with the present invention compositions and methods are provide based on combinations of bacteriophage lysin(s) with antibiotic are provided for rapid and effective killing of gram positive bacteria. In accordance with the invention, the lysin PlySs2, which demonstrates broad killing activity against multiple bacteria, particularly gram-positive bacteria, including Staphylococcus and Streptococcus bacterial strains, provides remarkable synergy in combination with antibiotic(s) and can significantly reduce the effective MIC doses required for antibiotic(s).

As demonstrated and provided herein, lysin particularly PlySs2 lysin is capable of synergizing with antibiotics, including antibiotics of different types and classes, including vancomycin, daptomycin, linezolid, and oxacillin, in a process characterized by improved bactericidal activity, more rapid antibiotic penetration, and suppression of resistance. In murine bacteremia models, as demonstrated herein, pairwise combinations of PlySs2 with antibiotics confer a highly significant survival increase relative to single-agent treatments. Thus, lysin/antibiotic combinations, relative to current standard treatments, will be more effective therapies for treating bacteremia in the clinic.

The invention further demonstrates PlySs2-dependent enhancement of antibiotics in combination via both in-vitro assays and in a murine model of S. aureus-induced bacteremia under conditions in which human-simulated doses of single-agent antibiotics fail. Data are presented herein illustrating the mechanism of the PlySs2-mediated enhancement of antibiotic activity and indicating a general synergy between lysins and antibiotics. Synergy has implications for an efficacious new general anti-infective strategy based on the co-administration of lysin and antibiotics. In particular each and both agents lysins and antibiotics may be administered at significantly reduced doses and amounts, with enhanced bacteriocidal and bacteriostatic activity and with reduced risk of antibiotic or agent resistance.

While lysin, particularly PlySs2 lysin, is recognized as a single agent, the present invention provides that lysin, particularly PlySs2 lysin, remarkably demonstrates a significant degree of in vitro and in vivo synergy with various antibiotics. While in the present Examples synergy is validated by time-kill curves and checkerboard assays with multiple strains and antibiotics, the extent of in vitro synergy is particularly illustrated using a dual agent MIC assay in which as little as 0.25× MIC PlySs2 reduced the daptomycin MIC from 1 µg/mL to 0.0075 µg/mL, a 128-fold decrease. This synergistic effect was seen across 12 MRSA strains with the degree of potency enhancement ranging from 64 to 256-fold. The two antimicrobials, antibiotics plus lysin, in a combination are therefore doing more than simply killing sequentially (reduction of the bulk population by lysin followed by antibiotic killing of residual bacteria) since 7.5 ng/ml daptomycin is vastly insufficient to kill as a single agent.

In the bacteremia models provided and demonstrated herein, combination therapy treatments consistently outperformed full strength human-simulated doses of single agent antibiotic treatments. This is demonstrated for both vancomycin and daptomycin, the current standard-of-care antibiotics for treating MRSA bacteremia, as well as for oxacillin, a beta-lactam, the current standard-of-care antibiotic for treating MSSA bacteremia. These results have clear clinical implications and provide new effective combination therapy regimens employing lysin(s) and antibiotic(s) for treating bacteremia as well as other serious infections. Provided are methods and compositions based on combination lysin plus antibiotic therapy using lower doses of these agents with enhanced efficacy and lower risk of resistance. Indeed the present methods and compositions are effective on resistant bacteria, including antibiotic resistant Staphylococcal bacteria.

In clinical applications, the invention provides methods of treating bacteremia by administering a lysin/antibiotic combination, particularly PlySs2/antibiotic combination. While above its MIC, the fast-acting lysin will effectively reduce the pathogen population. Once the lysin concentration falls below the MIC, the combination partner antibiotic's activity will be enhanced synergistically by the presence of the lysin for approximately one or two more lysin pharmacokinetic half-lives extending the time in which synergy-enhanced killing is active. Thus, PlySs2/antibiotic combinations will provide more potent and effective antibacterial therapies than the currently available single-agent options.

The PlySs2 lysin displays activity and capability to kill numerous distinct strains and species of gram positive bacteria, including Staphylococcal, Streptococcal, Listeria, or Enterococcal bacteria. In particular and with significance, PlySs2 is active in killing Staphylococcus strains, including Staphylococcus aureus, particularly both antibiotic-sensitive and distinct antibiotic-resistant strains. PlySs2 is also active in killing Streptococcus strains, and shows particularly effective killing against Group A and Group B streptococcus strains. PlySs2 lysin capability against bacteria is depicted below in TABLE 1, based on log kill assessments using isolated strains in vitro.

TABLE 1

PlySs2 Reduction in Growth of Different Bacteria (partial listing)

| Bacteria | Relative Kill with PlySs2 |
|---|---|
| Staphylococcus aureus (VRSA, VISA, MRSA, MSSA) | +++ |
| Streptococcus suis | +++ |
| Staphylococcus epidermidis | ++ |
| Staphylococcus simulans | +++ |
| Lysteria monocytogenes | ++ |
| Enterococcus faecalis | ++ |
| Streptococcus dysgalactiae - GBS | ++ |
| Streptococcus agalactiae - GBS | +++ |
| Streptococcus pyogenes - GAS | +++ |
| Streptococcus equi | ++ |
| Streptococcus sanguinis | ++ |
| Streptococcus gordonii | ++ |
| Streptococcus sobrinus | + |
| Streptococcus rattus | + |
| Streptococcus oralis | + |
| Streptococcus pneumonine | + |
| Bacillus thuringiensis | − |
| Bacillus cereus | − |
| Bacillus subtilis | − |
| Bacillus anthracis | − |
| Escherichia coli | − |
| Enterococcus faecium | − |
| Pseudomanas aeruginosa | − |

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "specific" may be used to refer to the situation in which one member of a specific binding pair will not show significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "comprise" generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention hereof, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which the lysin polypeptide(s) of the invention, or nucleic acid encoding such polypeptides will be, in accordance with the present invention. Polypeptides and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Polypeptides and nucleic acid may be formulated with diluents or adjuvants and still for practical purposes be isolated—for example the polypeptides will normally be mixed with polymers or mucoadhesives or other carriers, or will be mixed with pharmaceutically acceptable carriers or diluents, when used in diagnosis or therapy.

Nucleic acids capable of encoding the S. suis PlySs2 lysin polypeptide(s) useful and applicable in the invention are provided herein. Representative nucleic acid sequences in this context are polynucleotide sequences coding for the polypeptide of FIG. 29 (SEQ ID NO: 1), and sequences that hybridize, under stringent conditions, with complementary sequences of the DNA of the FIG. 29 (SEQ ID NO: 2) sequence(s). Further variants of these sequences and sequences of nucleic acids that hybridize with those shown in the figures also are contemplated for use in production of lysing enzymes according to the disclosure, including natural variants that may be obtained. A large variety of isolated nucleic acid sequences or cDNA sequences that encode phage associated lysing enzymes and partial sequences that hybridize with such gene sequences are useful for recombinant production of the lysin enzyme(s) or polypeptide(s) of the invention.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

DNA molecules and nucleotide sequences which are derivatives of those specifically disclosed herein and which differ from those disclosed by the deletion, addition or substitution of nucleotides while still encoding a protein which possesses the functional characteristic of the lysin polypeptide(s) are contemplated by the disclosure. Also included are small DNA molecules which are derived from the disclosed DNA molecules. Such small DNA molecules include oligonucleotides suitable for use as hybridization probes or polymerase chain reaction (PCR) primers. As such, these small DNA molecules will comprise at least a segment of a lytic enzyme genetically coded for by a bacteriophage of *Staphylococcus suis* and, for the purposes of PCR, will comprise at least a 10-15 nucleotide sequence and, more preferably, a 15-30 nucleotide sequence of the gene. DNA molecules and nucleotide sequences which are derived from the disclosed DNA molecules as described above may also be defined as DNA sequences which hybridize under stringent conditions to the DNA sequences disclosed, or fragments thereof.

In preferred embodiments of the present disclosure, stringent conditions may be defined as those under which DNA molecules with more than 25% sequence variation (also termed "mismatch") will not hybridize. In a more preferred embodiment, stringent conditions are those under which DNA molecules with more than 15% mismatch will not hybridize, and more preferably still, stringent conditions are those under which DNA sequences with more than 10% mismatch will not hybridize. Preferably, stringent conditions are those under which DNA sequences with more than 6% mismatch will not hybridize.

The degeneracy of the genetic code further widens the scope of the embodiments as it enables major variations in the nucleotide sequence of a DNA molecule while maintaining the amino acid sequence of the encoded protein. Thus, the nucleotide sequence of the gene could be changed at this position to any of these three codons without affecting the amino acid composition of the encoded protein or the characteristics of the protein. The genetic code and variations in nucleotide codons for particular amino acids are well known to the skilled artisan. Based upon the degeneracy of the genetic code, variant DNA molecules may be derived from the cDNA molecules disclosed herein using standard DNA mutagenesis techniques as described above, or by synthesis of DNA sequences. DNA sequences which do not hybridize under stringent conditions to the cDNA sequences disclosed by virtue of sequence variation based on the degeneracy of the genetic code are herein comprehended by this disclosure.

Thus, it should be appreciated that also within the scope of the present invention are DNA sequences encoding a lysin of the present invention, including PlySs2 and PlySs1, which sequences code for a polypeptide having the same amino acid sequence as provided in FIG. 29 (SEQ ID NO: 1), but which are degenerate thereto or are degenerate to the exemplary nucleic acids sequences provided in FIG. 29 (SEQ ID NO: 2). By "degenerate to" is meant that a different three-letter codon is used to specify a particular amino acid. It is well known in the art the codons which can be used interchangeably to code for each specific amino acid.

One skilled in the art will recognize that the DNA mutagenesis techniques described here and known in the art can produce a wide variety of DNA molecules that code for a bacteriophage lysin of *Streptococcus suis* yet that maintain the essential characteristics of the lytic polypeptides described and provided herein. Newly derived proteins may also be selected in order to obtain variations on the characteristic of the lytic polypeptide(s), as will be more fully described below. Such derivatives include those with variations in amino acid sequence including minor deletions, additions and substitutions.

While the site for introducing an amino acid sequence variation may be predetermined, the mutation per se does not need to be predetermined. Amino acid substitutions are typically of single residues, or can be of one or more, one or a few, one, two, three, four, five, six or seven residues; insertions usually will be on the order of about from 1 to 10 amino acid residues; and deletions will range about from 1 to 30 residues. Deletions or insertions may be in single form, but preferably are made in adjacent pairs, i.e., a deletion of 2 residues or insertion of 2 residues. Substitutions, deletions, insertions or any combination thereof may be combined to arrive at a final construct. Substitutional variants are those in which at least one residue in the amino acid sequence has been removed and a different residue inserted in its place. Such substitutions may be made so as to generate no significant effect on the protein characteristics or when it is desired to finely modulate the characteristics of the protein. Amino acids which may be substituted for an original amino acid in a protein and which are regarded as conservative substitutions are described above and will be recognized by one of skill in the art.

As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence. A wide variety of host/expression vector combinations may be employed in expressing the DNA sequences of this invention. Useful expression vectors, for example, may consist of segments of chromosomal, non-chromosomal and synthetic DNA sequences. Any of a wide variety of expression control sequences—sequences that control the expression of a DNA sequence operatively linked to it—may be used in these vectors to express the DNA sequences of this invention. A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, human cells and plant cells in tissue culture. One skilled in the art will be able to select the proper vectors, expression control sequences, and hosts without undue experimentation to accomplish the desired expression without departing from the scope of this invention.

Therapeutic or pharmaceutical compositions comprising the lytic enzyme(s)/polypeptide(s) of use in the methods and applications provided in the invention are provided herein, as well as related methods of use. Therapeutic or pharmaceutical compositions may comprise one or more lytic polypeptide(s), and optionally include natural, truncated, chimeric or shuffled lytic enzymes, combined with one or more antibiotics, optionally combined with suitable excipients, carriers or vehicles. The invention provides therapeutic compositions or pharmaceutical compositions of the lysins, including PlySs2, in combination with antibiotic for use in the killing, alleviation, decolonization, prophylaxis or treatment of gram-positive bacteria, including bacterial infections or related conditions. The invention provides therapeutic compositions or pharmaceutical compositions of the lysins, including PlySs2, in combination with vancomycin, linezolid or daptomycin for use in the killing, alleviation, decolonization, prophylaxis or treatment of gram-positive bacteria, including bacterial infections or related conditions. The invention provides therapeutic compositions or pharmaceutical compositions of the lysins, including PlySs2, in combination with daptomycin for use in the killing, alleviation, decolonization, prophylaxis or treatment of gram-positive bacteria, including bacterial infections or related conditions. Compositions comprising PlySs2 lysin, including truncations or variants thereof, in combination with antibiotic, including daptomycin, are provided herein for use in the killing, alleviation, decolonization, prophylaxis or treatment of gram-positive bacteria, including bacterial infections or related conditions, particularly of *Streptococcus, Staphylococcus, Enterococcus* or *Listeria*, including *Streptococcus pyogenes* and antibiotic resistant *Staphylococcus aureus*.

The enzyme(s) or polypeptide(s) included in the therapeutic compositions may be one or more or any combination of unaltered phage associated lytic enzyme(s), truncated lytic polypeptides, variant lytic polypeptide(s), and chimeric and/or shuffled lytic enzymes. Additionally, different lytic polypeptide(s) genetically coded for by different phage for treatment of the same bacteria may be used. These lytic enzymes may also be any combination of "unaltered" lytic enzymes or polypeptides, truncated lytic polypeptide(s), variant lytic polypeptide(s), and chimeric and shuffled lytic enzymes. The lytic enzyme(s)/polypeptide(s) in a therapeutic or pharmaceutical composition for gram-positive bacteria, including *Streptococcus, Staphylococcus, Enterococcus* and *Listeria*, may be used alone or in combination with antibiotics or, if there are other invasive bacterial organisms to be treated, in combination with other phage associated lytic enzymes specific for other bacteria being targeted. The lytic enzyme, truncated enzyme, variant enzyme, chimeric enzyme, and/or shuffled lytic enzyme may be used in conjunction with a holin protein. The amount of the holin protein may also be varied. Various antibiotics may be optionally included in the therapeutic composition with the enzyme(s) or polypeptide(s) and with or without the presence of lysostaphin. More than one lytic enzyme or polypeptide may be included in the therapeutic composition.

The pharmaceutical composition can also include one or more altered lytic enzymes, including isozymes, analogs, or variants thereof, produced by chemical synthesis or DNA recombinant techniques. In particular, altered lytic protein can be produced by amino acid substitution, deletion, truncation, chimerization, shuffling, or combinations thereof. The pharmaceutical composition may contain a combination of one or more natural lytic protein and one or more truncated, variant, chimeric or shuffled lytic protein. The pharmaceutical composition may also contain a peptide or a peptide fragment of at least one lytic protein derived from the same or different bacteria species, with an optional addition of one or more complementary agent, and a pharmaceutically acceptable carrier or diluent.

The pharmaceutical compositions of the present invention contain a complementary agent—one or more conventional antibiotics—particularly as provided herein. Antibiotics can be subgrouped broadly into those affecting cell wall peptidoglycan biosynthesis and those affecting DNA or protein synthesis in gram positive bacteria. Cell wall synthesis inhibitors, including penicillin and antibiotics like it, disrupt the rigid outer cell wall so that the relatively unsupported cell swells and eventually ruptures. The complementary agent may be an antibiotic, such as erythromycin, clarithromycin, azithromycin, roxithromycin, other members of the macrolide family, penicilins, cephalosporins, and any combinations thereof in amounts which are effective to synergistically enhance the therapeutic effect of the lytic enzyme. Virtually any other antibiotic may be used with the altered and/or unaltered lytic enzyme. Antibiotics affecting cell wall peptidoglycan biosynthesis include: Glycopeptides, which inhibit peptidoglycan synthesis by preventing the incorporation of N-acetylmuramic acid (NAM) and N-acetylglucosamine (NAG) peptide subunits into the peptidoglycan matrix. Available glycopeptides include vancomycin and teicoplanin; Penicillins, which act by inhibiting the formation of peptidoglycan cross-links. The functional group of penicillins, the β-lactam moiety, binds and inhibits DD-transpeptidase that links the peptidoglycan molecules in bacteria. Hydrolytic enzymes continue to break down the cell wall, causing cytolysis or death due to osmotic pressure. Common penicillins include oxacillin, ampicillin and cloxacillin; and Polypeptides, which interfere with the dephosphorylation of the $C_{55}$-isoprenyl pyrophosphate, a molecule that carries peptidoglycan building-blocks outside of the plasma membrane. A cell wall-impacting polypeptide is bacitracin. Other useful and relevant antibiotics include vancomycin, linezolid, and daptomycin.

Other lytic enzymes may be included in the carrier to treat other bacterial infections. The pharmaceutical composition can also contain a peptide or a peptide fragment of at least one lytic protein, one holin protein, or at least one holin and one lytic protein, which lytic and holin proteins are each derived from the same or different bacteria species, with an optional addition of a complementary agents, and a suitable carrier or diluent.

Also provided are compositions containing nucleic acid molecules that, either alone or in combination with other nucleic acid molecules, are capable of expressing an effective amount of a lytic polypeptide(s) or a peptide fragment of a lytic polypeptide(s) in vivo. Cell cultures containing these nucleic acid molecules, polynucleotides, and vectors carrying and expressing these molecules in vitro or in vivo, are also provided.

Therapeutic or pharmaceutical compositions may comprise lytic polypeptide(s) and antibiotic(s) combined with a variety of carriers to treat the illnesses caused by the susceptible gram-positive bacteria. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; glycine; amino acids such as glutamic acid, aspartic acid, histidine, or arginine; monosaccharides, disaccharides, and other carbohydrates including cellulose or its derivatives, glucose, mannose, trehalose, or dextrins; chelating agents such as EDTA; sugar alcohols such as mannitol or sorbitol; counter-ions such as sodium; non-ionic surfactants such as polysorbates, poloxamers, or polyethylene glycol (PEG); and/or neutral salts. Glycerin or glycerol (1,2,3-propanetriol) is commercially available for pharmaceutical use. DMSO is an aprotic solvent with a remarkable ability to enhance penetration of many locally applied drugs. The carrier vehicle may also include Ringer's solution, a buffered solution, and dextrose solution, particularly when an intravenous solution is prepared.

The effective dosage rates or amounts of an altered or unaltered lytic enzyme/polypeptide(s) of and for use in the present invention will depend in part on whether the lytic enzyme/polypeptide(s) will be used therapeutically or prophylactically, the duration of exposure of the recipient to the infectious bacteria, the size and weight of the individual, etc. The duration for use of the composition containing the enzyme/polypeptide(s) also depends on whether the use is for prophylactic purposes, wherein the use may be hourly, daily or weekly, for a short time period, or whether the use will be for therapeutic purposes wherein a more intensive regimen of the use of the composition may be needed, such that usage may last for hours, days or weeks, and/or on a daily basis, or at timed intervals during the day. Any dosage form employed should provide for a minimum number of units for a minimum amount of time. Carriers that are classified as "long" or "slow" release carriers (such as, for example, certain nasal sprays or lozenges) could possess or provide a lower concentration of active (enzyme) units per ml, but over a longer period of time, whereas a "short" or "fast" release carrier (such as, for example, a gargle) could possess or provide a high concentration of active (enzyme) units per ml, but over a shorter period of time. The amount of active units per ml and the duration of time of exposure depend on the nature of infection, whether treatment is to be prophylactic or therapeutic, and other variables. There are situations where it may be necessary to have a much higher unit/ml dosage or a lower unit/ml dosage.

The lytic enzyme/polypeptide(s) should be in an environment having a pH which allows for activity of the lytic enzyme/polypeptide(s). A stabilizing buffer may allow for the optimum activity of the lysin enzyme/polypeptide(s). The buffer may contain a reducing reagent, such as dithiothreitol or beta mercaptoethanol (BME). The stabilizing buffer may also be or include a metal chelating reagent, such as ethylenediaminetetracetic acid disodium salt, or it may also contain a phosphate or citrate-phosphate buffer, or any other buffer.

It is notable that the environment and certain aspects of the treatment location can affect the effectiveness of an antibiotic. For instance, daptomycin binds avidly to pulmonary surfactant and therefore is not effective in treatment of bacterial pneumonia, including staphylococcal pneumonia.

The present invention demonstrates the remarkable effectiveness and synergy of PlySs2 and daptomycin in combination against susceptible bacteria. In addition, PlySs2 lysin and daptomycin in combination remain very effective in the presence of a commercially available surfactant which mimics pulmonary surfactant. Thus, PlySs2 facilitates and enhances the effectiveness of antibiotic, particularly daptomycin, and serves to enable daptomycin effectiveness and activity even in the presence of surfactant.

A mild surfactant can be included in a therapeutic or pharmaceutical composition in an amount effective to potentiate the therapeutic effect of the lytic enzyme/polypeptide(s) may be used in a composition. Suitable mild surfactants include, inter alia, esters of polyoxyethylene sorbitan and fatty acids (Tween series), octylphenoxy polyethoxy ethanol (Triton-X series), n-Octyl-.beta.-D-glucopyranoside, n-Octyl-.beta.-D-thioglucopyranoside, n-Decyl-.beta.-D-glucopyranoside, n-Dodecyl-.beta.-D-glucopyranoside, and biologically occurring surfactants, e.g., fatty acids, glycerides, monoglycerides, deoxycholate and esters of deoxycholate.

Preservatives may also be used in this invention and preferably comprise about 0.05% to 0.5% by weight of the total composition. The use of preservatives assures that if the product is microbially contaminated, the formulation will prevent or diminish microorganism growth. Some preservatives useful in this invention include methylparaben, propylparaben, butylparaben, chloroxylenol, sodium benzoate, DMDM Hydantoin, 3-Iodo-2-Propylbutyl carbamate, potassium sorbate, chlorhexidine digluconate, or a combination thereof.

The therapeutic composition may further comprise other enzymes, such as the enzyme lysostaphin for the treatment of any *Staphylococcus aureus* bacteria present along with the susceptible gram-positive bacteria. Lysostaphin, a gene product of *Staphylococcus simulans*, exerts a bacteriostatic and bactericidal effect upon *S. aureus* by enzymatically degrading the polyglycine crosslinks of the cell wall (Browder et al., Res. Comm., 19: 393-400 (1965)). The gene for lysostaphin has subsequently been cloned and sequenced (Recsei et al., Proc. Natl. Acad. Sci. USA, 84: 1127-1131 (1987). A therapeutic composition may also include mutanolysin, and lysozyme.

Means of application of the therapeutic composition comprising a lytic enzyme/polypeptide(s) and antibiotic(s) include, but are not limited to direct, indirect, carrier and special means or any combination of means. Direct application of the lytic enzyme/polypeptide(s) may be by any suitable means to directly bring the polypeptide in contact with the site of infection or bacterial colonization, such as to the nasal area (for example nasal sprays), dermal or skin applications (for example topical ointments or formulations), suppositories, tampon applications, etc. Nasal applications include for instance nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal nares, or the face or any combination of these and similar methods of application. The forms in which the lytic enzyme may be administered include but are not limited to lozenges, troches, candies, injectants, chewing gums, tablets, powders, sprays, liquids, ointments, and aerosols.

The mode of application for the lytic enzyme and antibiotic includes a number of different types and combinations of carriers which include, but are not limited to an aqueous liquid, an alcohol base liquid, a water soluble gel, a lotion, an ointment, a nonaqueous liquid base, a mineral oil base, a blend of mineral oil and petrolatum, lanolin, liposomes, protein carriers such as serum albumin or gelatin, powdered cellulose carmel, and combinations thereof. A mode of delivery of the carrier containing the therapeutic agent includes, but is not limited to a smear, spray, a time-release patch, a liquid absorbed wipe, and combinations thereof. The lytic enzyme may be applied to a bandage either directly or in one of the other carriers. The bandages may be sold damp or dry, wherein the enzyme is in a lyophilized form on the bandage. This method of application is most effective for the treatment of infected skin. The carriers of topical compositions may comprise semi-solid and gel-like vehicles that include a polymer thickener, water, preservatives, active surfactants or emulsifiers, antioxidants, sun screens, and a solvent or mixed solvent system Polymer thickeners that may be used include those known to one skilled in the art, such as hydrophilic and hydroalcoholic gelling agents frequently used in the cosmetic and pharmaceutical industries. Other preferred gelling polymers include hydroxyethylcellulose, cellulose gum, MVE/MA decadiene crosspolymer, PVM/MA copolymer, or a combination thereof.

A composition comprising a lytic enzyme/polypeptide(s) and antibiotic(s) can be administered in the form of a candy, chewing gum, lozenge, troche, tablet, a powder, an aerosol, a liquid, a liquid spray, or toothpaste for the prevention or treatment of bacterial infections associated with upper respiratory tract illnesses. The lozenge, tablet, or gum into which the lytic enzyme/polypeptide(s) is added may contain sugar, corn syrup, a variety of dyes, non-sugar sweeteners, flavorings, any binders, or combinations thereof. Similarly, any gum-based products may contain acacia, carnauba wax, citric acid, cornstarch, food colorings, flavorings, non-sugar sweeteners, gelatin, glucose, glycerin, gum base, shellac, sodium saccharin, sugar, water, white wax, cellulose, other binders, and combinations thereof. Lozenges may further contain sucrose, cornstarch, acacia, gum tragacanth, anethole, linseed, oleoresin, mineral oil, and cellulose, other binders, and combinations thereof. Sugar substitutes can also be used in place of dextrose, sucrose, or other sugars. Compositions comprising lytic enzymes, or their peptide fragments can be directed to the mucosal lining, where, in residence, they kill colonizing disease bacteria. The mucosal lining, as disclosed and described herein, includes, for example, the upper and lower respiratory tract, eye, buccal cavity, nose, rectum, vagina, periodontal pocket, intestines and colon. Due to natural eliminating or cleansing mechanisms of mucosal tissues, conventional dosage forms are not retained at the application site for any significant length of time.

It may be advantageous to have materials which exhibit adhesion to mucosal tissues, to be administered with one or more phage enzymes and other complementary agents over a period of time. Materials having controlled release capability are particularly desirable, and the use of sustained release mucoadhesives has received a significant degree of attention. Other approaches involving mucoadhesives which are the combination of hydrophilic and hydrophobic materials, are known. Micelles and multilamillar micelles may also be used to control the release of enzyme. Materials having capacity to target or adhere to surfaces, such as plastic, membranes, devices utilized in clinical practice, including particularly any material or component which is placed in the body and susceptible to bacterial adhesion or biofilm development, such as catheters, valves, prosthetic devices, drug or compound pumps, stents, orthopedic materials, etc, may be combined, mixed, or fused to the lysin(s) of use in the present invention.

Therapeutic or pharmaceutical compositions of the invention can also contain polymeric mucoadhesives including a graft copolymer comprising a hydrophilic main chain and hydrophobic graft chains for controlled release of biologically active agents. The compositions of this application may optionally contain other polymeric materials, such as poly(acrylic acid), poly,-(vinyl pyrrolidone), and sodium carboxymethyl cellulose plasticizers, and other pharmaceutically acceptable excipients in amounts that do not cause deleterious effect upon mucoadhesivity of the composition.

A lytic enzyme/polypeptide(s) and antibiotic(s) of the invention may be administered for use in accordance with the invention by any pharmaceutically applicable or acceptable means including topically, orally or parenterally. For example, the lytic enzyme/polypeptide(s) can be administered intramuscularly, intrathecally, subdermally, subcutaneously, or intravenously to treat infections by gram-positive bacteria. In cases where parenteral injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. A vasoconstriction agent can be added to the formulation. The pharmaceutical preparations according to this application are provided sterile and pyrogen free.

For any compound, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. The exact dosage is chosen by the individual physician in view of the patient to be treated. Dosage and administration are adjusted to provide sufficient levels of the active moiety or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The effective dosage rates or amounts of the lytic enzyme/polypeptide(s) to be administered, and the duration of treatment will depend in part on the seriousness of the infection, the weight of the patient, particularly human, the duration of exposure of the recipient to the infectious bacteria, the number of square centimeters of skin or tissue which are infected, the depth of the infection, the seriousness of the infection, and a variety of a number of other variables. The composition may be applied anywhere from once to several times a day or a week, and may be applied for a short, such as days or up to several weeks, or long term period, such as many weeks or up to months. The usage may last for days or weeks. Any dosage form employed should provide for a minimum number of units for a minimum amount of time. The concentration of the active units of enzymes believed to provide for an effective amount or dosage of enzymes may be selected as appropriate.

The lysin and antibiotics of use and application in the compositions and methods of the invention may be administered simultaneously or subsequently. The lysin and antibiotic agents may be administered in a single dose or multiple doses, singly or in combination. The lysin and antibiotic may be administered by the same mode of administration or by different modes of administration, and may be administered once, twice or multiple times, one or more in combination or individually. Thus, lysin may be administered in an initial dose followed by a subsequent dose or doses, particularly depending on the response and bacterial killing or decolonization, and may be combined or alternated with antibiotic dose(s). In a particular aspect of the invention and in view of the reduction in the development of resistance to antibiotics by administering a lysin, particularly PlySs2, with antibiotic, combinations of antibiotic and lysin may be administered for longer periods and dosing can be extended without risk of resistance. In addition, in as much as the doses required for efficacy of each of antibiotic and lysin are significantly reduced by combining or co-administering the agents simultaneously or in series, a patient can be treated more aggressively and more continually without risk, or with reduced risk, of resistance.

The term 'agent' means any molecule, including polypeptides, antibodies, polynucleotides, chemical compounds and small molecules. In particular the term agent includes compounds such as test compounds, added additional compound(s), or lysin enzyme compounds.

The term 'agonist' refers to a ligand that stimulates the receptor the ligand binds to in the broadest sense.

The term 'assay' means any process used to measure a specific property of a compound. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Therapeutically effective amount' means that amount of a drug, compound, antimicrobial, antibody, polypeptide, or pharmaceutical agent that will elicit the biological or medical response of a subject that is being sought by a medical doctor or other clinician. In particular, with regard to gram-positive bacterial infections and growth of gram-positive bacteria, the term "effective amount" is intended to include an effective amount of a compound or agent that will bring about a biologically meaningful decrease in the amount of or extent of infection of gram-positive bacteria, including having a bacteriocidal and/or bacteriostatic effect. The phrase "therapeutically effective amount" is used herein to mean an amount sufficient to prevent, and preferably reduce by at least about 30 percent, more preferably by at least 50 percent, most preferably by at least 90 percent, a clinically significant change in the growth or amount of infectious bacteria, or other feature of pathology such as for example, elevated fever or white cell count as may attend its presence and activity.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

It is noted that in the context of treatment methods which are carried out in vivo or medical and clinical treatment methods in accordance with the present application and claims, the term subject, patient or individual is intended to refer to a human.

The terms "gram-positive bacteria", "Gram-positive bacteria", "gram-positive" and any variants not specifically listed, may be used herein interchangeably, and as used throughout the present application and claims refer to Gram-positive bacteria which are known and/or can be identified by the presence of certain cell wall and/or cell membrane characteristics and/or by staining with Gram stain. Gram positive bacteria are known and can readily be identified and may be selected from but are not limited to the genera *Listeria, Staphylococcus, Streptococcus, Enterococcus, Mycobacterium, Corynebacterium*, and *Clostridium*, and include any and all recognized or unrecognized species or strains thereof. In an aspect of the invention, the PlyS lysin sensitive gram-positive bacteria include bacteria selected from one or more of *Listeria, Staphylococcus, Streptococcus*, and *Enterococcus*.

The term "bacteriocidal" refers to capable of killing bacterial cells.

The term "bacteriostatic" refers to capable of inhibiting bacterial growth, including inhibiting growing bacterial cells.

The phrase "pharmaceutically acceptable" refers to molecular entities and compositions that are physiologically tolerable and do not typically produce an allergic or similar untoward reaction, such as gastric upset, dizziness and the like, when administered to a human.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

PlySs2 lysin demonstrates the ability to kill various strains of clinically significant gram-positive bacteria, including antibiotic resistant strains such as methicillin and vancomycin resistant and sensitive strains of *Staphylococcus aureus* (MRSA, MSSA, VRSA, VISA), daptomycin-resistant *Staphylococcus aureus* (DRSA), and linezolid-resistant *Staphylococcus aureus* (LRSA). PlySs2 is a unique lysin in having broad species killing activity and can kill multiple species of bacteria, particularly gram-positive bacteria, including *Staphylococcus, Streptococcus, Enterococcus* and *Listeria* bacterial strains. A tabulation of sensitivity (as depicted using MIC values and uM concentrations) of staphylococci to PlySs2 lysin and various antibiotics is shown in TABLE 2. Minimally inhibitory concentration (MICs) were determined using the broth microdilution method in accordance with standards and as described in the Clinical and Laboratory Standards Institute (CLSI) document M07-A9 (Methods for dilutional antimicrobial sensitivity tests for bacteria that grow aerobically. Volume 32 (Wayne [PA]: Clinical and Laboratory Standards Institute [US], 2012). This value is the MIC determined in the presence of reducing agent (such as DTT or BMS) in the MIC assay. Reducing agent is added for the purpose of improving reproducibility between and among assays in determining MIC values.

TABLE 2

PlySs2 and antibiotic activity against *S. aureus* strains

| Organisms | PlySs2 | | Daptomycin | | Vancomycin | | Oxacillin | | Linezolid | |
|---|---|---|---|---|---|---|---|---|---|---|
| (# of strains) | MIC$_{90}$ | [µM] | MIC$_{90}$ | [µM] | MIC$_{90}$ | [µM] | MIC$_{50/90}$ | [µM] | MIC$_{50/90}$ | [µM] |
| MRSA (n = 45) | 4 | 0.15 | 1 | 0.6 | 1 | 0.7 | >4* | >10.0* | 2 | 5.7 |
| MSSA (n - 28) | 4 | 0.15 | 1 | 0.6 | 1 | 0.7 | n/a | n/a | 2 | 5.7 |
| VISA (n = 10) | 32 | 1.2 | 8* | 4.9* | 4* | 2.7* | n/a | n/a | 2 | 5.7 |
| VRSA (n = 14) | 2 | 0.08 | 1 | 0.6 | >16* | >10.6* | n/a | n/a | 2 | 5.7 |
| LRSA (n = 5) | 2 | 0.08 | 1 | 0.6 | 1 | 0.7 | n/a | n/a | >64* | >183* |
| DRSA (n = 8) | 4 | 0.15 | 16* | 9.9* | 1 | 0.7 | n/a | n/a | 2 | 5.7 |

*MICs were determined using the broth microdilution method and evaluating 80% growth inhibition according to CLSI methods (M07-A9).

*Red Bold = drug failure (MIC value is above EUCAST breakpoint for the indicated drug on *S. aureus*)

Activity of PlySs2 against various gram-positive and gram-negative organisms is tabulated in TABLE 3, which includes MIC values and range for the different organisms. Activity of PlySs2 against antibiotic-resistant *Staphylococcus aureus* is provided in TABLE 4. PlySs2 has potent growth inhibitory activity on all *Staphylococcus aureus* strains tested including 103 MSSA and 120 MRSA isolates (MIC=8 µg/mL) as well as Groups A and B streptococci and *Staphylococcus lugdiensis* (TABLE 3). Little or no activity was observed on a collection of other Gram positive bacteria as well as all Gram negative bacteria tested. Although PlySs2 effectively kills antibiotic resistant and sensitive *S. aureus* as well as numerous other clinically significant gram-positive bacteria, it is notably ineffective on numerous commensal bacteria, such as *Escherichia coli*, as shown above in TABLE 1 and in TABLE 5 below which provides sensitivity of human gut bacteria and PlySs2 MIC.

TABLE 3

Activity of PlySs2 Against Gram-Positive and Gram-Negative Organisms

| Organism and susceptibility subset | MIC (µg/mL) | | |
|---|---|---|---|
| (no. tested) | 50% | 90% | Range |
| *Staphylcoccus aureus* | | | |
| Methicillin susceptible (103) | 4 | 8 | 1-16 |
| Methicillin resistant (120) | 4 | 8 | 1-16 |
| *Streptococcus pyogenes*, Group A (54) | 2 | 8 | 0.5-8 |
| *Streptococcus agalactiae*, Group B (51) | 8 | 16 | 1-64 |
| Other Gram-positive organisms | | | |
| *Staphylococcus lugdiensis* (10) | 8 | 8 | 8 |
| *Staphylococcus epidermidis* (11) | 128 | 512 | 4-512 |
| *Streptococcus pneumoniae* (26) | 16 | 64 | 1-64 |
| *Streptococcus mutans* (12) | 64 | 256 | 2-256 |
| *Listeria monocytogenes* (12) | 128 | 512 | 1-512 |
| *Enterococcus faecalis* (17) | >512 | >512 | 32->512 |
| *Enterococcus faecium* (5) | >512 | >512 | 32->512 |
| *Bacillus cereus* (10) | >512 | >512 | >512 |
| Gram-negative organisms | | | |
| *Acinetobacter baumannii* (8) | >512 | >512 | >512 |
| *Escherichia coli* (6) | >512 | >512 | >512 |
| *Pseudomonas aeruginosa* (5) | >512 | >512 | >512 |

TABLE 4

Activity of PlySs2 Against Antibiotic-Resistant *Staphylococcus aureus*

| | MIC (mg/mL) | | |
|---|---|---|---|
| Susceptibility subset (no. tested) | 50% | 90% | Range |
| Vancomycin-resistant (14) | 2 | 4 | 1-4 |
| Vancomycin-intermediate (31) | 8 | 32 | 1-64 |
| Linezolid-resistant (5) | 2 | 2 | 2-4 |
| Daptomycin-resistant (8) | 2 | 4 | 2-4 |

TABLE 5

Sensitivity of Human Gut Bacteria to PlySs2

| Organism | N | CF-301 MIC (ug/ml) |
|---|---|---|
| *Salmonella enteriditis* | 1 | >512 |
| *Pseudomonas aeruginosa* | 11 | >512 |
| *Escherichia coli* | 10 | >512 |
| *Klebsiella* spp. | 8 | >512 |

TABLE 5-continued

Sensitivity of Human Gut Bacteria to PlySs2

| Organism | N | CF-301 MIC (ug/ml) |
|---|---|---|
| *Proteus mirabilis* | 2 | >512 |
| *Lactobacillus* spp. | 6 | >512 |
| *Lactococcus* spp. | 3 | >512 |

While PlySs2 is effective against many different clinically relevant bacteria, it retains the beneficial character of many lysins in lacking broad spectrum bacterial killing, therefore side effects such as intestinal flora disturbance seen with many antibiotics will be minimized. In addition, lysins have demonstrated a low probability of bacterial resistance. PlySs2's remarkably broad clinically relevant killing capability make it uniquely applicable to the clinical setting, including in instances where there is a fully uncharacterized or mixed bacterial infection.

*Staphylococcus aureus* is the causative agent of several serious infectious diseases and the emergence of antibiotic resistant *S. aureus* strains has resulted in significant treatment difficulties, intensifying the need for new antimicrobial agents. Currently, 40 to 60% of nosocomial infections of *S. aureus* are resistant to oxacillin (Massey R C et al (2006) Nat Rev Microbiol 4:953-958), and greater than 60% of the isolates are resistant to methicillin (Gill S R et al (2005) J Bacteriol 187:2426-2438). A number of new antimicrobial agents, such as linezolid, quinupristin-dalfopristin, daptomycin, telavancin, new glycopeptides, ceftaroline, and ceftobiprole, have been introduced or are under clinical development (Aksoy D Y and S Unal (2008) Clin Microbiol Infect 14:411-420). As an option, current antibiotics to which strains such as MRSA are resistant may be resurrected as viable candidates in the treatment of MRSA when used in combination with other agents, offering a new dimension of potential anti-infectives. The application and use of lysin in combination with antibiotic has potential to circumvent bacterial resistance by virtue of the very low probability of development of resistance to the lysin component.

Figure 2:
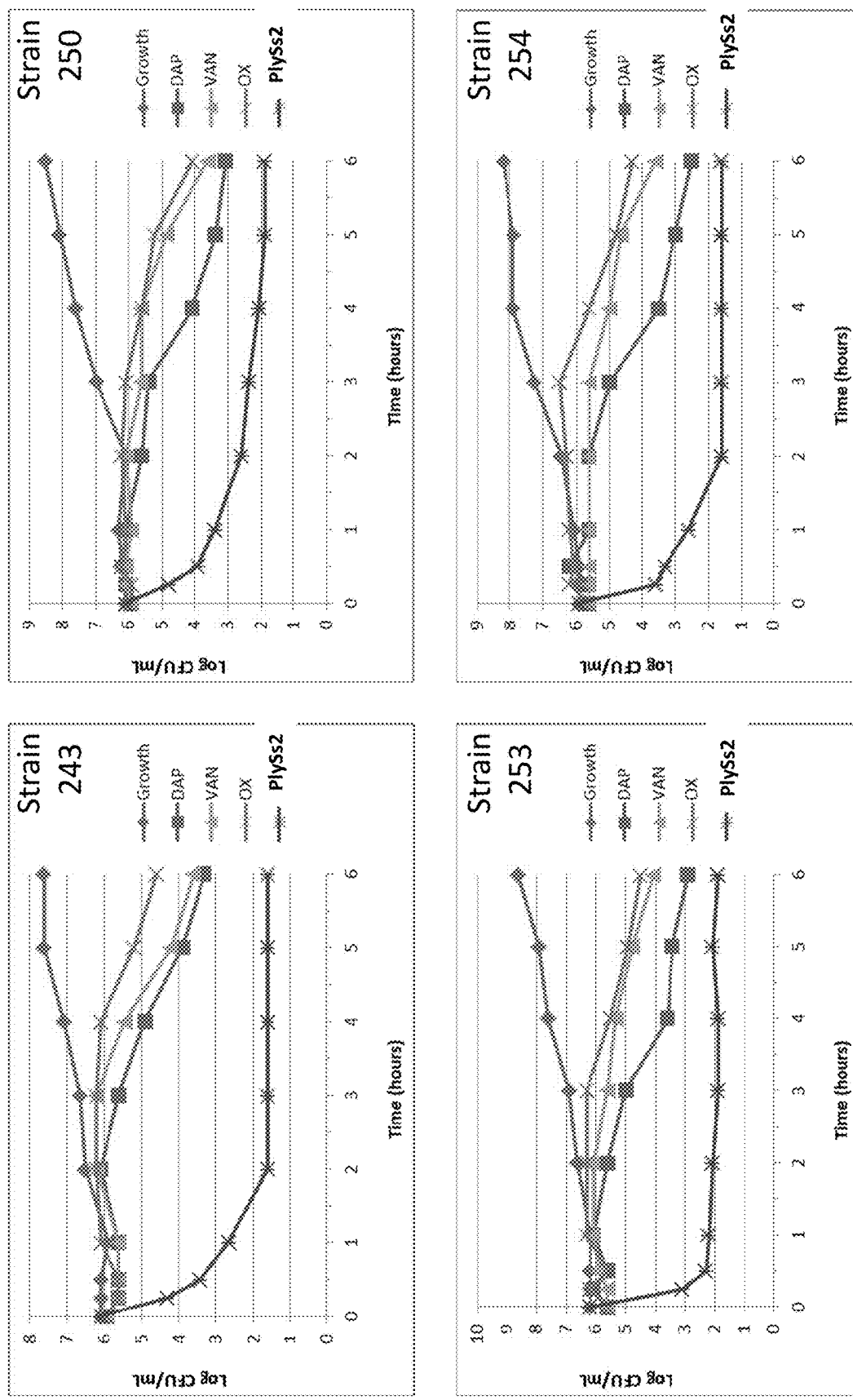
FIG. 2 depicts time kill curves of various MSSA strains in the presence of added daptomycin, vancomycin, oxacillin or PlySs2 lysin.
Figure 3:
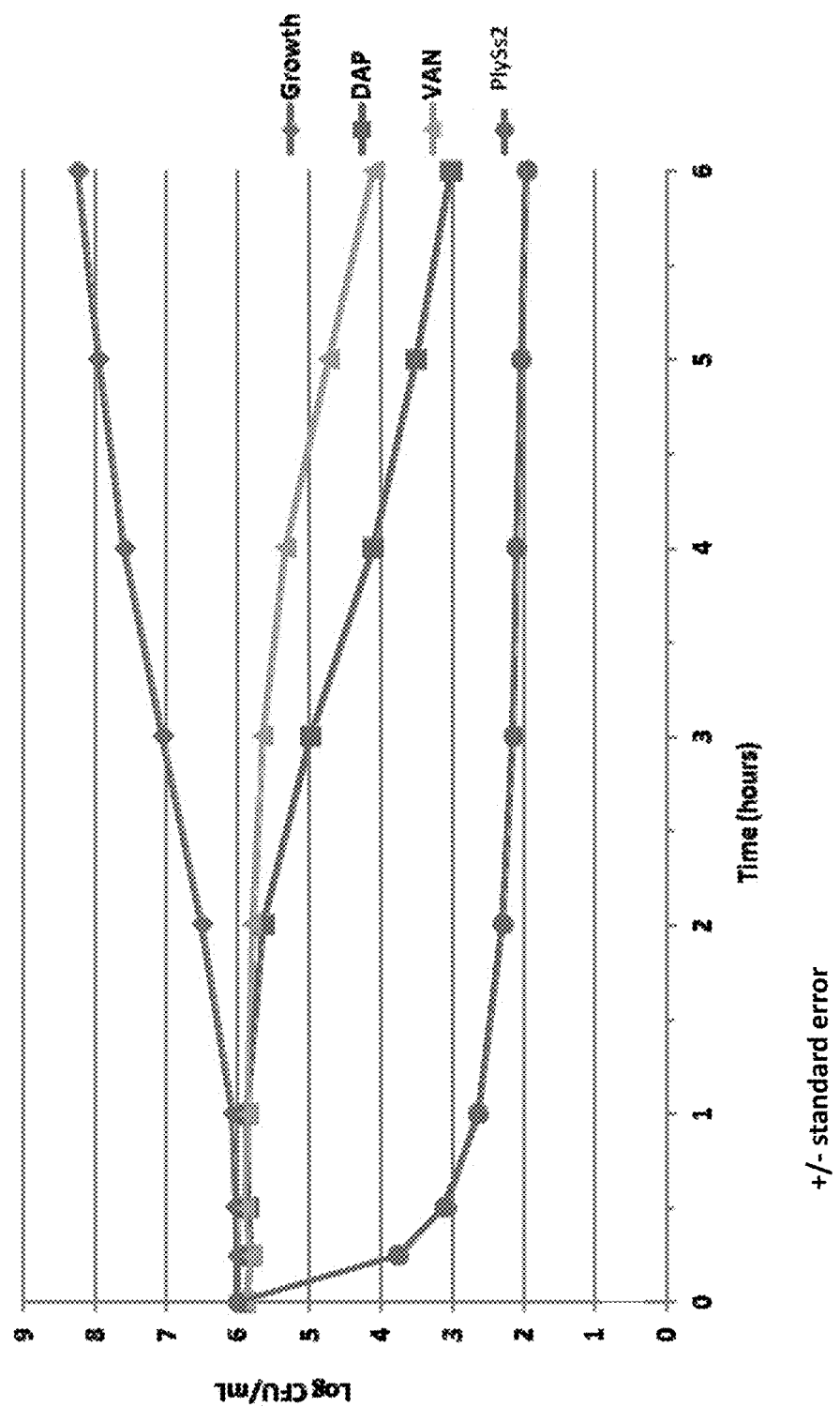
FIG. 3 provides a summary plot of time kill curves of various MRSA and MSSA strains in the presence of added daptomycin, vancomycin or PlySs2 lysin.

In order to more fully evaluate PlySs2's applicability to clinical Staphylococcal infections, time kill studies were undertaken against numerous *Staphylococcus aureus* strains, including methicillin resistant and methicillin sensitive strains. Time kill assays were performed according to CLSI methodology (CLSI document M07-A9 column 32 No. 2) on 42 methicillin resistant *S. aureus* (MRSA) strains and 20 methicillin sensitive *S. aureus* (MSSA) strains. Cultures of each strain ($5.5 \times 10^5$-$1 \times 10^6$ starting inoculum) were treated with PlySs2 lysin and with antibiotics daptomycin, oxacillin or vancomycin for comparison for 6 hours with aeration. MRSA and MSSA strains were treated with PlySs2, daptomycin and vancomycin. MSSA strains were also treated with oxacillin. 1× MIC concentrations of the different antibiotics were utilized, based on published and established antibiotic MIC values. PlySs2 lysin treatment was at approximately 1× MIC as previously determined (see TABLE 2 above). Culture aliquots were removed hourly up to 6 hours (time points taken at 15 and 30 min, 1 hr, 2 hr, 3 hr, 4 hr, 5 hr, and 6 hr) and added to a PBS/charcoal solution (to inactivate each drug), which was then serially diluted and plated for bacterial viability. The resulting log CFU/mL was plotted for each culture. Growth controls were included for each strain and represent bacterial growth in the absence of any antibacterial agent. Exemplary log kill curves for selected MRSA strains are depicted in FIG. 1. Exemplary log kill curves for selected MSSA strains are depicted in FIG. 2. A summary plot of the time kill studies with the MRSA and MSSA strains is shown in FIG. 3.

A listing of strains used in the studies provided herein, including cross-reference for recognized and available strain names is provided below in TABLE 6.

TABLE 6

Strain List

| Laboratory Designation (CFS #) | Strain Type | Common Strain Designation* |
|---|---|---|
| 223 | MRSA | BAA-1720 |
| 241 | MRSA | NRS100 |
| 243 | MSSA | NRS107 |
| 245 | MRSA | NRS070 |
| 250 | MSSA | NRS149 |
| 253 | MSSA | NRS155 |
| 254 | MSSA | NRS156 |
| 263 | MRSA | NRS387 |
| 269 | MRSA | NRS123 (MW2) |
| 270 | MRSA | NRS383 |
| 553 | MRSA | ATCC 43300 |
| 554 | MSSA | ATCC 25923 |
| 581 | MSSA | ATCC 29213 |
| 650 | MRSA | 052C |
| 738 | MRSA | NRS192 |
| 743 | MRSA | NRS255 |
| 832 | MRSA | NRS671 |
| 926 | MRSA | BK20781 |
| 927 | MRSA | W15 |

*NARSA ("NRS") and ATCC ("ATCC" and "BAA") strain designations are indicated where appropriate. Additional names reflect strain designations available in the literature.

PlySs2 has Rapid Kill Kinetics in vitro

Figure 4:
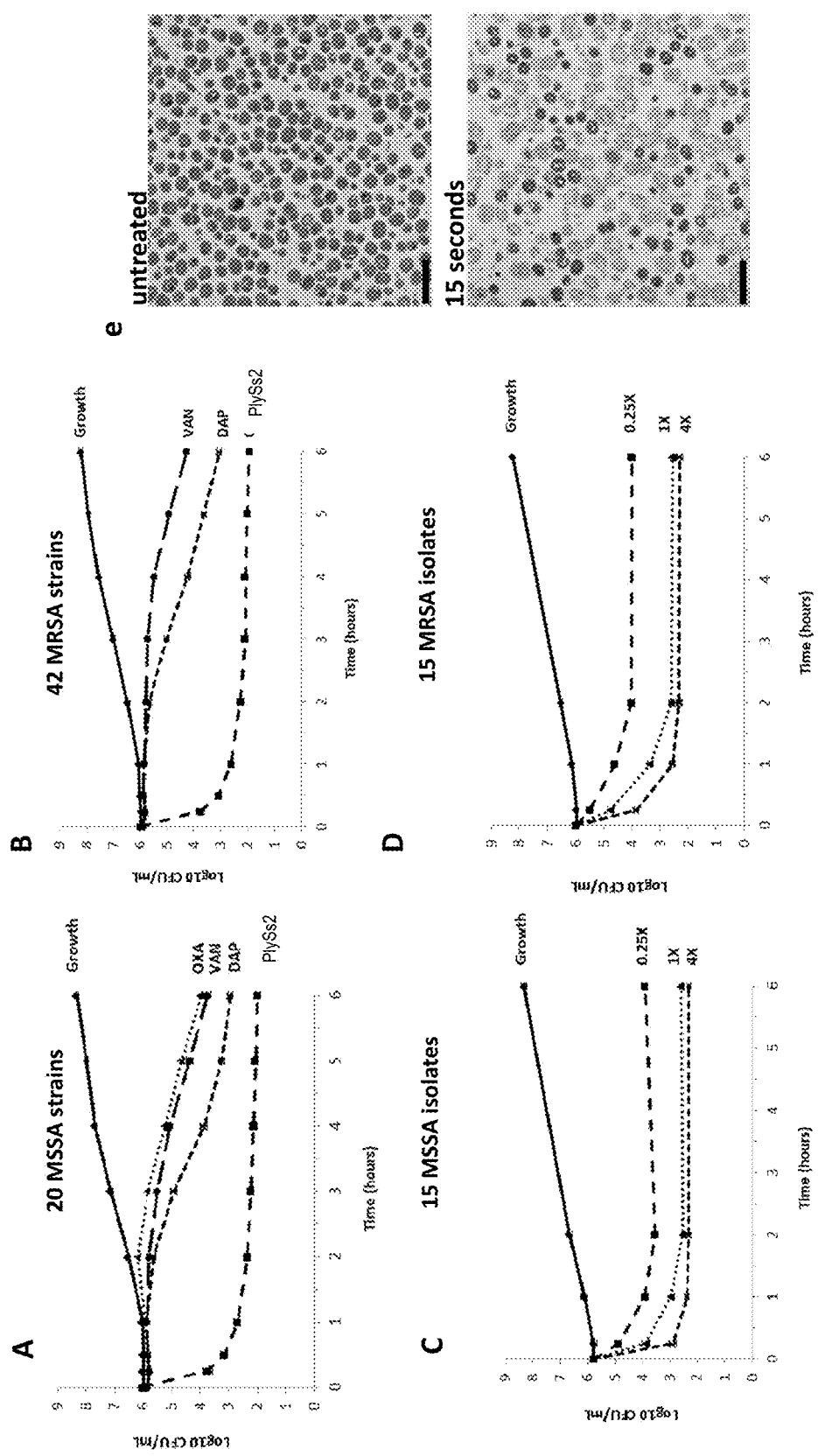
FIG. 4A-4F provides composite time kill curves of PlySS2 and antibiotics on *S. aureus* cells in vitro. (A, B) Composite time-kill curves of PlySS2 compared to oxacillin (OXA), vancomycin (VAN), and daptomycin (DAP) against sets of 20 MSSA and 42 MRSA strains, respectively. In each individual analysis, drug concentrations correspond to strain-specific 1× MIC values. Mean values (± standard error of the mean) are shown for each time-point. (C, D) Titration analysis of PlySS2 against sets of 15 contemporary clinical MSSA and MRSA isolates, respectively. In each individual analysis, PlySS2 concentrations correspond to strain-specific MIC values. 4×, 1×, and 0.25× MIC concentrations were used. (E,F) Transmission electron micrographs (3300× magnification) of *S. aureus* cells (strain MW2) before and after 3 second treatment with 8 g/mL PlySS2. Scale bars correspond to 2 µM. Lysis results in the loss of darkly stained cytoplasmic components.

Rapid-kill kinetics are desirable in the clinical setting to treat patients with fulminant bacterial infections. To test the rate of antimicrobial activity in vitro, we used time-kill assays (Mueller M et al (2004) Antimicrob Agents Chemotherapy 48:369-377) in which 1× MIC drug concentrations were tested across 20 different MSSA and 42 MRSA strains. PlySs2 reached bactericidal levels (Methods for dilution antimicrobial susceptibility tests for bacteria that grow aerobically. Vol. 32 (Wayne (Pa.): Clinical and Laboratory Standards Institute (U.S.), 2012) (≥3-$\log_{10}$ reduction in CFUs) within 30 minutes (FIGS. 4A and B). In contrast, daptomycin required 6 hours to reach bactericidal levels while vancomycin and oxacillin achieved only 2-$\log_{10}$ kill within 6 hours. Rapid-kill kinetics were also obtained for PlySs2 against sets of 15 different contemporary MSSA (FIG. 4C) or MRSA (FIG. 4D) isolates, illustrating the efficient bactericidal activity of PlySs2 on relevant clinical isolates. The potent activity of PlySs2 was further illustrated by electron microscopy showing extensive bacteriolysis of S. aureus cocci after only 15 seconds of treatment; the speed of PlySs2 action is consistent with a bactericidal effect immediately upon contact (FIG. 4E).

All MRSA and MSSA strains tested are killed rapidly with PlySs2, with maximal kill (ie, ≥3 log reduction) observed generally within the first hour of incubation with lysin and logs reduced to 1 log CFU/ml (the effective lower limit of the test) in most instances. Daptomycin or vancomycin reduce growth of most MRSA and MSSA strains by 2-3 logs observed generally over a few hours or more of incubation, with daptomycin being the most effective against most strains. Oxacillin was the least effective of the antibiotic agents against MSSA strains. In all instances, PlySs2 kill was greater and faster than any antibiotic.

The studies were expanded to include testing of various S. aureus strains, including vancomycin intermediate sensitive S. aureus (VISA), vancomycin resistant S. aureus (VRSA), linezolid resistant S. aureus (LRSA) and daptomycin resistant S. aureus (DRSA), with PlySs2 lysin, daptomycin, vancomycin and linezolid, using methods as described above. A tabulation of studies undertaken with MSSA, MRSA, VISA, VRSA, LRSA and DRSA strains of Staphylococcus aureus is provided in TABLE 2 above with minimal inhibitory concentrations (MICs) of PlySs2 and various antibodies provided for various strains.

Example 2

While PlySs2 lysin alone kills more rapidly than antibiotics alone, as shown above, no information regarding the capability or effectiveness of PlySs2 in combination with antibiotics is known or available. Bacterial kill studies were undertaken to assess combinations of PlySs2 lysin with antibiotic against Staphylococcus aureus in vitro.

Time kill assays were performed as described above on several MRSA strains with addition of PlySs2 or antibiotic alone or in combination at various concentrations. Cultures of each strain ($5.5 \times 10^5$-$1 \times 10^6$ starting inoculum) were treated with PlySs2 lysin, antibiotic (daptomycin or vancomycin), or combinations of PlySs2 and antibiotic for 6 hours with aeration. In each instance, sub-MIC doses of PlySs2 and of antibiotic were utilized in order to observe synergy and enhanced combination agent effectiveness. Growth controls were included for each strain and represent bacterial growth in the absence of any antibacterial agent. Time kill curves of two MRSA strains with addition of ½ MIC of PlySs2 and ¼ MIC of vancomycin are shown in FIG. 5. At these sub-MIC doses, vancomycin or PlySs2 are ineffective or poorly effective alone up to 6 hours. Combinations of ½ MIC of PlySs2 and ¼ MIC of vancomycin result in up to 4 logs of kill of MRSA in culture within 6 hours.

Figure 7:
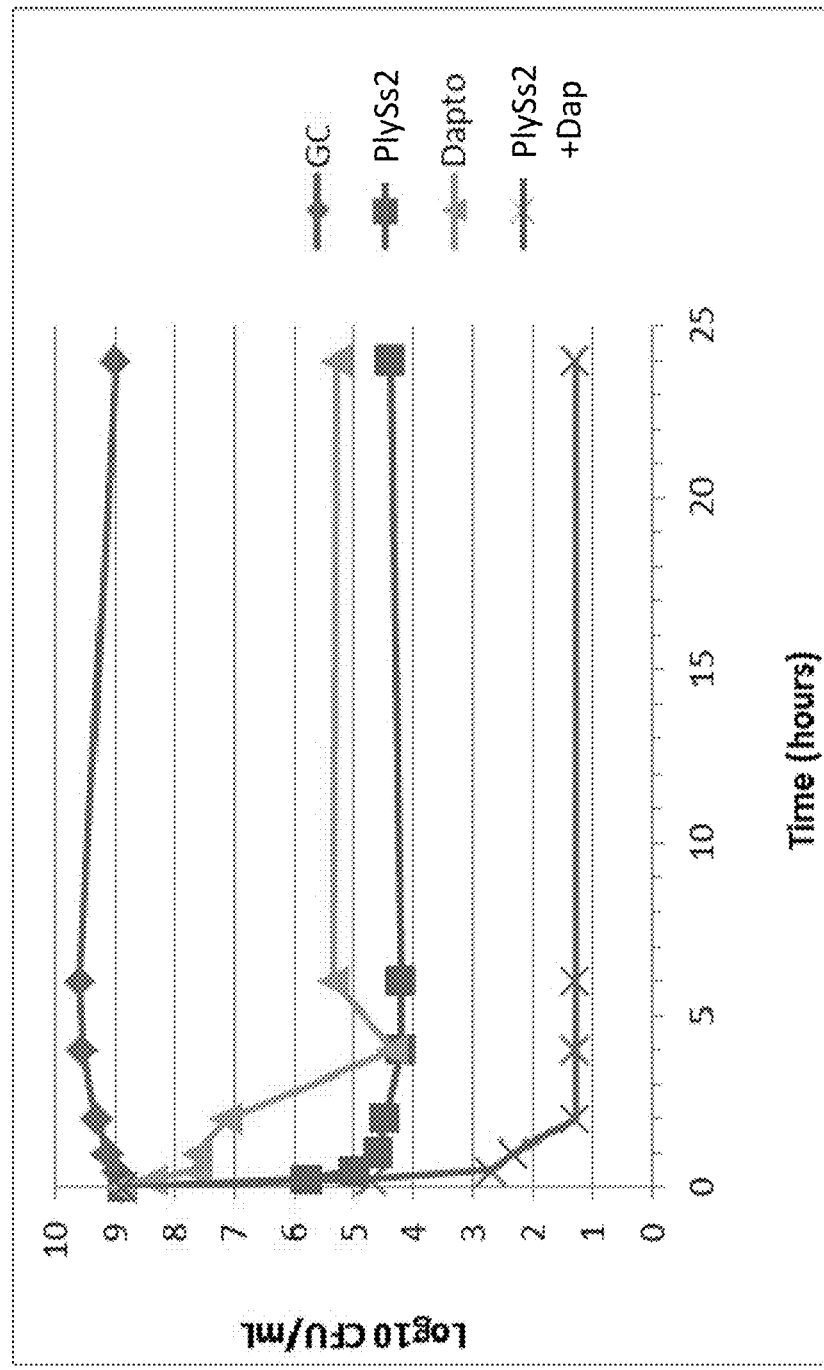
FIG. 7 depicts time kill curves for MRSA strain 650 (O52C Tomasz) in the presence of added daptomycin and PlySs2 lysin alone or in combination at the noted MIC or dose.
Figure 8A:
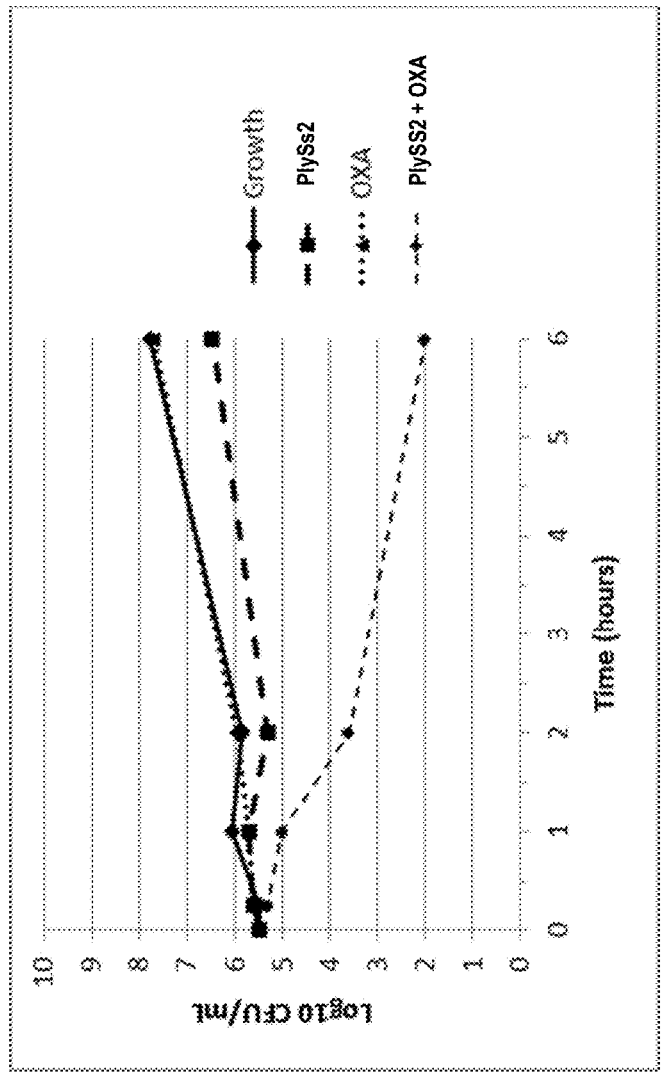
FIG. 8A-8F shows that PlySs2 synergizes with antibiotics across multiple strains in-vitro and depicts time-kill results for MSSA strains treated with PlySs2 and oxacillin (A,B); MRSA strains treated with Plyss2 and vancomycin (C,D), MRSA strains treated with PlySs2 and daptomycin (E,F). In panels A, C, and E time-kill data are shown for three individual strains, MSSA strain JMI 7140, MRSA strain JMI 3340 and MRSA strain JMI 3345 respectively. (A) Values are shown for growth, growth control (no PlySs2 or antibiotic), PlySs2 0.13× MIC, oxacillin (OXA) 0.5× MIC, PlySS2+Oxa combination of indicated drug concentrations. (C) Values are shown for growth, growth control (no PlySs2 or antibiotic), PlySs2 0.13× MIC, vancomycin (VAN) 0.5× MIC, PlySS2+VAN combination of indicated drug concentrations. (E) Values are shown for growth, growth control (no PlySs2 or antibiotic), PlySs2 0.25× MIC, daptomycin (DAP) 0.5× MIC, PlySS2+DAP combination of indicated drug concentrations. In panels B, D, and F the log change in cfu/ml between the combination-treated culture and the untreated growth control over 6 hours are shown for collections of strains. The horizontal dotted lines indicate the 2 log cutoff required for scoring time-kill synergy. Decreases in $\log_{10}$ colony counts (or $\Delta\text{Log}_{10}$ CFU/mL) are shown for cultures treated for 6 hours with drug combination, compared to cultures treated with the most active single agent. Synergy is defined by the CLSI as a $\geq 2\text{-}\log_{10}$ decrease in CFU/mL and is denoted in the figure by the dashed line. Key: $\Delta\text{Log}10$ CFU/mL=change in $\log_{10}$ colony-forming units.
Figure 8B:
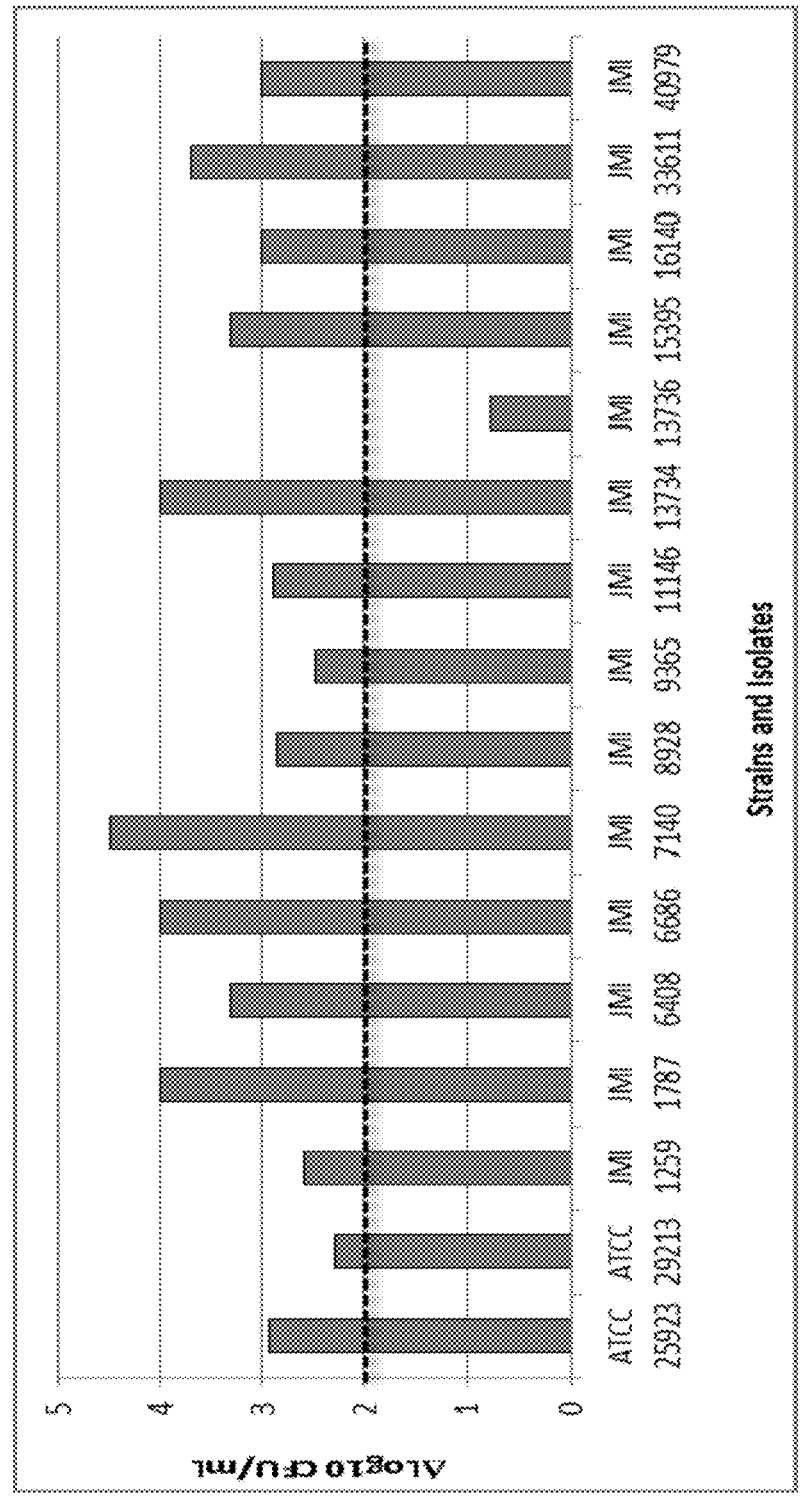
Figure 8C:
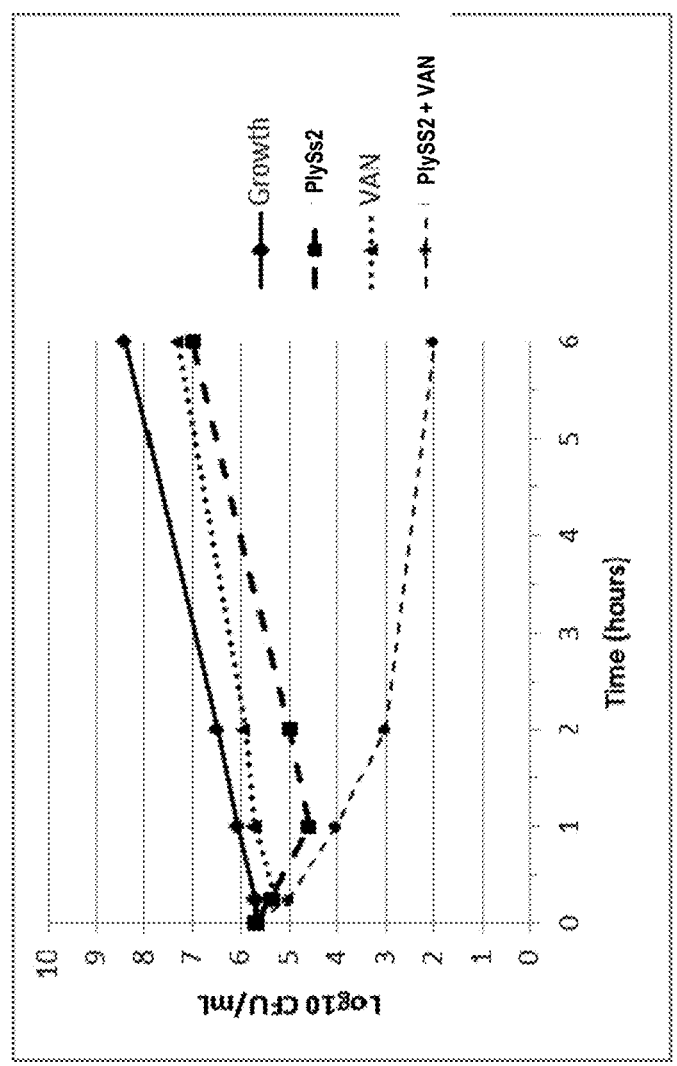
Figure 8D:
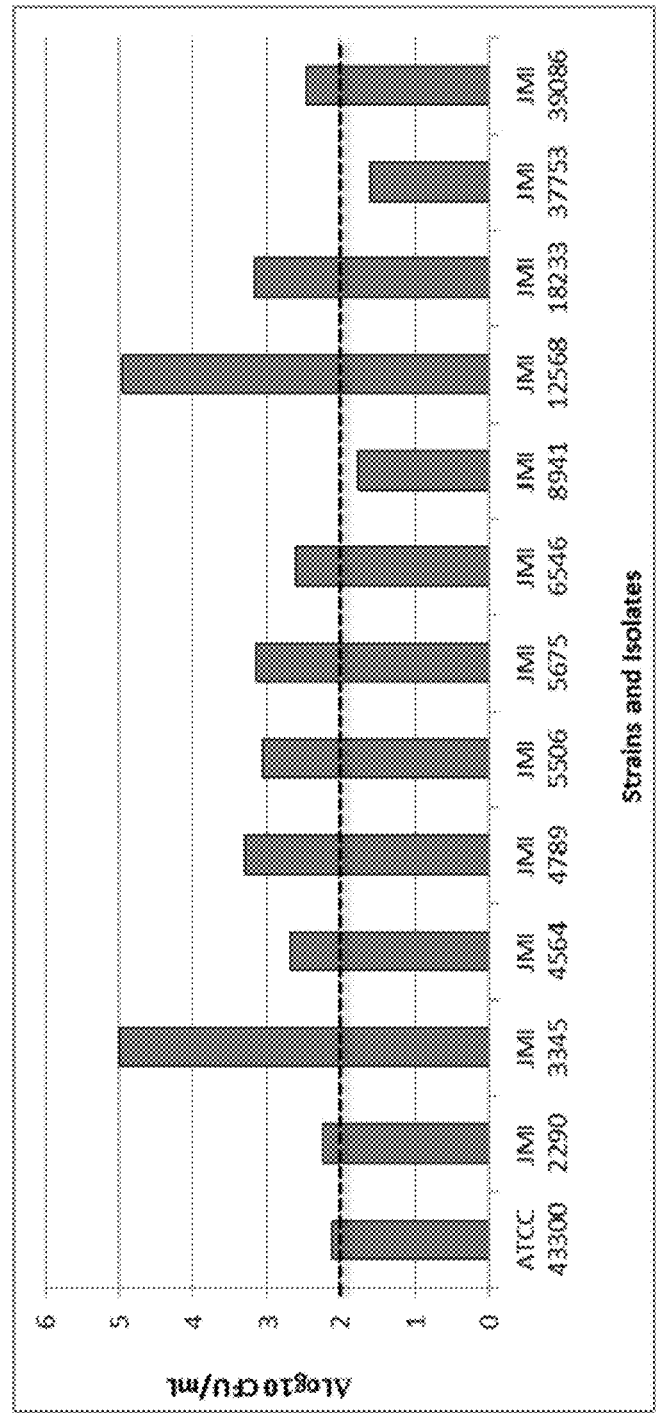
Figure 8E:
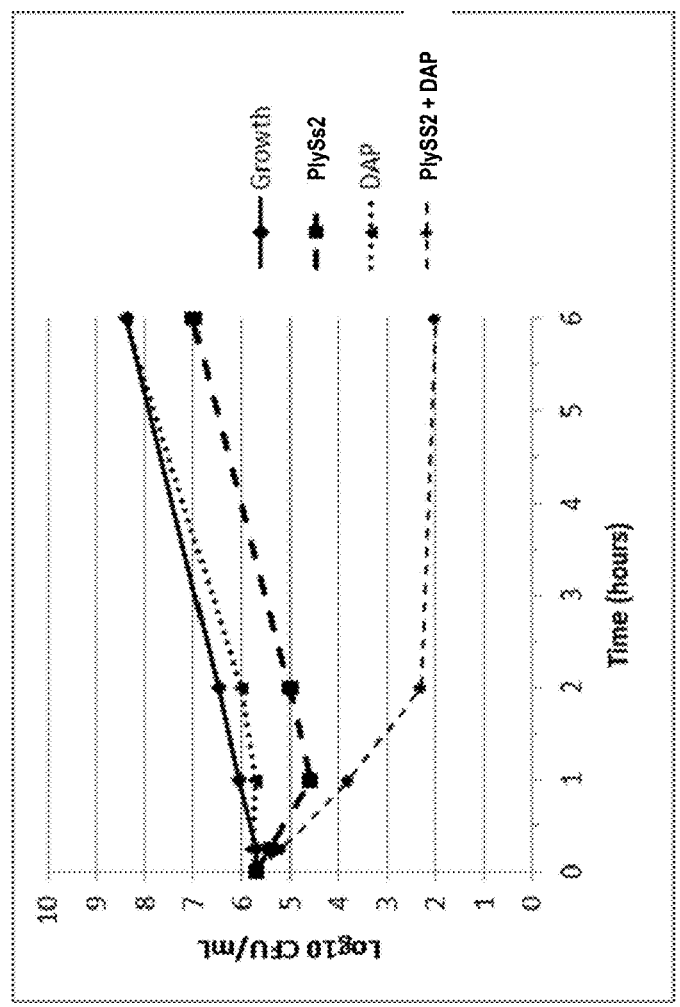
Figure 8F:
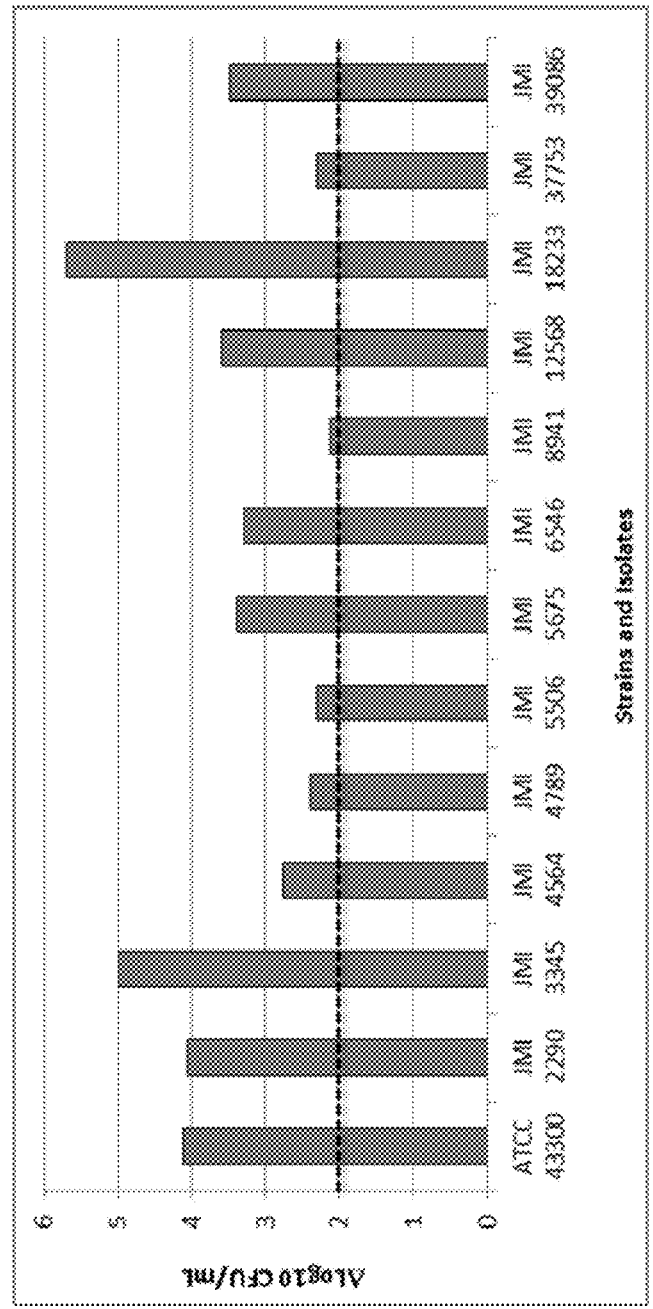
Figure 9:
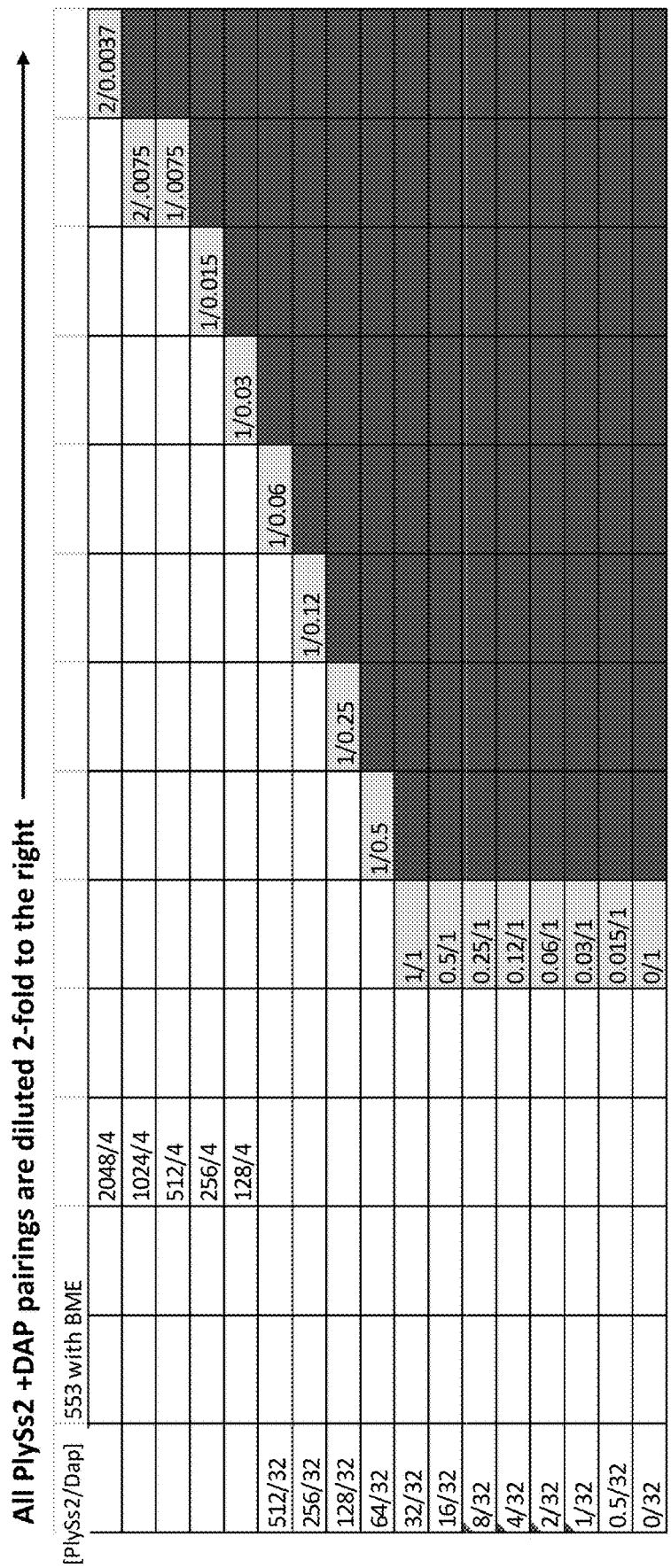
FIG. 9 provides a panel of dose dilutions of pairings of daptomycin and PlySs2 at the noted concentrations on MRSA strain 553 in the presence of reducing agent (BME).
Figure 10:
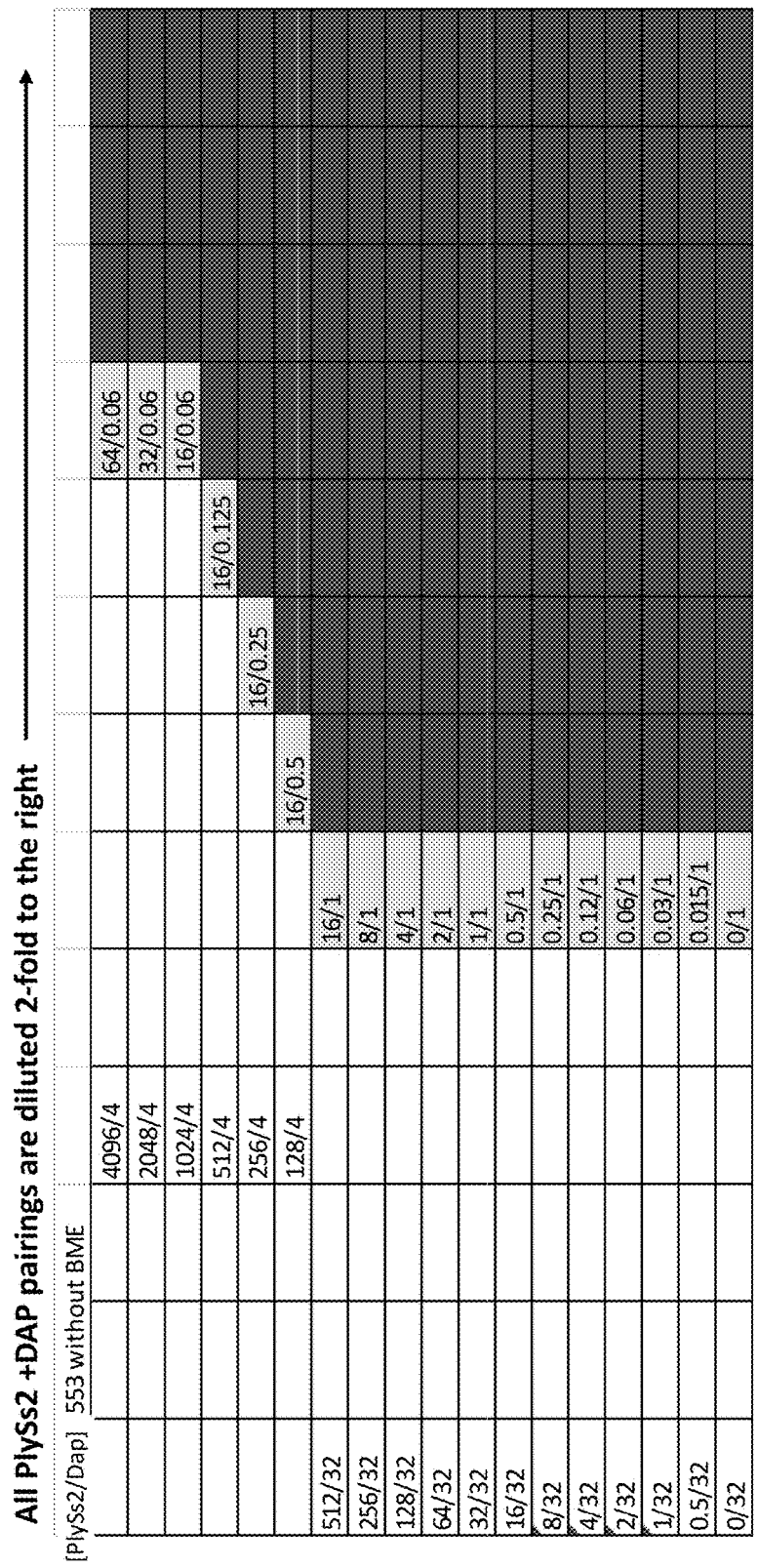
FIG. 10 provides a panel of dose dilutions of pairings of daptomycin and PlySs2 at the noted concentrations on MRSA strain 553 in the absence of reducing agent (BME).
Figure 11:
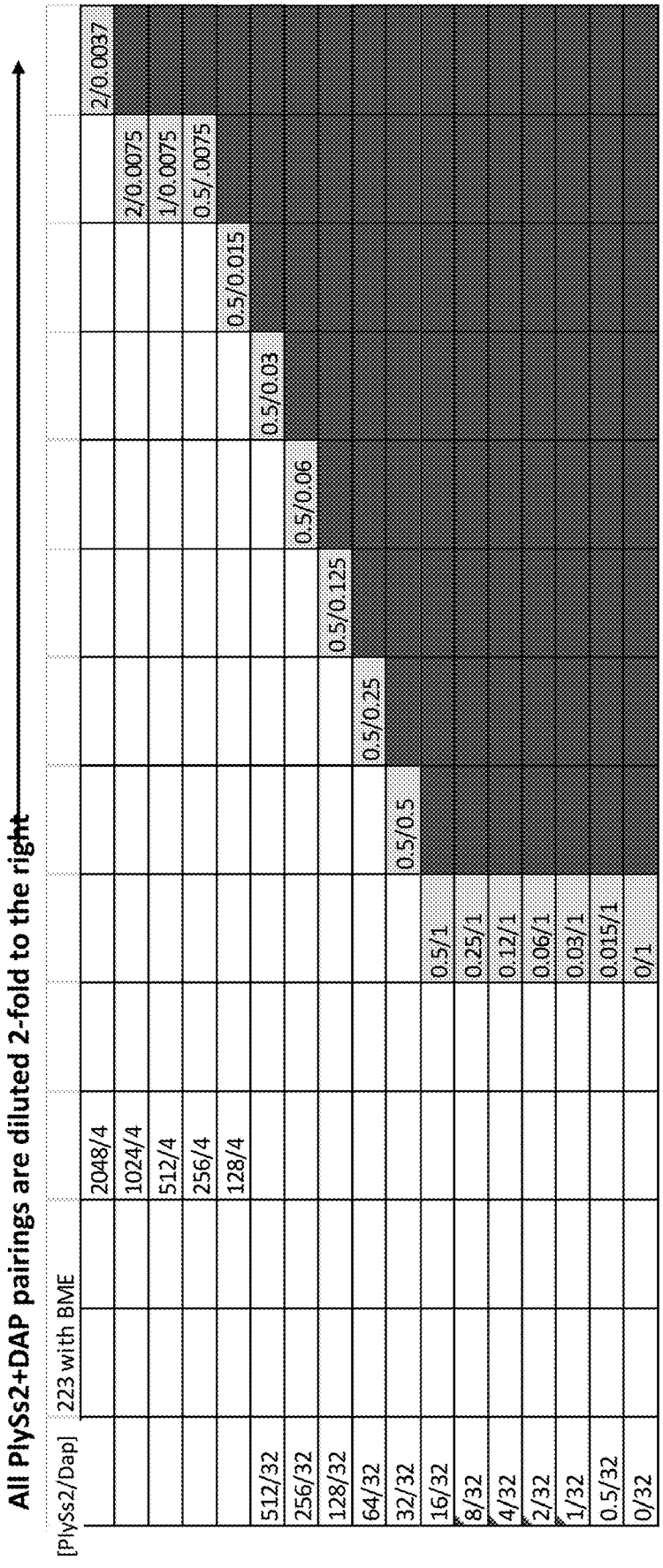
FIG. 11 provides a panel of dose dilutions of pairings of daptomycin and PlySs2 at the noted concentrations on MRSA strain 223 in the presence of BME.
Figure 12:
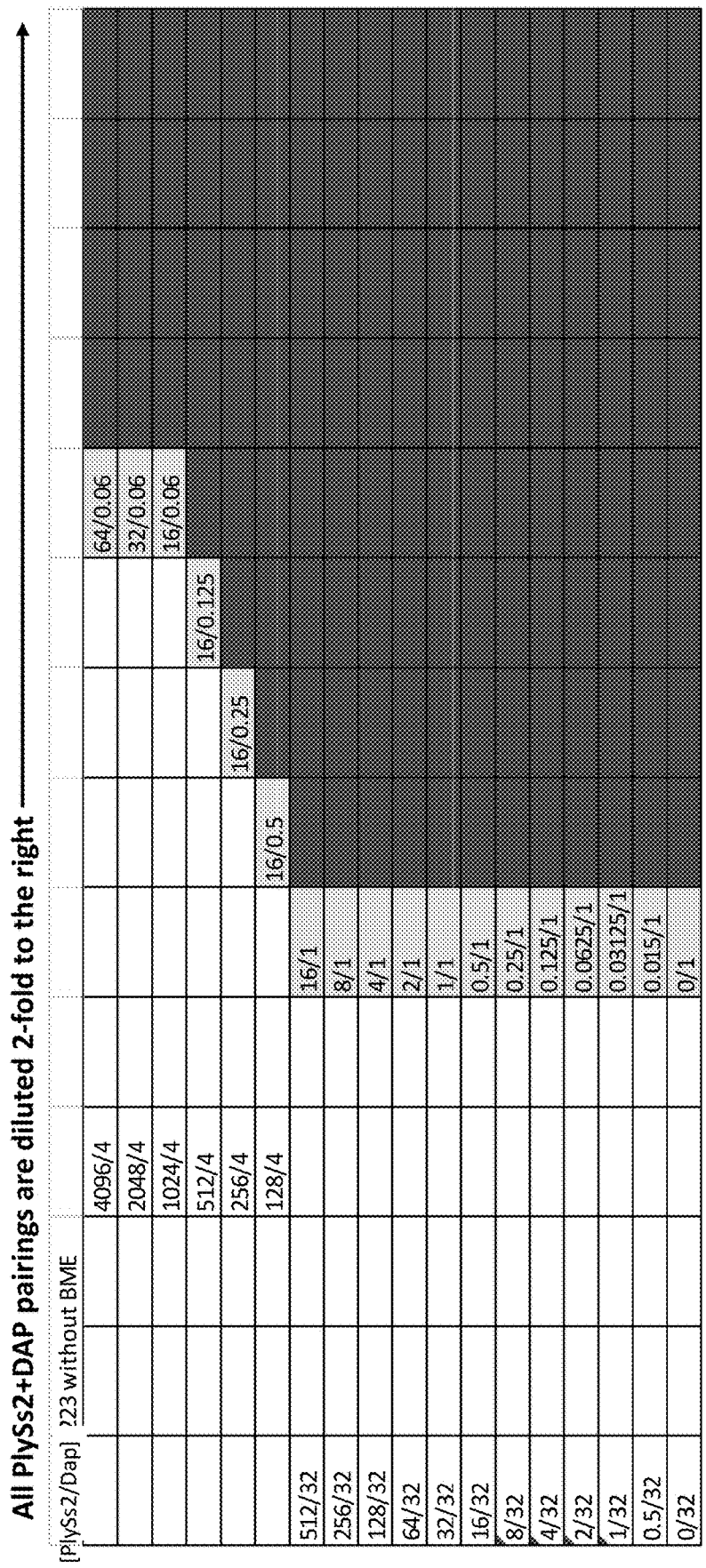
FIG. 12 provides a panel of dose dilutions of pairings of daptomycin and PlySs2 at the noted concentrations on MRSA strain 223 in the absence of BME.
Figure 14:
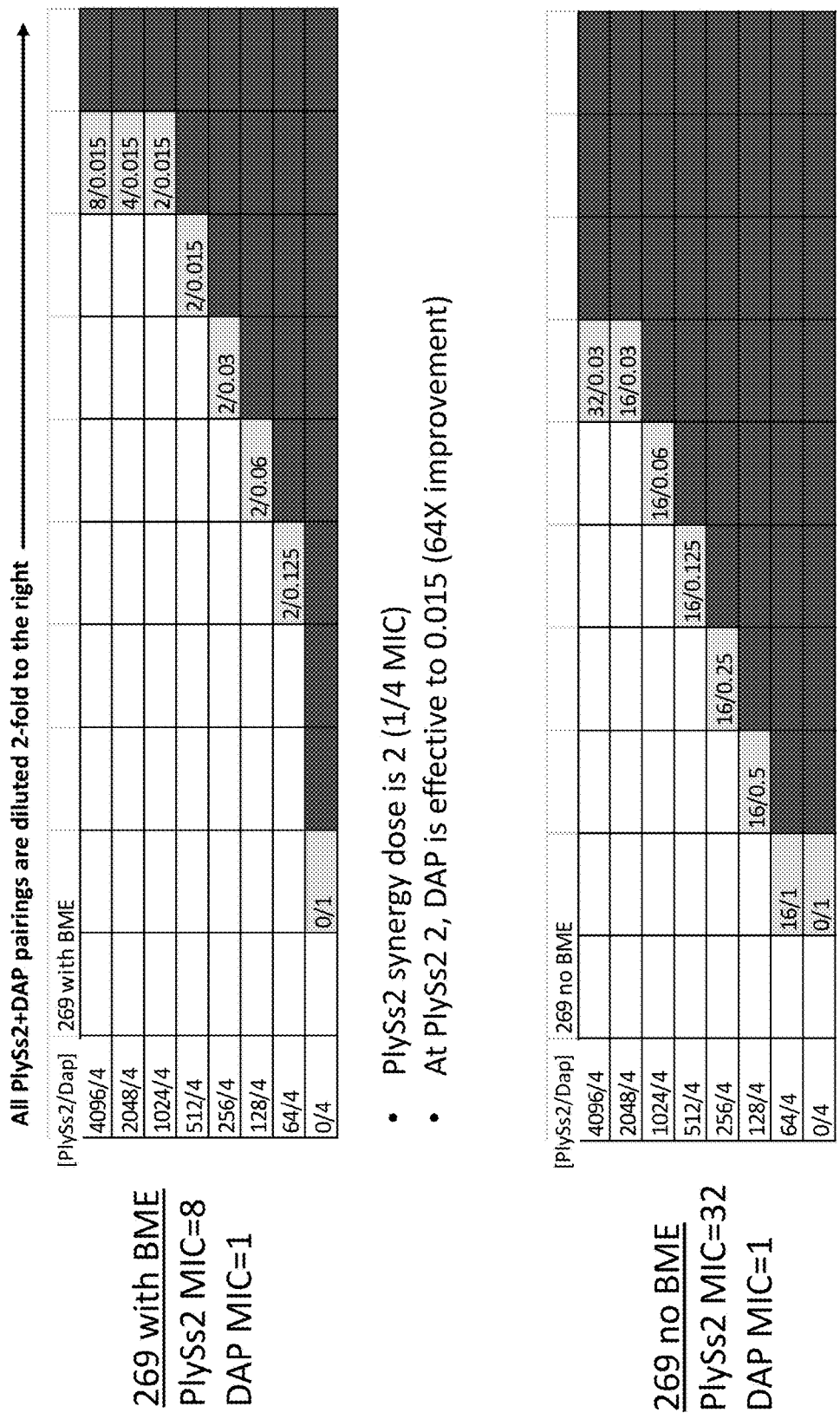
FIG. 14 provides a panel of dose dilutions of pairings of daptomycin and PlySs2 at the noted concentrations on MRSA strain 269 in the presence and absence of BME.
Figure 15:
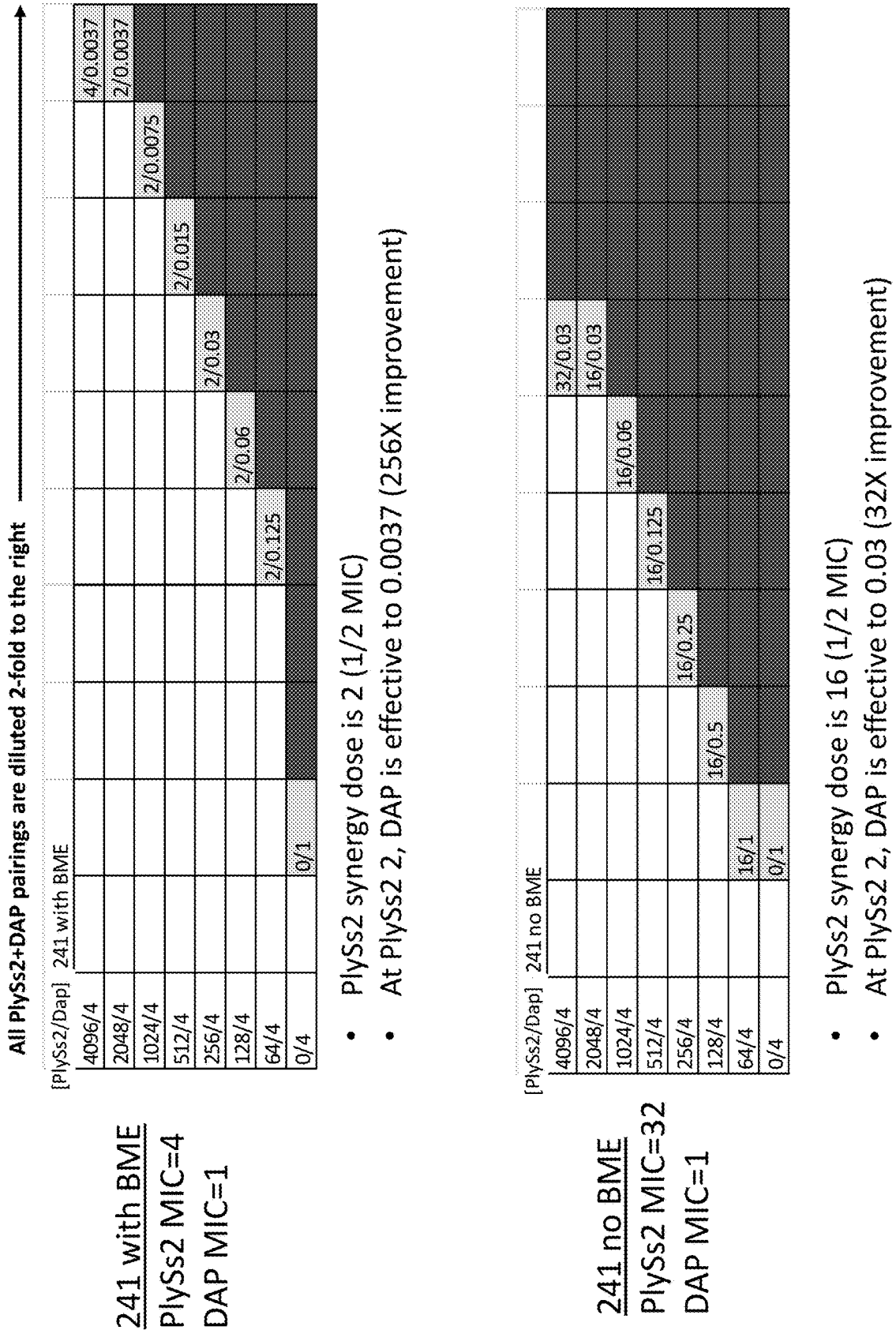
FIG. 15 provides a panel of dose dilutions of pairings of daptomycin and PlySs2 at the noted concentrations on MRSA strain 241 in the presence and absence of BME.
Figure 18:
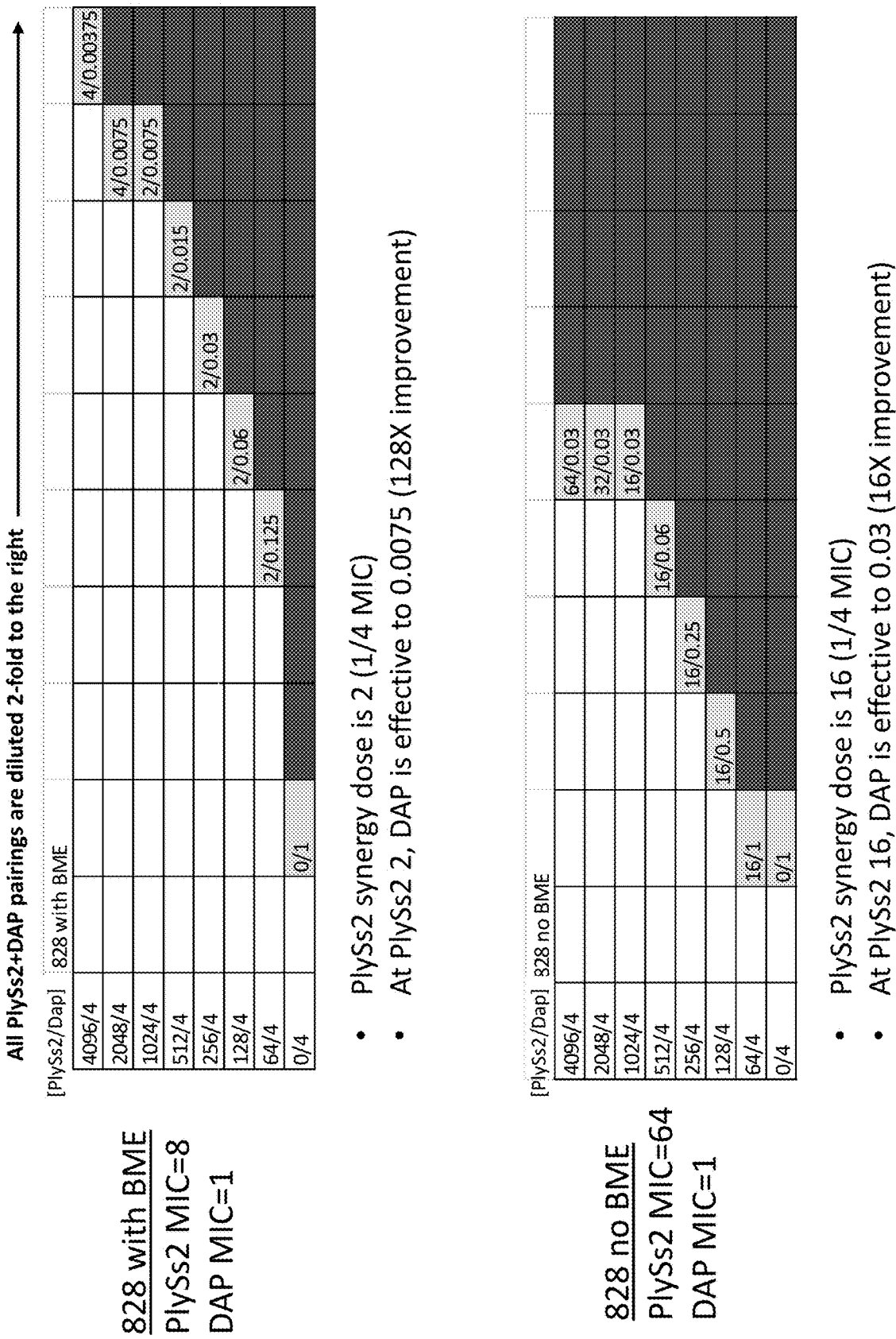
FIG. 18 provides a panel of dose dilutions of pairings of daptomycin and PlySs2 at the noted concentrations on MRSA strain 828 in the presence and absence of BME.

Log Kill curves of two MRSA strains with addition of ¼ MIC of PlySs2 and ⅛ MIC of daptomycin are shown in FIG. 6. Combinations of ¼ MIC of PlySs2 and ⅛ MIC of daptomycin result in approximately 4 logs of kill of MRSA in culture within 6 hours. FIG. 7 depicts another combination study based on 1× MIC values of PlySs2 and daptomycin on MRSA strain 650 (O52C Tomasz strain-$1 \times 10^9$ starting inoculum). PlySs2 lysin is added at 16 μg/ml, daptomycin is added at 1 μg/ml. While each single agent alone results in 4-5 log kill at the added concentrations, the combination of PlySs2 and daptomycin provides complete kill (log kill to the detection limit of the assay) within 2 hours.

Example 3

Combination therapy is particularly effective when drugs act synergistically (Cottarel G & Wierzbowski J (2007) Trends Biotechnology 25:547-555). Synergy assessment between PlySs2 and cell envelope-active antibiotics was performed by the time-kill assay, a preferred method for examining synergistic antimicrobial activity in vitro (Mueller M et al (2004) Antimicrob Agents and Chemotherapy 48:369-377; Methods for dilution antimicrobial susceptibility tests for bacteria that grow aerobically, Vol. 32 (Wayne (Pa.): Clinical and Laboratory Standards Institute (U.S.), 2012). Synergy studies were additionally evaluated with antibiotic oxacillin, which is a member of the penicillin family and kills bacteria in a distinct manner versus either of vancomycin or daptomycin. The results of oxacillin studies either alone or in the presence of lysin PlySs2 are shown in FIG. 8. Time-kill curves were generated using sub-MIC concentrations of PlySs2 daptomycin, vancomycin, and oxacillin either alone or in combinations against clinical MRSA (FIG. 8C-8F) or MSSA (FIG. 8A-8B) isolates. Synergy was defined as a ≥2-log10 decrease in CFU/mL at the 6 hour time-point for the combination compared to the most active single-agent. Based on this criteria, PlySs2 acted synergistically with all antibiotics evaluated against all representative MRSA and MSSA strains evaluated (see FIGS. 4-8). An expanded set of isolates were similarly examined and synergy was observed in 45 of 49 analyses for MSSA and 24 of 26 for MRSA with PlySs2 combined with distinct antibiotics, including oxacillin, vancomycin and daptomycin (TABLES 7-11 provided below).

TABLE 7

Synergy Time-Kill Results with Oxacillin (MSSA)

| Strains[1] | Optimal Synergistic Concentrations[2] | | $\Delta Log_{10}$ CFU/mL[3] | Interaction[4] |
|---|---|---|---|---|
| | [PlySs2] μg/mL (xMIC[5]) | [Oxacillin] μg/mL (xMIC) | | |
| ATCC 25923 | 4.0 (0.13) | 0.06 (0.5) | 2.9 | Synergy |
| ATCC 29213 | 1.0 (0.13) | 0.13 (0.5) | 2.3 | Synergy |
| JMI 1259 | 1.0 (0.13) | 0.13 (0.5) | 2.6 | Synergy |
| JMI 1787 | 0.5 (0.06) | 0.13 (0.5) | 4.0 | Synergy |
| JMI 6408 | 1.0 (0.13) | 0.10 (0.4) | 3.3 | Synergy |
| JMI 6686 | 0.5 (0.06) | 0.13 (0.5) | 4.0 | Synergy |
| JMI 7140 | 0.5 (0.13) | 0.50 (0.5) | 4.5 | Synergy |
| JMI 8928 | 1.0 (0.13) | 0.19 (0.4) | 2.9 | Synergy |
| JMI 9365 | 0.3 (0.06) | 0.13 (0.5) | 2.5 | Synergy |
| JMI 11146 | 0.3 (0.03) | 0.13 (0.5) | 2.9 | Synergy |
| JMI 13734 | 0.5 (0.13) | 0.10 (0.4) | 4.0 | Synergy |
| JMI 13736 | 0.5 (0.13) | 0.10 (0.4) | 0.8 | Additive |
| JMI 15395 | 1.0 (0.06) | 0.13 (0.5) | 3.3 | Synergy |
| JMI 16140 | 2.0 (0.13) | 0.10 (0.4) | 3.0 | Synergy |
| JMI 33611 | 0.5 (0.06) | 0.25 (0.5) | 3.7 | Synergy |
| JMI 40979 | 0.5 (0.13) | 0.25 (0.5) | 3.0 | Synergy |

Legend for TABLES 7-11:
[1]ATCC quality control strains and JMI isolate numbers are shown.
[2]Concentrations of PlySs2 and antibiotic used in synergy time-kill experiments. Values were carefully determined in range-finding studies and represent concentrations that most closely approach ideal levels of PlySs2 (that is, resulting in a ~2-log$_{10}$ decrease in viability compared to growth control) and antibiotic (that is, resulting in <1 log decrease in viability compared to growth control).
[3]Decreases in log$_{10}$ colony counts (or ΔLog$_{10}$ CFU/mL) are shown for cultures treated for 6 hours with drug combination, compared to cultures treated with the most active single agent.
[4]Synergy is defined by the CLSI[21] as a ≥2-log$_{10}$ decrease in CFU/mL. Additive interactions are defined as a <2-log$_{10}$ decrease in CFU/mL.
[5]xMIC, denotes percentage of MIC represented by each concentration. For example, an xMIC value of 0.5 means that the optimal synergistic concentration for a particular drug is ½ the specific MIC value of a particular isolate or strain. The xMIC value is, therefore, the concentration of drug used in synergy time-kill assay divided by the MIC for that drug against the specific strain in the absence of reductant.
Key: ΔLog$_{10}$ CFU/mL = change in log$_{10}$ colony-forming units; MIC = minimum inhibitory concentration.

TABLE 8

Synergy Time-Kill Results with Vancomycin (MSSA)

| Strains[1] | Optimal Synergistic Concentrations[2] | | $\Delta Log_{10}$ CFU/mL[3] | Interaction[4] |
|---|---|---|---|---|
| | PlySs2 μg/mL (xMIC[5]) | Vancomycin μg/mL (xMIC) | | |
| ATCC 29213 | 1.0 (0.03) | 0.5 (0.5) | 2.3 | Synergy |
| JMI 1259 | 1.0 (0.13) | 0.5 (0.5) | 3.5 | Synergy |
| JMI 1787 | 1.0 (0.13) | 0.5 (0.5) | 3.1 | Synergy |
| JMI 6408 | 0.5 (0.06) | 0.5 (0.5) | 2.8 | Synergy |
| JMI 6686 | 1.0 (0.13) | 0.5 (0.5) | 5.0 | Synergy |
| JMI 7140 | 0.5 (0.13) | 0.5 (0.5) | 3.3 | Synergy |
| JMI 8928 | 0.5 (0.06) | 0.5 (0.5) | 1.8 | Additive |
| JMI 9365 | 0.5 (0.13) | 0.5 (0.5) | 2.6 | Synergy |
| JMI 11146 | 0.5 (0.06) | 0.3 (0.5) | 3.3 | Synergy |
| JMI 13734 | 0.5 (0.13) | 0.5 (0.5) | 4.3 | Synergy |

TABLE 8-continued

Synergy Time-Kill Results with Vancomycin (MSSA)

| Strains[1] | Optimal Synergistic Concentrations[2] | | $\Delta Log_{10}$ CFU/mL[3] | Interaction[4] |
|---|---|---|---|---|
| | PlySs2 μg/mL (xMIC[5]) | Vancomycin μg/mL (xMIC) | | |
| JMI 13736 | 0.5 (0.13) | 0.3 (0.3) | 2.3 | Synergy |
| JMI 15395 | 0.5 (0.03) | 0.5 (0.5) | 3.0 | Synergy |
| JMI 16140 | 1.0 (0.06) | 0.5 (0.5) | 3.3 | Synergy |
| JMI 18219 | 0.5 (0.13) | 0.5 (0.5) | 3.4 | Synergy |
| JMI 33611 | 0.5 (0.06) | 0.5 (0.5) | 3.6 | Synergy |
| JMI 40979 | 0.5 (0.13) | 0.5 (0.5) | 3.8 | Synergy |

TABLE 9

Synergy Time-Kill Results with Daptomycin (MSSA)

| Strains[1] | Optimal Synergistic Concentrations[2] | | $\Delta Log_{10}$ CFU/mL[3] | Interaction[4] |
|---|---|---|---|---|
| | PlySs2 μg/mL (xMIC[5]) | Daptomycin μg/mL (xMIC) | | |
| ATCC 25923 | 0.5 (0.02) | 0.25 (0.50) | 3.1 | Synergy |
| ATCC 29213 | 0.3 (0.03) | 0.25 (0.50) | 4.3 | Synergy |
| JMI 1259 | 1.0 (0.13) | 0.13 (0.25) | 3.5 | Synergy |
| JMI 1787 | 0.5 (0.06) | 0.07 (0.14) | 3.0 | Synergy |
| JMI 6408 | 0.5 (0.06) | 0.13 (0.25) | 2.7 | Synergy |
| JMI 6686 | 1.0 (0.13) | 0.14 (0.28) | 3.4 | Synergy |
| JMI 7140 | 0.5 (0.13) | 0.13 (0.25) | 2.6 | Synergy |
| JMI 8928 | 0.5 (0.06) | 0.13 (0.25) | 2.9 | Synergy |
| JMI 9365 | 0.3 (0.06) | 0.07 (0.28) | 1.8 | Additive |
| JMI 11146 | 0.5 (0.06) | 0.13 (0.50) | 4.2 | Synergy |
| JMI 13734 | 0.3 (0.06) | 0.08 (0.17) | 3.2 | Synergy |
| JMI 13736 | 0.5 (0.13) | 0.19 (0.38) | 4.5 | Synergy |
| JMI 15395 | 1.0 (0.06) | 0.25 (0.50) | 3.2 | Synergy |
| JMI 16140 | 0.5 (0.03) | 0.13 (0.50) | 1.9 | Additive |
| JMI 18219 | 0.5 (0.13) | 0.13 (0.25) | 3.7 | Synergy |
| JMI 33611 | 0.3 (0.03) | 0.13 (0.25) | 3.4 | Synergy |
| JMI 40979 | 0.3 (0.06) | 0.08 (0.16) | 2.5 | Synergy |

TABLE 10

Synergy Time-Kill Results with Vancomycin (MRSA)

| Strains[1] | Optimal Synergistic Concentrations[2] | | $\Delta Log_{10}$ CFU/mL[3] | Interaction[4] |
|---|---|---|---|---|
| | PlySs2 μg/mL (xMIC[5]) | Vancomycin μg/mL (xMIC) | | |
| ATCC 43300 | 1.0 (0.13) | 0.5 (0.5) | 2.1 | Synergy |
| JMI 2290 | 0.5 (0.06) | 0.5 (0.5) | 2.3 | Synergy |
| JMI 3345 | 0.5 (0.13) | 0.5 (0.5) | 5.0 | Synergy |
| JMI 4564 | 0.5 (0.03) | 0.5 (0.5) | 2.7 | Synergy |
| JMI 4789 | 1.0 (0.13) | 0.5 (0.5) | 3.3 | Synergy |
| JMI 5506 | 0.5 (0.13) | 0.3 (0.5) | 3.1 | Synergy |
| JMI 5675 | 0.5 (0.13) | 0.5 (0.5) | 3.2 | Synergy |
| JMI 6546 | 0.3 (0.03) | 0.5 (0.5) | 2.6 | Synergy |
| JMI 8941 | 0.5 (0.13) | 0.5 (0.5) | 1.8 | Additive |
| JMI 12568 | 0.5 (0.13) | 0.5 (0.5) | 5.0 | Synergy |
| JMI 18233 | 0.5 (0.06) | 0.5 (0.5) | 3.2 | Synergy |
| JMI 37753 | 0.5 (0.13) | 0.5 (0.5) | 1.6 | Additive |
| JMI 39086 | 0.5 (0.13) | 0.3 (0.5) | 2.5 | Synergy |

TABLE 11

Synergy Time-Kill Results with Daptomycin (MRSA)

| Strains[1] | Optimal Synergistic Concentrations[2] | | ΔLog$_{10}$ CFU/mL[3] | Inter- action[4] |
|---|---|---|---|---|
| | PlySs2 µg/mL (xMIC[5]) | Daptomycin µg/mL (xMIC) | | |
| ATCC 43300 | 0.5 (0.06) | 0.13 (0.25) | 4.1 | Synergy |
| JMI 2290 | 1.0 (0.13) | 0.25 (0.25) | 4.1 | Synergy |
| JMI 3345 | 1.0 (0.25) | 0.25 (0.50) | 5.0 | Synergy |
| JMI 4564 | 0.5 (0.03) | 0.13 (0.25) | 2.8 | Synergy |
| JMI 4789 | 1.0 (0.13) | 0.13 (0.25) | 2.4 | Synergy |
| JMI 5506 | 0.5 (0.13) | 0.13 (0.25) | 2.3 | Synergy |
| JMI 5675 | 0.5 (0.13) | 0.13 (0.25) | 3.4 | Synergy |
| JMI 6546 | 1.0 (0.13) | 0.06 (0.13) | 3.3 | Synergy |
| JMI 8941 | 0.5 (0.06) | 0.13 (0.25) | 2.1 | Synergy |
| JMI 12568 | 0.5 (0.13) | 0.13 (0.50) | 3.6 | Synergy |
| JMI 18233 | 1.0 (0.13) | 0.25 (0.25) | 5.7 | Synergy |
| JMI 37753 | 0.5 (0.06) | 0.13 (0.25) | 2.3 | Synergy |
| JMI 39086 | 0.5 (0.13) | 0.13 (0.25) | 3.5 | Synergy |

Example 4

Broth microdilution MIC testing was performed using 96 well panels according to the methods described above for Example 1 (CLSI methodology, CLSI document M07-A9, column 32 no 2). In the present studies, however, both PlySs2 lysin and antibiotic daptomycin are present together in each well at different starting concentrations. Studies were completed with 12 different MRSA S. aureus strains. In each instance, the MIC of PlySs2 for the strain was first determined. DAP MICs for each strain were based on broth microdilution MIC testing according to published methodology and confirmed with published and available data for the tested isolates. 5.5×10$^5$-1×10$^6$ cells were added to each well and grown in the presence of various amounts of PlySs2 lysin and daptomycin for 24 hours at 37° C. without aeration. MIC values were determined by eye and confirmed by plating bacteria to determine viable cell counts in each well of a 96-well plate. Cultures were assessed in the presence and absence of a reducing agent (e.g., beta mercaptoethanol (BME), dithiothreitol (DTT)). MIC values are lower relatively in the presence of reducing agent and repeatability is improved with reducing agent.

Dual Agent MIC Determinations.

The dual agent MIC assay is derived from the standard broth microdilution method (Methods for dilution antimicrobial susceptibility tests for bacteria that grow aerobically (2012) Vol. 32 (Clinical and Laboratory Standards Institute (U.S.), Wayne (Pa.)). Whereas the MIC assay dilutes one drug across the x-axis, the MIC combo assays dilutes two drugs together across the x axis. Two to four 96-well polypropylene microtiter plates (Becton, Dickenson, and Company) are combined to yield desired dilution schemes. PlySs2 is first diluted two-fold vertically downward in column 1, yielding a concentration range of 2,048 to 1 µg/mL. Daptomycin is next added at a constant concentration (4 µg/mL) to each well of column 1. All of the wells of column 1, therefore, containing a dilution range of PlySs2 against a background of 4 µg/mL daptomycin. Column 1 is next diluted two-fold across the entire x-axis such that all the wells of column 11 have a daptomycin concentration of 0.0037 µg/mL. After drug dilutions, cells are added (~5×10$^5$ CFUs/mL) and after 24 hours of incubation at 35° C. in ambient air the MICs was recorded as the most dilute drug concentrations inhibiting bacterial growth.

Exemplary results with eight MRSA strains are depicted in FIGS. 9-18. In each of FIGS. 9-18, a twelve-well doubling dilution range proceeds to the right for each panel row. Each panel represents the well of a 96-well plate. The indicted bacterial strains were then inoculated into each well and incubated for 24 hours at which time growth was examined. Unshaded panels indicate wells in which drug combinations inhibited growth. The yellow (light)-shaded panels indicate the lowest drug-combination concentrations that inhibited growth (essentially corresponding to the MIC). The red (dark)-shaded panels indicate bacterial growth (in other words agent combinations that did not inhibit growth). Studies were conducted in the presence and absence of reducing agent. In each instance, with or without the reducing agent, significant synergy was observed, with multi-fold reduction in amount of both lysin and antibiotic required when both were provided in combination. Reduction in antibiotic required was particularly significant with added lysin.

The overall experimental results with a dozen MRSA strains are summarized in TABLE 12 below. As shown below and depicted in FIGS. 9-18, combining PlySs2 and antibiotic (daptomycin) together can synergistically achieve 2-4 fold reduction in the effective MIC of PlySs2. Remarkably, combining PlySs2 and daptomycin together can synergistically achieve 16-256 increased sensitivity (fold reduction) in the effective MIC of the antibiotic daptomycin.

TABLE 12

| MRSA STRAIN | PlySs2 | | | Daptomycin | | |
|---|---|---|---|---|---|---|
| | MIC alone[1] | MIC combo[2] | Fold reduction[3] | MIC alone | MIC combo | Fold reduction |
| 553 | 2 | 1 | 2 | 1 | 0.0075 | 128 |
| 223 | 2 | 0.5 | 4 | 1 | 0.0075 | 128 |
| 270 | 8 | 2 | 4 | 1 | 0.015 | 64 |
| 269 (MW2) | 8 | 2 | 4 | 1 | 0.015 | 64 |
| 241 | 4 | 2 | 2 | 1 | 0.0037 | 256 |
| 263 | 8 | 2 | 4 | 1 | 0.0075 | 128 |
| 650 | 8 | 4 | 2 | 1 | 0.015 | 64 |
| 827 | 8 | 4 | 2 | 1 | 0.0075 | 128 |
| 828 | 8 | 2 | 4 | 1 | 0.0075 | 128 |
| 829 | 8 | 4 | 2 | 1 | 0.0075 | 128 |
| 830 | 4 | 2 | 2 | 1 | 0.015 | 64 |
| 833 | 8 | 2 | 4 | 1 | 0.0075 | 128 |

[1]The "MIC alone" value is the single-agent MIC (in µg/mL) for each drug.
[2]The "MIC combo" value is the most dilute concentration of each agent (in µg/mL) that, when combined, inhibited growth.
[3]Fold Reduction (Increased sensitivity) corresponds to the MIC combo/MIC alone for each agent.

Example 5

Further assessment of synergy was undertaken by performing checkerboard assays and calculating fractional inhibitory concentration index (FICI) values (Tallarida R J (2012) J Pharmacol and Exper Therapeutics 342:2-8). These studies were performed using exemplary antibiotics daptomycin, vancomycin and oxacillin. Using this assessment, synergy is defined as inhibitory activity greater than would be predicted by adding the two drugs together (FICI of ≤0.5). Representative isobolograms for the different antibiotics against MRSA and MSSA strains are provided in FIG. 19. Synergy was observed for 79% (daptomycin), 86% (vancomycin), and 100% (oxacillin) of the 29 MSSA strains and for 89% (daptomycin) and 69% (vancomycin) of the 26 MRSA strains. The results are tabulated below in TABLES 13-15.

TABLE 13

Checkerboard Analyses of PlySs2 Combined with Oxacillin, Vancomycin, or Daptomycin (MSSA)

| Strains | Oxacillin | | Vancomycin | | Daptomycin | |
|---|---|---|---|---|---|---|
| | $FIC_{min}$ | Interaction | $FIC_{min}$ | Interaction | $FIC_{min}$ | Interaction |
| ATCC 25923 | 0.156 | Synergy | 0.500 | Synergy | 0.500 | Synergy |
| ATCC 29213 | 0.250 | Synergy | 0.500 | Synergy | 0.750 | Additive |
| JMI 243 | 0.187 | Synergy | 0.375 | Synergy | 0.312 | Synergy |
| JMI 332 | 0.187 | Synergy | 0.281 | Synergy | 0.312 | Synergy |
| JMI 1104 | 0.375 | Synergy | 0.375 | Synergy | 0.265 | Synergy |
| JMI 1259 | 0.187 | Synergy | 0.500 | Synergy | 0.500 | Synergy |
| JMI 1282 | 0.375 | Synergy | 1.00 | Additive | 0.750 | Additive |
| JMI 1787 | 0.375 | Synergy | 0.500 | Synergy | 0.562 | Additive |
| JMI 3521 | 0.250 | Synergy | 0.75 | Additive | 0.375 | Synergy |
| JMI 3671 | 0.312 | Synergy | 0.562 | Additive | 0.500 | Synergy |
| JMI 4811 | 0.375 | Synergy | 0.375 | Synergy | 0.500 | Synergy |
| JMI 6408 | 0.375 | Synergy | 0.375 | Synergy | 0.312 | Synergy |
| JMI 6414 | 0.375 | Synergy | 0.375 | Synergy | 0.375 | Synergy |
| JMI 6544 | 0.250 | Synergy | 0.500 | Synergy | 0.375 | Synergy |
| JMI 6686 | 0.281 | Synergy | 0.500 | Synergy | 0.375 | Synergy |
| JMI 7140 | 0.375 | Synergy | 0.375 | Synergy | 0.500 | Synergy |
| JMI 8928 | 0.375 | Synergy | 0.375 | Synergy | 0.500 | Synergy |
| JMI 9365 | 0.125 | Synergy | 0.375 | Synergy | 0.500 | Synergy |
| JMI 11146 | 0.250 | Synergy | 0.375 | Synergy | 0.375 | Synergy |
| JMI 13734 | 0.375 | Synergy | 0.500 | Synergy | 0.375 | Synergy |
| JMI 13736 | 0.281 | Synergy | 0.500 | Synergy | 0.500 | Synergy |
| JMI 15395 | 0.312 | Synergy | 0.250 | Synergy | 0.500 | Synergy |
| JMI 16195 | 0.375 | Synergy | 0.375 | Synergy | 0.281 | Synergy |
| JMI 16140 | 0.375 | Synergy | 0.375 | Synergy | 0.531 | Additive |
| JMI 18219 | 0.500 | Synergy | 0.500 | Synergy | 0.562 | Additive |
| JMI 24368 | 0.375 | Synergy | 0.375 | Synergy | 0.375 | Synergy |
| JMI 29793 | 0.375 | Synergy | 0.56 | Additive | 0.562 | Additive |
| JMI 33611 | 0.312 | Synergy | 0.375 | Synergy | 0.375 | Synergy |
| JMI 40979 | 0.312 | Synergy | 0.375 | Synergy | 0.312 | Synergy |

Key:
$FIC_{min}$ = minimum fractional inhibitory concentration

TABLE 14

Checkerboard Analyses of PlySs2 Combined with Vancomycin or Daptomycin (MRSA)

| Strains | Vancomycin | | Daptomycin | |
|---|---|---|---|---|
| | $FIC_{min}$ | Interaction | $FIC_{min}$ | Interaction |
| ATCC 43300 | 0.500 | Synergy | 0.5 | Synergy |
| JMI 1225 | 0.625 | Additive | 0.375 | Synergy |
| JMI 1280 | 0.375 | Synergy | 0.375 | Synergy |
| JMI 2290 | 0.500 | Synergy | 0.500 | Synergy |
| JMI 3345 | 0.375 | Synergy | 0.375 | Synergy |
| JMI 3346 | 0.375 | Synergy | 0.375 | Synergy |
| JMI 4564 | 0.375 | Synergy | 0.500 | Synergy |
| JMI 4789 | 0.750 | Additive | 0.560 | Additive |
| JMI 5506 | 0.562 | Additive | 0.375 | Synergy |
| JMI 5675 | 0.375 | Synergy | 0.375 | Synergy |
| JMI 6378 | 0.500 | Synergy | 0.560 | Additive |
| JMI 6182 | 1.060 | Additive | 0.500 | Synergy |
| JMI 6546 | 0.375 | Synergy | 0.375 | Synergy |
| JMI 7053 | 0.375 | Synergy | 0.500 | Synergy |
| JMI 8941 | 0.375 | Synergy | 0.500 | Synergy |
| JMI 9328 | 0.562 | Additive | 0.375 | Synergy |
| JMI 10339 | 0.531 | Additive | 0.500 | Synergy |
| JMI 11127 | 0.531 | Additive | 0.625 | Additive |
| JMI 12568 | 0.250 | Synergy | 0.375 | Synergy |
| JMI 15992 | 0.187 | Synergy | 0.500 | Synergy |
| JMI 18233 | 0.375 | Synergy | 0.500 | Synergy |
| JMI 37753 | 0.375 | Synergy | 0.375 | Synergy |
| JMI 39086 | 0.500 | Synergy | 0.500 | Synergy |
| JMI 39848 | 0.500 | Synergy | 0.375 | Synergy |
| JMI 43255 | 0.375 | Synergy | 0.375 | Synergy |
| JMI 44465 | 0.625 | Additive | 0.500 | Synergy |

Key: $FIC_{min}$ = minimum fractional inhibitory concentration.

TABLE 15

Summary of PlySs2 Interactions with Antimicrobial Agents Based on Checkerboard Assays and Calculated FIC Values

| | % Interactions with PlySs2[a)] | | | | | |
|---|---|---|---|---|---|---|
| | Oxacillin | | Vancomycin | | Daptomycin | |
| Species (N) | Synergistic | Additive | Synergistic | Additive | Synergistic | Additive |
| MSSA (29) | 100 | 0 | 86.2 | 13.8 | 79.3 | 20.7 |
| MRSA (26) | NA | NA | 69.2 | 30.8 | 88.5 | 11.5 |

Key:
FIC = fractional inhibitory concentration;
NA = not applicable.

In the checkerboard assay, drug interactions are defined as either synergistic, additive, or antagonistic based on the $FIC_{min}$ for each combination. The FIC for a drug is defined as the MIC of the drug in combination divided by the MIC of the drug used alone. The $FIC_{min}$ is based on the sum of FICs for each drug. If the $FIC_{min}$ is ≤0.5, the combination is interpreted as being synergistic; between >0.5 and ≤2 as additive; and >2 as antagonistic.

Example 6

PlvSs2 Accelerates Antibiotic Binding to the Cell Envelope

Figure 20:
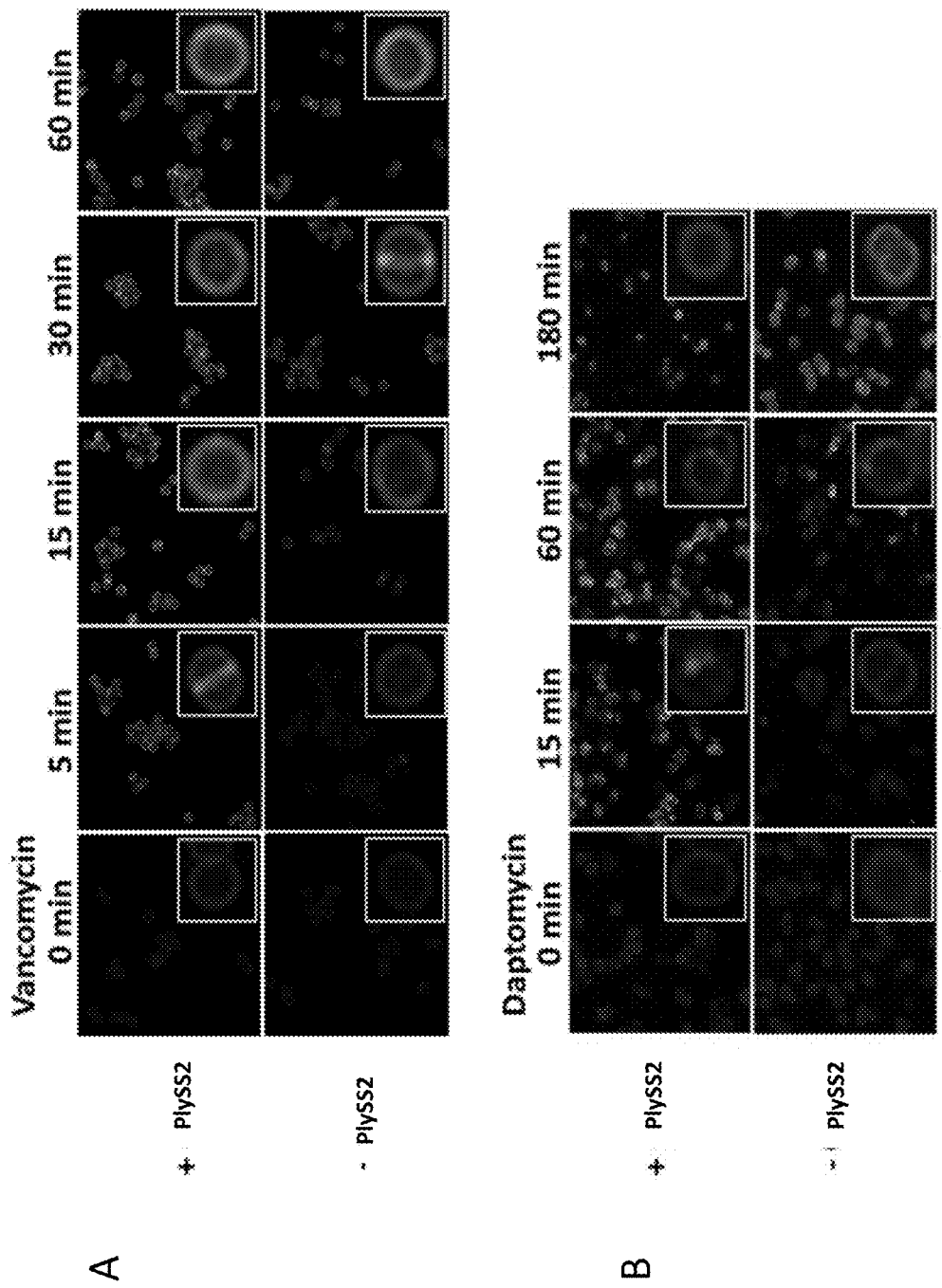
FIGS. 20A and 20B provides a time course of *S. aureus* staining by BODIPY-labeled daptomycin (A) and vancomycin (B) in the absence and presence of sub-MIC amounts of PlySs2.

As a complement to the synergy studies, daptomycin and vancomycin cell envelope-binding was examined using BODIPY-fluorescein-labeled antibiotics in the presence and absence of sub-MIC levels of CF-301. A time-course analysis of daptomycin binding (FIG. 20A) shows antibiotic penetration after only 15 minutes in the presence of CF-301 (at $\frac{1}{32}^{nd}$ MIC) versus 3 hours without CF-301. Similarly, cell wall-labeling with vancomycin occurs within 5 minutes in the presence of CF-301 ($\frac{1}{8}^{th}$ MIC) versus 30 minutes without CF-301 (FIG. 20B). For both antibiotics, the labeling was first observed at bacterial division planes.

Example 7

Daptomycin binds avidly to pulmonary surfactant and therefore is not effective in treatment of staphylococcal pneumonia. In view of the effectiveness of PlySs2 and daptomycin in combination against susceptible bacteria, a shown above, PlySs2 lysin and daptomycin were evaluated alone and in combination in the presence of a commercially available surfactant, to mimic pulmonary surfactant.

MRSA strain MW2 and MSSA strain ATCC 29213 were used in these studies. Daptomycin and PlySs2 lysin were first evaluated alone in the presence of surfactant (Survanta, Abbott Laboratories). The MICs of daptomycin and PlySs2 for each strain were determined in the presence of Survanta using broth microdilution methods. Doubling-dilution series were established in the presence and absence of surfactant at concentrations ranging from 0% up to 15%. MICs were scored by eye at 24 hours and confirmed by CFU counts in all wells. A similar study is reported by Silverman et al., 2005 (JID, volume 191, 2149-52) using MSSA strain 581. The fold change in MIC for daptomycin and CF301 at each surfactant concentration (compared to MICs obtained in the absence of surfactant) were then calculated. The fold change in MIC at surfactant concentrations for each strain is depicted in FIG. 21. In the presence of Survanta as surfactant, daptomycin MIC is inhibited up to 256 fold. At a surfactant concentration of 1.25%, daptomycin is inhibited more than 20 fold. In contrast, the MIC of PlySs2 is inhibited 8 fold, consistently across a range from 1.25 to 15% surfactant.

Figure 22:
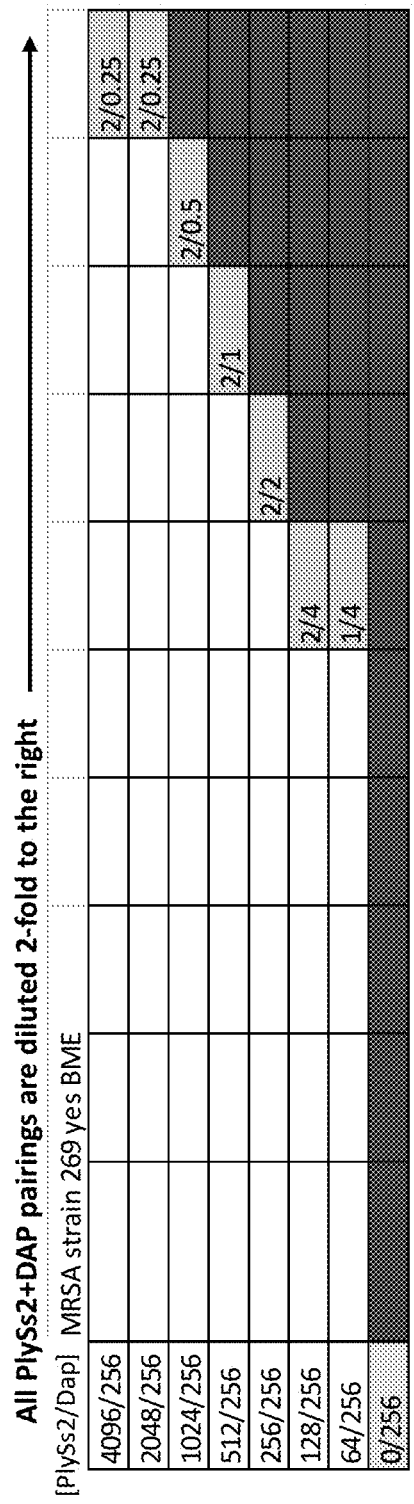
FIG. 22 provides a panel of dose dilutions of pairings of daptomycin and PlySs2 at the noted concentrations on MRSA strain 269 in the presence of 15% surfactant (Survanta).

The effects of combinations of PlySs2 lysin and daptomycin were evaluated in the presence of 15% surfactant (Survanta) in a combination MIC study. The experimental setup is similar to that described above for the combination MIC studies without surfactant (see Example 3). The results of synergy evaluation in the presence of surfactant are shown in FIG. 22. Briefly, the PlySs2 lysin plus daptomycin concentrations shown in the left-most wells were diluted two-fold across all twelve wells of each row. MRSA strain 269 (MW2) cells ($5.5 \times 10^5$-$1 \times 10^6$) were then added to each well and incubated for 24 hours before growth was assessed. Unshaded wells indicate growth inhibition. Yellow (lightly)-shaded wells indicate the most dilute drug combinations that still inhibit growth (ie, the MIC). Red (dark)-shaded wells indicate drug combinations that allow growth. The PlySs2 synergy dose is 2 µg/ml or ⅛ of the MIC for the strain tested. In this study, daptomycin is effective to 0.25 µg/ml, which corresponds to $\frac{1}{1024}$ MIC of daptomycin.

Example 8

Combination Versus Single-Agent Therapy in Murine Models of Bacteremia

Animal studies were undertaken to assess the effect of PlySs2 in combination with antibiotic against *S. aureus* infection in vivo in murine models of bacteremia. BALB/c mice were injected IP with different levels inoculums of MRSA strains and the animals are then dosed with drug—either antibiotic, PlySs2 lysin, or a combination of antibiotic and PlySs2.

Figure 23:
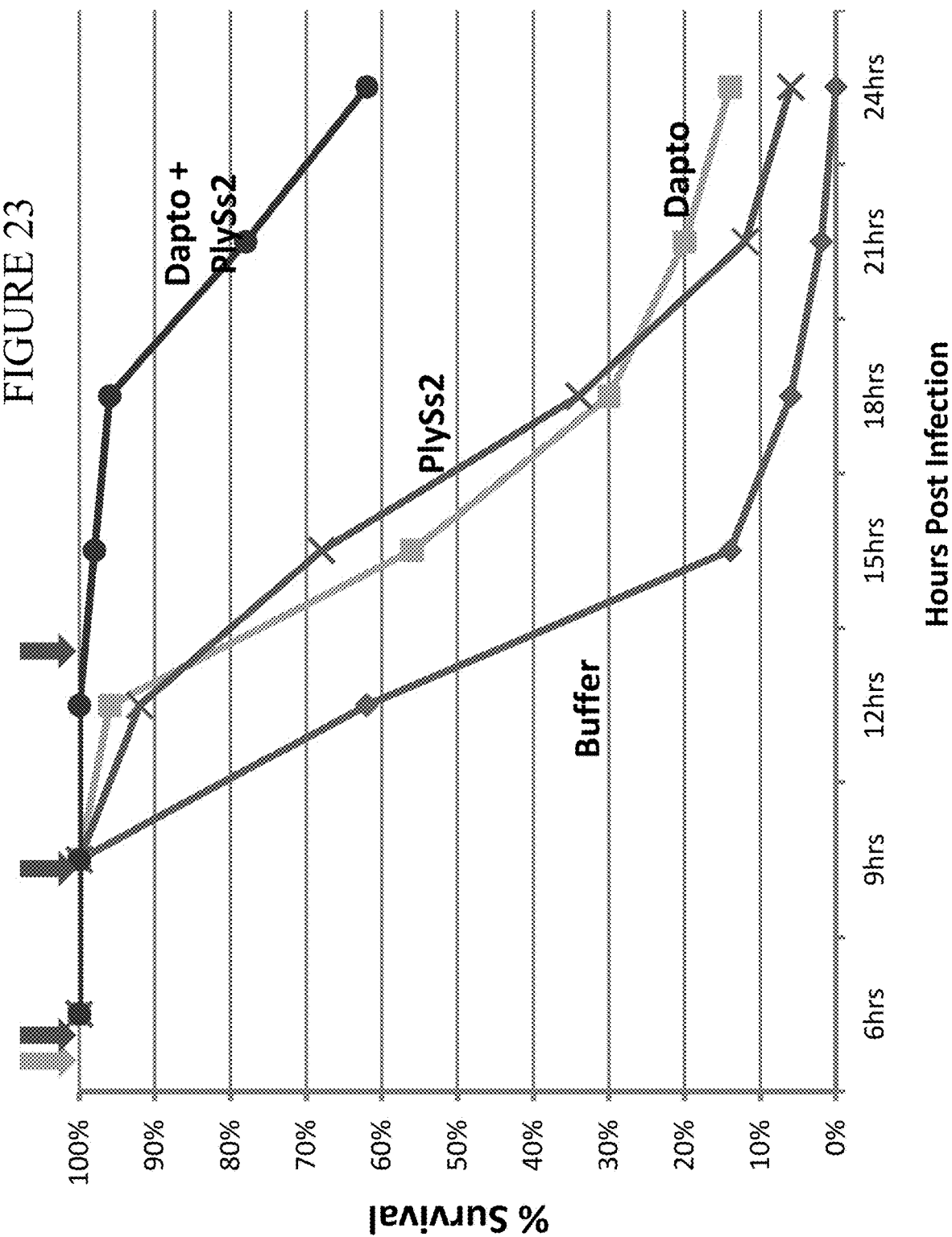
FIG. 23 provides a compiled graph of % survival of mice (50 animals) challenged with MRSA strain 269 (MW2) in several experiments having bacterial inoculum strengths of $1.1\text{-}3.1 \times 10^6$ CFU and treated with daptomycin or PlySs2 alone or in combination.
Figure 24:
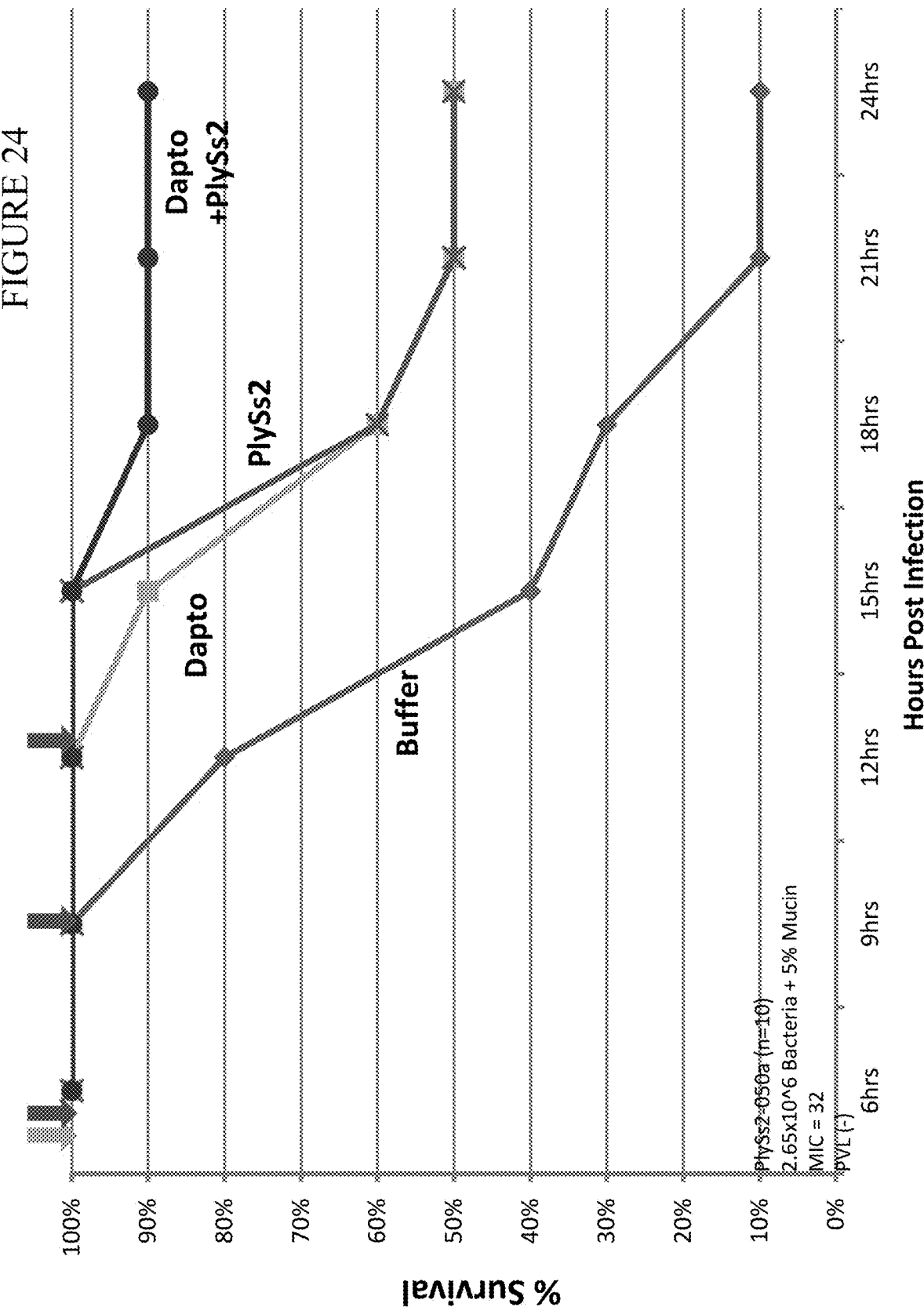
FIG. 24 depicts % survival of mice challenged with MRSA strain 220 at $2.65 \times 10^6$ CFU and treated with the indicated doses of daptomycin or PlySs2 alone or in combination.
Figure 25:
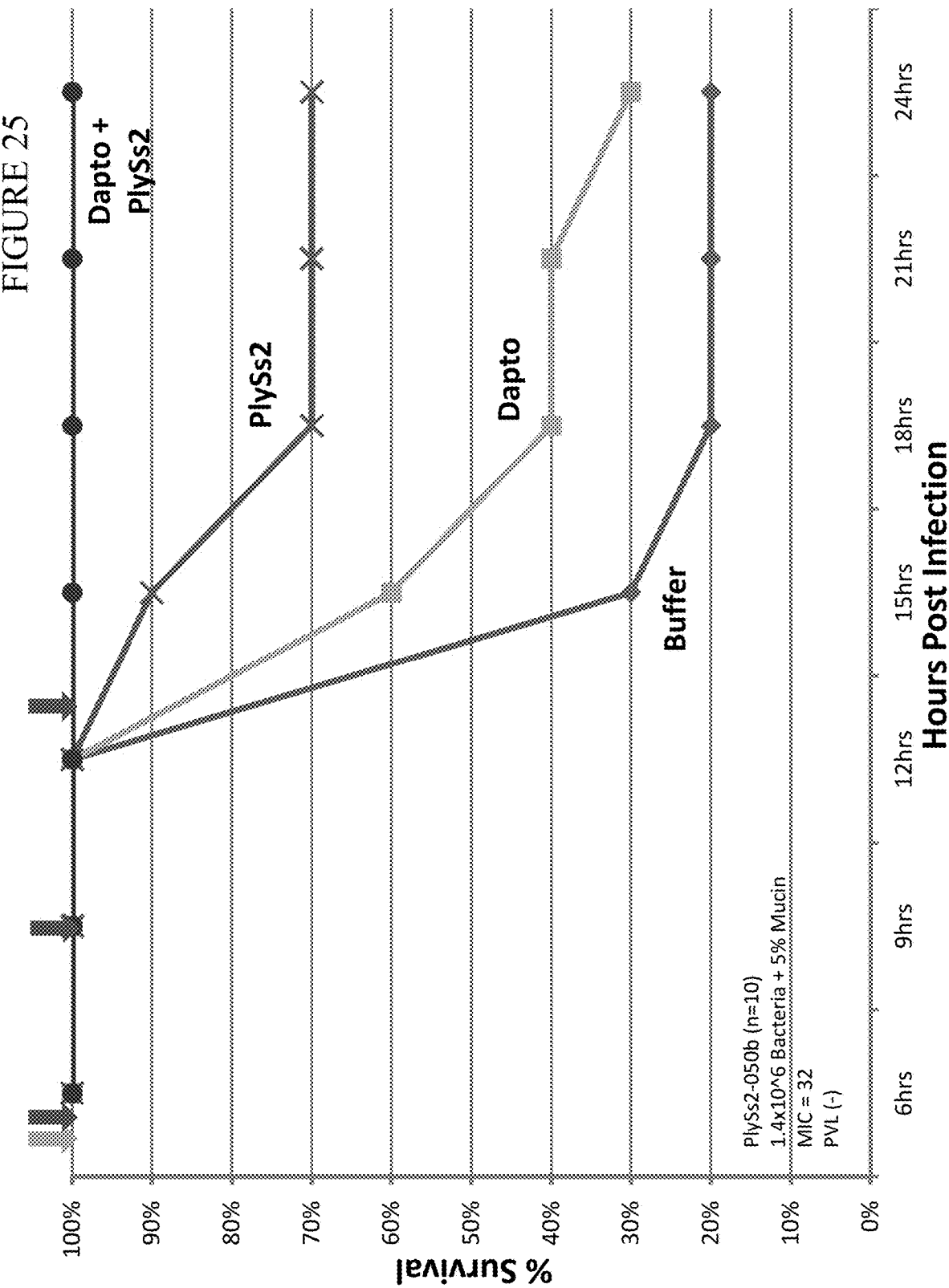
FIG. 25 depicts % survival of mice challenged with MRSA strain 833 at $1.4 \times 10^6$ CFU and treated with the indicated doses of daptomycin or PlySs2 alone or in combination.
Figure 26:
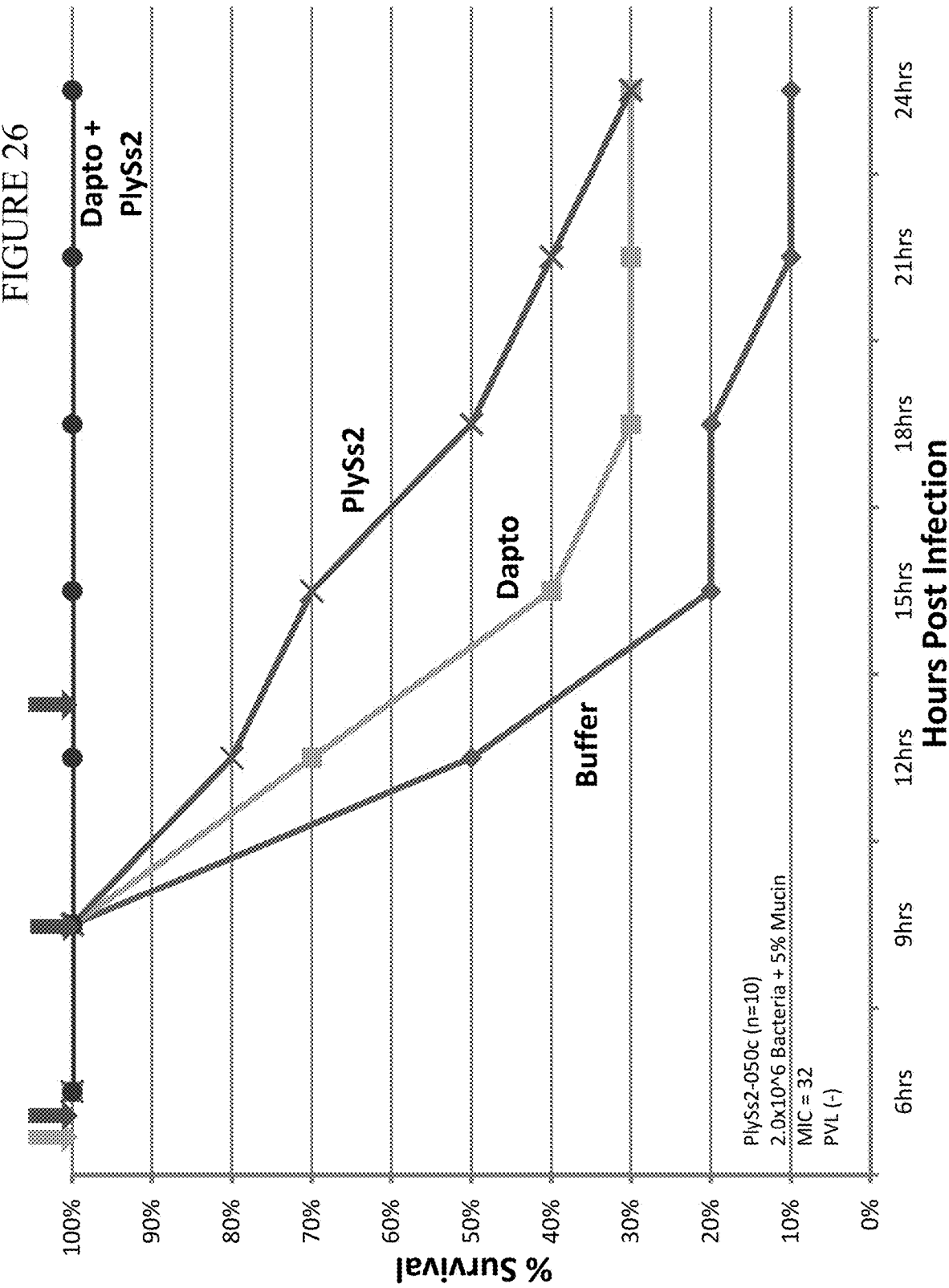
FIG. 26 depicts % survival of mice challenged with MRSA strain 833 at $2.0 \times 10^6$ CFU and treated with the indicated doses of daptomycin or PlySs2 alone or in combination.

In a first set of studies using inoculums in the range of $10^6$ of bacteria, 35 ug of daptomycin was injected subcutaneously (sc) at 5 hrs post bacterial infection, in a single dose. This dose is equivalent to 1.75 mg/kg dose of daptomycin for a 20 gram mouse, while the human equivalent dose of daptomycin in mice would be 50 mg/kg. Dosing of 1.75 mg/kg of daptomycin in mice is equivalent to about 3.5% of the human equivalent dose. PlySs2 was injected IP three times a day (TID), with 15 µg of PlySs2 administered at 5 hrs, 9 hrs, and 13 hrs post bacterial infection (15 µg is approximately equal to a dose of 0.8 mg/kg for a 20 gram mouse). The animals are monitored and percent survival recorded every three hours up to 24 hours post infection. Animal survival with MRSA (strain 269 or MW2) doses of $1.8 \times 10^6$, $1.1 \times 10^6$, $3.0 \times 10^6$ and $3.1 \times 10^6$ bacteria was assessed and a compiled graph of survival data is provided in FIG. 23 for this MRSA strain. Similar studies were conducted with other *S. aureus* strains (strains 220 and 833) with comparable results (FIGS. 24-26). In all instances, animal survival was remarkably enhanced by combination dosing with PlySs2 lysin and antibiotic daptomycin. These studies provide in vivo evidence of the efficacy of combination therapy of PlySs2 lysin with antibiotic daptomycin compared to PlySs2 lysin or antibiotic daptomycin alone.

High-Dose Inoculum Studies

Figure 27:
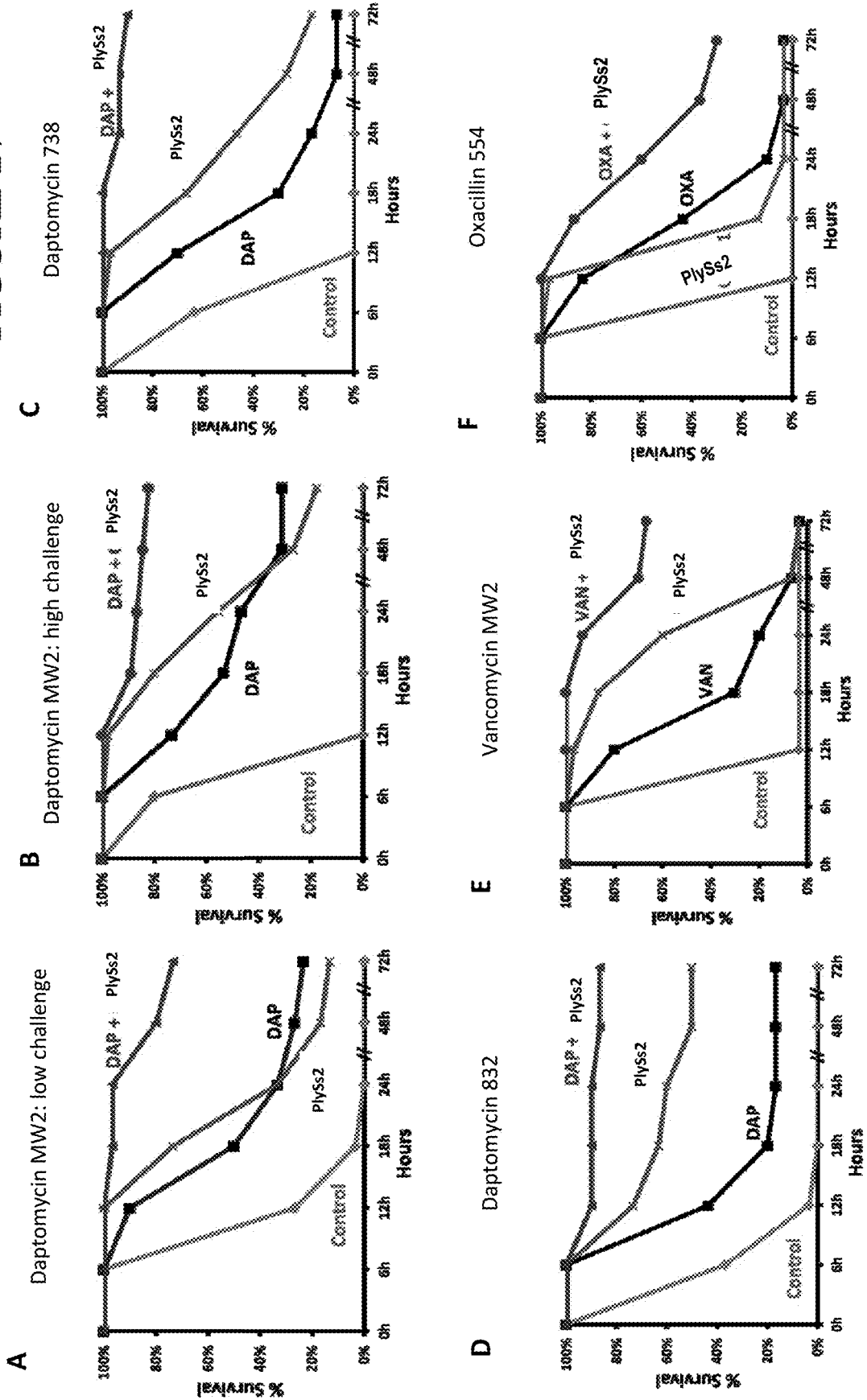
FIG. 27A-27F depicts survival curves of combination therapy compared to mono-therapies in murine models of bacteremia. Mice were challenged with either $7.5 \times 10^6$ cfu/mouse i.p. (low challenge model—panel a) or $10^9$ cfu/mouse i.p. (high challenge model—panels b-f) at time 0 and were treated with either antibiotic, PlySs2, combination of PlySs2 and antibiotic, or control and the resulting survival data are shown in Kaplan-Meier format. All doses were administered as a single bolus dose except for vancomycin (BID, panel e) and oxacillin (QID, panel f) which were administered as multiple doses over the first 24 hr period. Routes of administration were PlySs2 (i.p.), daptomycin and vancomycin (subcutaneous), and oxacillin (intramuscular). P values were calculated for the combinations versus antibiotic alone. (A) Low challenge model using MRSA strain MW2 with daptomycin at 2 mg/kg and PlySs2 at 1.25 mg/kg. Dosing at 4 hr post inoculation, n=30, P<0.0001. (B) High challenge model using MRSA strain MW2 with daptomycin at 50 mg/kg and PlySs2 at 5.25 mg/kg. Dosing at 2 hr post inoculation, n=45, P<0.0001. (C) same as B using MRSA strain 738, n=30, P<0.0001. (D) same as B using MRSA strain 832, n=30, P<0.0001. (E) High challenge model using MRSA strain MW2 with vancomycin at 110 mg/kg BID and PlySs2 at 5.25 mg/kg. Dosing initiated at 2 hr post-inoculation, n=30, P<0.0001. (F) High challenge model using MSSA strain ATCC 25923 with oxacillin at 200 mg/kg QID and PlySs2 at 5.25 mg/kg. Dosing initiated at 2 hr post-inoculation, n=30 P<0.0001.

Additional animal studies in a mouse bacteremia model were conducted to assess the ability of PlySs2 to enhance the efficacy of standard-of-care antibiotics in vivo. In the low challenge model (up to $7 \times 10^6$ CFU inoculum with dosing at 4 hours), single-agent therapy administered as a single dose of either 1.25 mg/kg PlySs2 or 2 mg/kg daptomycin resulted in 13% and 23% survival at 72 hours, respectively (FIG. 27A). Upon combination of PlySs2 with daptomycin a significant enhancement was observed with a 72 hour survival rate of 73% (P<0.0001). The combination of PlySs2 with daptomycin was therefore superior to each agent alone under low challenge conditions.

To test how robust the PlySs2 combination therapy may be, we increased the bacterial inoculum to a point where human-simulated doses of single-agent antibiotics were poorly efficacious. In this high challenge model ($10^9$ CFU inoculum with dosing at 2 hours), human-simulated doses of either daptomycin (50 mg/kg once daily)[26] or vancomycin (110 mg/kg twice daily)[27] as single agents yielded 24 hour survival rates of 47% and 20%, respectively, and 72 hour survival rates of 31% and 3%, respectively (FIGS. 27B and 27E). PlySs2 administered as a single agent similarly yielded survival rates of 56/60% and 18/3% at 24 and 72 hours, respectively. In contrast, PlySs2 in combination with either daptomycin or vancomycin achieved 24 hour survival rates of 87% and 93% at 24 hours and 82% and 67% at 72 hours, respectively, demonstrating superiority of the combination therapies over single-agent regimens under these challenging infection conditions. Additional PlySs2/daptomycin combination experiments were performed with two additional MRSA strains, yielding similar results (FIGS. 27C and 27D). When PlySs2 was further tested in combination with oxacillin using a MSSA strain as the inoculum, the combination treatment was again superior to that of the single agents (FIG. 27F). Taken together, the results demonstrate that PlySs2/antibiotic combinations are more efficacious than single-agent regimens for treating bacteremia and that statistically significant results are obtained across various standard-of-care antibiotics and across multiple S. aureus strains ($P<0.0001$ in all cases).

Lysin PlySs2 Demonstrates Dose-Responsive, Rapid-Kill Kinetics in-vivo

In a murine bacteremia model, PlySs2 exhibits a clear dose-response with survival enhancement over that observed for the mock-injected control with as little as 0.25 mg/kg and significant protection at the 5 mg/kg dose (data not shown). To assess the speed of bactericidal activity of PlySs2 in vivo, MRSA CFUs were measured in the blood of infected mice before and after administration of PlySs2. Upon dosing 5.25 mg/kg PlySs2 at 2-hours post-infection, a $0.5\text{-}\log_{10}$ decrease in CFUs occurred in 15 minutes and a $2\text{-}\log_{10}$ log decrease was observed within the 60 minutes of treatment, demonstrating the rapid bactericidal activity of PlySs2 in the bloodstream of infected animals (data not shown).

Murine Bacteremia Model.

Female BALB/c (inbred strain) mice, 5-7 weeks of age, 16.0-19.5 g body weight were purchased from Jackson Laboratories, Bar Harbor, Me. and utilized in all mouse experiments. Exponential phase bacterial inocula were generated by allowing bacterial cells to grow to an optical density of ~0.5 at 600 nm, harvested, washed, and concentrated between $1.5\times10^7\text{-}2\times10^9$ CFU/ml. The bacterial pellet was suspended in an appropriate volume of 5% (w/v) mucin (Sigma Lot# SLBD5666V or SLBD5666V) to achieve the specific inoculum and placed on wet ice. Five hundred µL (~$7.5\times10^6\text{-}1\times10^9$ CFU) were injected i.p. into mice. The study drug doses were weight-adjusted with the injected volume between 160-200 µL. Post-infection survival was assessed every 3 or 6 hours for the first 24 hours, then at 48 and 72 hours. The experiments were repeated 2-3 times with each treatment group containing between 10-20 mice. All experimental manipulations using the infectious agent were conducted in a BSL-2 hood. Dead animals were removed upon observation of mortality.

Example 9

Figure 28:
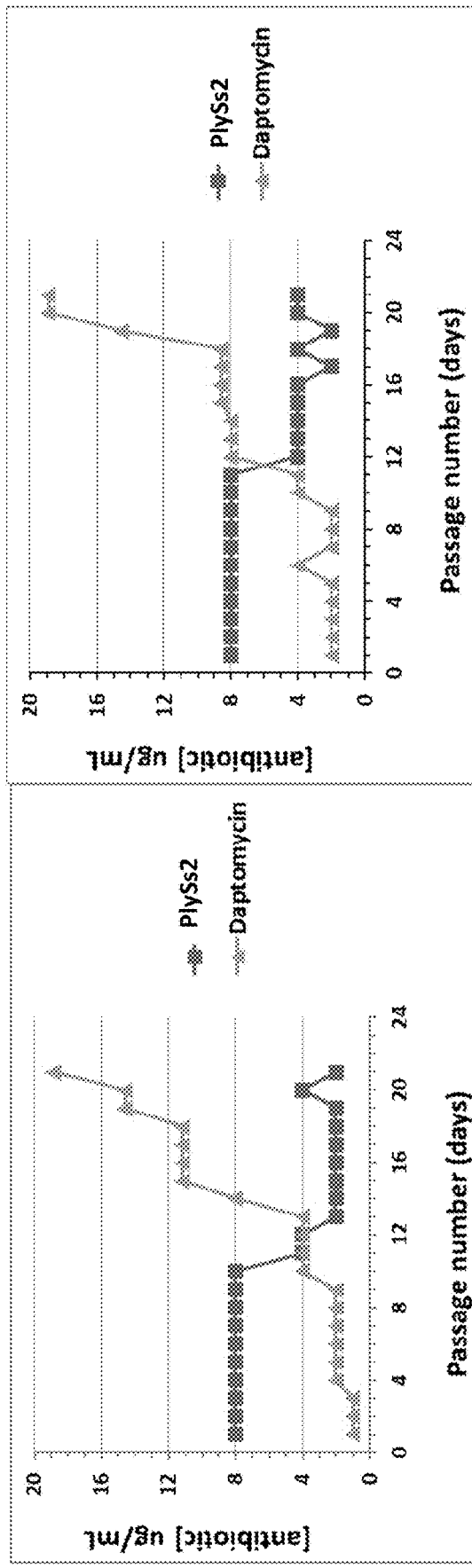
FIG. 28 depicts MIC of daptomycin and PlySs2 on an MSSA and a MRSA strain with passage number and development of daptomycin resistance. PlySs2 MIC drops showing PlySs2 increased sensitivity with increased daptomycin resistance.

Serial passage experiments were conducted with MRSA strain ATCC 700699 and MSSA strain ATCC 25923 to generate and evaluate daptomycin resistance and PlySs2 lysin. These studies were conducted to evaluate and determine whether daptomycin resistance correlates with lysin resistance or sensitivity, including particularly resistance or sensitivity to PlySs2 lysin. First, daptomycin resistant clones were generated (with increasing MIC values), in a step-wise manner, over 21 days of in vitro growth. Then, the series of daptomycin resistant clones were assessed with respect to lysin MIC values, by evaluating PlySs2 lysin MIC. The results are depicted in FIG. 28. In the daptomycin resistant clones, daptomycin MIC rises from 1 to 18 µg/mL. PlySs2 lysin MIC decreases from 8 to between 2-4 µg/mL. These studies show that daptomycin resistance correlates with PlySs2 lysin sensitivity. These are the first studies to evaluate daptomycin resistance and lysin sensitivity. Remarkably, in these conditions resistance to daptomycin confers increased response to lysin, providing enhanced rational for combination or serial administration and therapy.

Example 10

Serial passage resistance studies were undertaken to assess the ability of PlySs2 to suppress the emergence of antibiotic resistance when used in combination with various standard-of-care antibiotics used to treat *Staphylococcus aureus* infections. Methods used to perform single-agent and combination serial passage experiments are described in Palmer et al (Palmer et al (2011) Antimicrobial Agents and Chemotherapy 55:3345-56) and Berti et al (Berti et al (2012) Antimicrobial Agents and Chemotherapy 56:5046-53), respectively. Increases in the MIC values for the antibiotic were assessed in triplicate for a MRSA *Staphylococcus aureus* strain (MW2) grown either in the presence of antibiotic alone or in the presence of antibiotic plus sub-MIC values of PlySs2. The MIC for PlySs2 for strain MW2 is 32 ug/ml (without DTT). Thus, sub-MIC values of 4 ug/ml (corresponding to $\frac{1}{8}$ MIC) or 8 ug/ml (corresponding to $\frac{1}{4}$ MIC) were chosen as the concentration of PlySs2 for these experiments. Both daptomycin and vancomycin were tested as exemplary antibiotics in this study.

Figure 30:
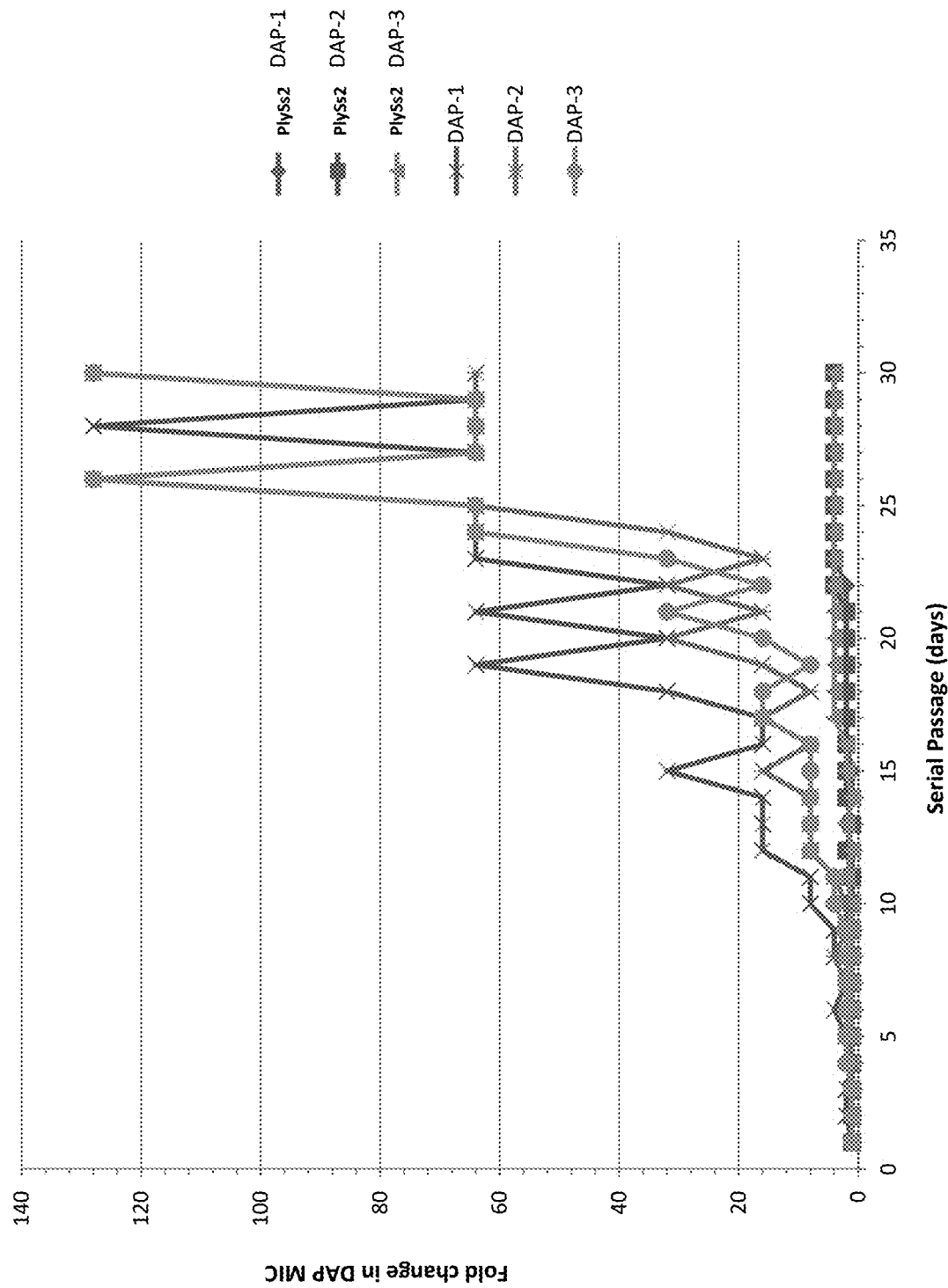
FIG. 30 depicts fold change in daptomycin MIC value as a function of days of serial passage under resistance selection conditions in the presence of daptomycin alone or daptomycin with sub-MIC amounts of PlySs2 lysin for multiple cultures (three independent cultures of each).
Figure 31:
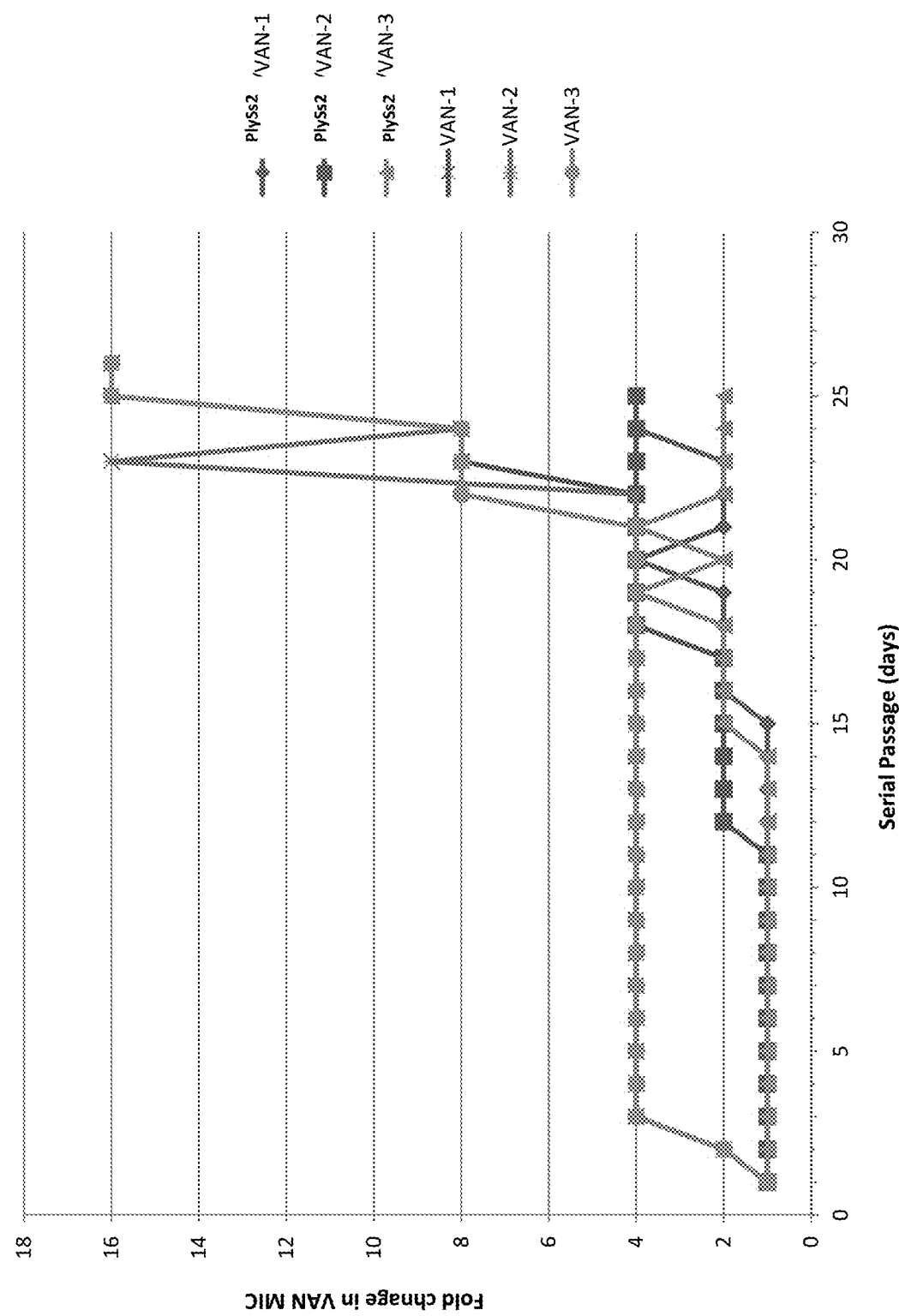
FIG. 31 depicts fold change in vancomycin MIC value as a function of days of serial passage under resistance selection conditions in the presence of daptomycin alone or daptomycin with sub-MIC amounts PlySs2 lysin for multiple cultures (three independent cultures of each).

For the daptomycin experiments, it was found that over the course of the 30-day study, daptomycin resistance increased significantly for all three daptomycin-only cultures (FIG. 30). In these cultures the daptomycin MIC values increased from the starting value of 1 ug/ml, to the three ending values of 128, 128 and 64 ug/ml—a 64 to 128-fold increase. For cultures that were passaged in the presence of sub-MIC amounts of PlySs2 (4 ug/ml) plus daptomycin, the daptomycin MIC values at the end of the 30 serial passage experiment were significantly lower −4, 4, and 4 ug/ml (a 4 fold increase). Therefore, sub-MIC concentrations of PlySs2 suppressed the ability of the MRSA strain to mount daptomycin resistance by 8 to 16 fold relative to the daptomycin alone conditions. Resistance to daptomycin increased by only about 4 fold in the presence of PlySs2 lysin.

For the vancomycin experiments, it was found that over the course of the 25-day study, vancomycin resistance increased significantly for all three vancomycin-only cultures. In these cultures the vancomycin MIC values increased from the starting value of 1 ug/ml, to the three ending values of 16, 16 and 16 ug/ml (a 16-fold increase). For cultures that were passaged in the presence of sub-MIC amounts of PlySs2 (8 ug/ml) plus vancomycin, the vancomycin MIC values at the end of the 25 day serial passage experiment were significantly lower −4, 4, and 2 ug/ml (a 2 to 4 fold increase). Therefore, sub-MIC concentrations of PlySs2 suppressed the ability of the MRSA strain to mount vancomycin resistance by 4 to 8 fold relative to the vancomycin alone conditions. Resistance to daptomycin increased by only about 4 fold in the presence of PlySs2 lysin.

REFERENCES

1. Klevens, R. M., et al. Invasive Methicillin-Resistant *Staphylococcus aureus* Infections in the United States. *JAMA* 298, 1763-1771 (2007).

2. Brink, A. J. Does resistance in severe infections caused by methicillin-resistant *Staphylococcus aureus* give you the 'creeps'? *Current opinion in critical care* 18, 451-459 (2012).
3. Ben-David, D., Novikov, I. & Mermel, L. A. Are there differences in hospital cost between patients with nosocomial methicillin-resistant *Staphylococcus aureus* bloodstream infection and those with methicillin-susceptible *S. aureus* bloodstream infection? *Infection control and hospital epidemiology: the official journal of the Society of Hospital Epidemiologists of America* 30, 453-460 (2009).
4. Fischetti, V. A. Bacteriophage lysins as effective antibacterials. *Current opinion in microbiology* 11, 393-400 (2008).
5. Fenton, M., Ross, P., McAuliffe, O., O'Mahony, J. & Coffey, A. Recombinant bacteriophage lysins as antibacterials. *Bioengineered Bugs* 1, 9-16 (2010).
6. Nelson, D., Loomis, L. & Fischetti, V. A. Prevention and elimination of upper respiratory colonization of mice by group A streptococci by using a bacteriophage lytic enzyme. *Proceedings of the National Academy of Sciences of the United States of America* 98, 4107-4112 (2001).
7. Witzenrath, M., et al. Systemic use of the endolysin Cpl-1 rescues mice with fatal pneumococcal pneumonia. *Critical care medicine* 37, 642-649 (2009).
8. McCullers, J. A., Karlstrom, A., Iverson, A. R., Loeffler, J. M. & Fischetti, V. A. Novel Strategy to Prevent Otitis Media Cauesed by Colonizing *Streptococcus pneumoniae*. *PLOS pathogens* 3, 0001-0003 (2007).
9. Pastagia, M., et al. A novel chimeric lysin shows superiority to mupirocin for skin decolonization of methicillin-resistant and -sensitive *Staphylococcus aureus* strains. *Antimicrobial agents and chemotherapy* 55, 738-744 (2011).
10. Loeffler, J. M., Djurkovic, S. & Fischetti, V. A. Phage Lytic Enzyme Cpl-1 as a Novel Antimicrobial for Pneumococcal Bacteremia. *Infection and Immunity* 71, 6199-6204 (2003).
11. Entenza, J. M., Loeffler, J. M., Grandgirard, D., Fischetti, V. A. & Moreillon, P. Therapeutic effects of bacteriophage Cpl-1 lysin against *Streptococcus pneumoniae* endocarditis in rats. *Antimicrobial agents and chemotherapy* 49, 4789-4792 (2005).
12. Grandgirard, D., Loeffler, J. M., Fischetti, V. A. & Leib, S. L. Phage lytic enzyme Cpl-1 for antibacterial therapy in experimental pneumococcal meningitis. *The Journal of infectious diseases* 197, 1519-1522 (2008).
13. Blaser, M. Stop killing beneficial bacteria. *Nature* 476, 393-394 (2011).
14. Willing, B. P., Russell, S. L. & Finlay, B. B. Shifting the balance: antibiotic effects on host-microbiota mutualism. *Nature reviews. Microbiology* 9, 233-243 (2011).
15. Gilmer, D. B., Schmitz, J. E., Euler, C. & Fischetti, V. A. Novel Bacteriophage Lysin with Broad Lytic Activity Protects against Mixed Infection by Methicillin-Resistant *Staphylococcus aureus* and *Streptococcus pyogenes TBD* (2012).
16. Schuch, R., Fischetti, V. A. & Nelson, D. C. A Genetic Screen to Identify Bacteriophage Lysins. in *Bacteriophages: Methods and Protocols, Volume 2: Molecular and Applied Aspects*, Vol. 502 307-319 (2009).
17. Bateman, A. & Rawlings, N. D. The CHAP domain: a large family of amidases including GSP amidase and peptidoglycan hydrolases. *Trends Biochem Sci* 28, 234-237 (2003).
18. Whisstock, J. C. & Lesk, A. M. SH3 domains in prokaryotes. *Trends in Biochemical Sciences* 24, 132-133 (1999).
19. Rossi, P., et al. Structural elucidation of the Cys-His-Glu-Asn proteolytic relay in the secreted CHAP domain enzyme from the human pathogen *Staphylococcus saprophyticus*. *Proteins* 74, 515-519 (2009).
20. Mueller, M., de la Pena, A. & Derendorf, H. Issues in Pharmacokinetics and Pharmacodynamics of Anti-Infective Agents: Kill Curves versus MIC. *Antimicrobial agents and chemotherapy* 48, 369-377 (2004).
21. Methods for dilution antimicrobial susceptibility tests for bacteria that grow aerobically. Vol. 32 (Wayne (Pa.): Clinical and Laboratory Standards Institute (US), 2012).
22. Friedman, L., Alder, J. D. & Silverman, J. A. Genetic changes that correlate with reduced susceptibility to daptomycin in *Staphylococcus aureus*. *Antimicrobial agents and chemotherapy* 50, 2137-2145 (2006).
23. Donlan, R. M. & Costerton, J. W. Biofilms: Survival Mechanisms of Clinically Relevant Microorganisms. *Clinical Microbiology Reviews* 15, 167-193 (2002).
24. Cottarel, G. & Wierzbowski, J. Combination drugs, an emerging option for antibacterial therapy. *Trends in biotechnology* 25, 547-555 (2007).
25. Tallarida, R. J. Revisiting the isobole and related quantitative methods for assessing drug synergism. *The Journal of pharmacology and experimental therapeutics* 342, 2-8 (2012).
26. LaPlante, K. L., Leonard, S. N., Andes, D. R., Craig, W. A. & Rybak, M. J. Activities of clindamycin, daptomycin, doxycycline, linezolid, trimethoprim-sulfamethoxazole, and vancomycin against community-associated methicillin-resistant *Staphylococcus aureus* with inducible clindamycin resistance in murine thigh infection and in vitro pharmacodynamic models. *Antimicrobial agents and chemotherapy* 52, 2156-2162 (2008).
27. Crandon, J. L., Kuti, J. L. & Nicolau, D. P. Comparative efficacies of human simulated exposures of telavancin and vancomycin against methicillin-resistant *Staphylococcus aureus* with a range of vancomycin MICs in a murine pneumonia model. *Antimicrobial agents and chemotherapy* 54, 5115-5119 (2010).
28. Abad, C. L., Kumar, A. & Safdar, N. Antimicrobial therapy of sepsis and septic shock—when are two drugs better than one? *Critical care clinics* 27, el-27 (2011).
29. Fischbach, M. A. Combination therapies for combating antimicrobial resistance. *Current opinion in microbiology* 14, 519-523 (2011).
30. Loeffler, J. M., Nelson, D. & Fischetti, V. A. Rapid killing of *Streptococcus pneumoniae* with a bacteriophage cell wall hydrolase. *Science* 294, 2170-2172 (2001).
31. Costerton, J. W. Bacterial Biofilms: A Common Cause of Persistent Infections. *Science* 284, 1318-1322 (1999).
32. Kiedrowski, M. R. & Horswill, A. R. New approaches for treating staphylococcal biofilm infections. *Annals of the New York Academy of Sciences* 1241, 104-121 (2011).
33. Domenech, M., Garcia, E. & Moscoso, M. In vitro destruction of *Streptococcus pneumoniae* biofilms with bacterial and phage peptidoglycan hydrolases. *Antimicrobial agents and chemotherapy* 55, 4144-4148 (2011).
34. Meng, X., et al. Application of a bacteriophage lysin to disrupt biofilms formed by the animal pathogen *Streptococcus suis*. *Applied and environmental microbiology* 77, 8272-8279 (2011).
35. Schuch, R., Nelson, D. & Fischetti, V. A bacteriolytic agent that detects and kills *Bacillus anthracis*. *Nature* 418, 884-889 (2002).

36. Fischetti, V. A., Nelson, D. & Schuch, R. Reinventing phage therapy: are the parts greater than the sum? *Nature Biotechnology* 24, 1508-1511 (2006).
37. Manoharadas, S., Witte, A. & Blasi, U. Antimicrobial activity of a chimeric enzybiotic towards *Staphylococcus aureus*. *Journal of biotechnology* 139, 118-123 (2009).
38. Rashel, M., et al. Efficient elimination of multidrug-resistant *Staphylococcus aureus* by cloned lysin derived from bacteriophage phi MR11. *The Journal of infectious diseases* 196, 1237-1247 (2007).
39. Daniel, A., et al. Synergism between a novel chimeric lysin and oxacillin protects against infection by methicillin-resistant *Staphylococcus aureus*. *Antimicrobial agents and chemotherapy* 54, 1603-1612 (2010).
40. Kokai-Kun, J. F., Chanturiya, T. & Mond, J. J. Lysostaphin as a treatment for systemic *Staphylococcus aureus* infection in a mouse model. *The Journal of antimicrobial chemotherapy* 60, 1051-1059 (2007).
41. Dhand, A., et al. Use of antistaphylococcal beta-lactams to increase daptomycin activity in eradicating persistent bacteremia due to methicillin-resistant *Staphylococcus aureus*: role of enhanced daptomycin binding. *Clinical infectious diseases: an official publication of the Infectious Diseases Society of America* 53, 158-163 (2011).
42. Matias, V. R. & Beveridge, T. J. Cryo-electron microscopy of cell division in *Staphylococcus aureus* reveals a mid-zone between nascent cross walls. *Molecular microbiology* 64, 195-206 (2007).
43. Kashyap, D. R., et al. Peptidoglycan recognition proteins kill bacteria by activating protein-sensing two-component systems. *Nature medicine* 17, 676-683 (2011).
44. Moise, P. A., North, D., Steenbergen, J. N. & Sakoulas, G. Susceptibility relationship between vancomycin and daptomycin in *Staphylococcus aureus*: facts and assumptions. *Lancet Infect Dis* 9, 617-624 (2009).
45. Jobson, S., Moise, P. A. & Eskandarian, R. Retrospective observational study comparing vancomycin versus daptomycin as initial therapy for *Staphylococcus aureus* infections. *Clinical therapeutics* 33, 1391-1399 (2011).
46. Schweizer, M. L., et al. Comparative effectiveness of nafcillin or cefazolin versus vancomycin in methicillin-susceptible *Staphylococcus aureus* bacteremia. *BMC infectious diseases* 11, 279 (2011).
47. Bern, A. D., et al. Altering the proclivity towards daptomycin resistance in methicillin-resistant *Staphylococcus aureus* using combinations with other antibiotics. *Antimicrobial agents and chemotherapy* 56, 5046-5053 (2012).
48. Sopirala, M. M., et al. Synergy testing by Etest, microdilution checkerboard, and time-kill methods for pan-drug-resistant Acinetobacter baumannii. *Antimicrobial agents and chemotherapy* 54, 4678-4683 (2010).
49. Methods for dilution antimicrobial susceptibility tests for bacteria that grow aerobically. Vol. 32 (Clinical and Laboratory Standards Institute (US), Wayne (Pa.), 2012).
50. *Clinical Microbiology Procedures Handbook 3rd Ed.* Washington D.C., (ASM Press, 2010).
51. Pereira, P. M., Filipe, S. R., Tomasz, A. & Pinho, M. G. Fluorescence ratio imaging microscopy shows decreased access of vancomycin to cell wall synthetic sites in vancomycin-resistant *Staphylococcus aureus*. *Antimicrobial agents and chemotherapy* 51, 3627-3633 (2007).
52. Zhang, Y. I-TASSER server for protein 3D structure prediction. *BMC bioinformatics* 9, 40 (2008).
53. Pettersen, E. F., et al. UCSF Chimera—a visualization system for exploratory research and analysis. *Journal of computational chemistry* 25, 1605-1612 (2004).

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

---

What is claimed is:

1. A method of reducing the development of antibiotic resistance to *Staphylococcus* or *Streptococcus* bacteria in a human comprising:
   administering to the human:
   i) a Gram-positive antibiotic selected from:
      vancomycin or a glycopeptide antibiotic of the same class;
      daptomycin or a lipopeptide antibiotic of the same class; and
      oxacillin or a beta lactam penicillin antibiotic of the same class; and
   ii) a lysin effective to kill *Staphylococcus* and/or *Streptococcus* bacteria,
      wherein the lysin comprises the amino acid sequence provided in SEQ ID NO: 1 or a variant thereof having at least 90% identity to the polypeptide of SEQ ID NO: 1 and effective to kill *Staphylococcus* and/or *Streptococcus* bacteria, and
      wherein the lysin is administered at a dose at or below the minimal inhibitory concentration (MIC) dose.

2. The method of claim 1, wherein both the antibiotic and the lysin are administered at a dose below the minimal inhibitory concentration (MIC) dose.

3. The method of claim 1 wherein the antibiotic is administered at a dose below the minimal inhibitory concentration (MIC).

4. The method of claim 1 wherein the lysin comprises the amino acid sequence provided in SEQ ID NO: 1 or variants thereof having at least 95% identity to the polypeptide of SEQ ID NO: 1 and effective to kill *Staphylococcus* and *Streptococcus* bacteria.

5. The method of claim 1 wherein the *Staphylococcus* bacteria is *Staphylococcus aureus*.

6. The method of claim 1 wherein the antibiotic is selected from vancomycin, oxacillin and daptomycin.

7. The method of claim 1 wherein the lysin is administered at a dose below the minimal inhibitory concentration (MIC) dose.

8. The method of claim 1 wherein the *Staphylococcus* bacteria is methicillin-resistant *Staphylococcus aureus*.

* * * * *

UNITED STATES PATENT AND TRADEMARK OFFICE
CERTIFICATE OF CORRECTION

PATENT NO. : 10,813,983 B2  
APPLICATION NO. : 14/399575  
DATED : October 27, 2020  
INVENTOR(S) : Raymond Schuch et al.

Page 1 of 1

It is certified that error appears in the above-identified patent and that said Letters Patent is hereby corrected as shown below:

On the Title Page

(72) Inventors: "Han Lee, Yonkers, NY (US)" should read -- Han Lee, Gaithersburg, MD (US) --; and

(72) Inventors: "Brent Schneider, Glenmoore, PA (US)" should read -- Brent Schneider, Warminster, PA (US) --

Signed and Sealed this
Eighth Day of December, 2020

Andrei Iancu
*Director of the United States Patent and Trademark Office*

SEQUENCE LISTING

```
<160> NUMBER OF SEQ ID NOS: 5

<210> SEQ ID NO 1
<211> LENGTH: 245
<212> TYPE: PRT
<213> ORGANISM: Streptococcus suis

<400> SEQUENCE: 1

Met Thr Thr Val Asn Glu Ala Leu Asn Asn Val Arg Ala Gln Val Gly
1               5                   10                  15

Ser Gly Val Ser Val Gly Asn Gly Glu Cys Tyr Ala Leu Ala Ser Trp
            20                  25                  30

Tyr Glu Arg Met Ile Ser Pro Asp Ala Thr Val Gly Leu Gly Ala Gly
        35                  40                  45

Val Gly Trp Val Ser Gly Ala Ile Gly Asp Thr Ile Ser Ala Lys Asn
    50                  55                  60

Ile Gly Ser Ser Tyr Asn Trp Gln Ala Asn Gly Trp Thr Val Ser Thr
65                  70                  75                  80

Ser Gly Pro Phe Lys Ala Gly Gln Ile Val Thr Leu Gly Ala Thr Pro
                85                  90                  95

Gly Asn Pro Tyr Gly His Val Val Ile Val Glu Ala Val Asp Gly Asp
```

```
                   100                 105                 110
Arg Leu Thr Ile Leu Glu Gln Asn Tyr Gly Gly Lys Arg Tyr Pro Val
            115                 120                 125

Arg Asn Tyr Tyr Ser Ala Ala Ser Tyr Arg Gln Gln Val Val His Tyr
        130                 135                 140

Ile Thr Pro Pro Gly Thr Val Ala Gln Ser Ala Pro Asn Leu Ala Gly
145                 150                 155                 160

Ser Arg Ser Tyr Arg Glu Thr Gly Thr Met Thr Val Thr Val Asp Ala
                165                 170                 175

Leu Asn Val Arg Arg Ala Pro Asn Thr Ser Gly Glu Ile Val Ala Val
            180                 185                 190

Tyr Lys Arg Gly Glu Ser Phe Asp Tyr Asp Thr Val Ile Ile Asp Val
        195                 200                 205

Asn Gly Tyr Val Trp Val Ser Tyr Ile Gly Gly Ser Gly Lys Arg Asn
210                 215                 220

Tyr Val Ala Thr Gly Ala Thr Lys Asp Gly Lys Arg Phe Gly Asn Ala
225                 230                 235                 240

Trp Gly Thr Phe Lys
            245

<210> SEQ ID NO 2
<211> LENGTH: 738
<212> TYPE: DNA
<213> ORGANISM: Streptococcus suis

<400> SEQUENCE: 2
atgacaacag taaatgaagc attaaataat gtaagagctc aggttgggtc cggtgtgtct      60
gttggcaacg gcgaatgcta cgctttggct agttggtacg agcgcatgat tagtccggat     120
gcaactgtcg gacttggcgc tggtgtgggc tgggtcagcg gtgcaatcgg cgatacaatc     180
tctgccaaaa acatcggctc atcatacaac tggcaagcta acggctggac agtttccaca     240
tctggtccat ttaaagcagg tcagattgtg acgcttgggg caacaccagg aaacccttac     300
ggacatgtgg taatcgtcga agcagtggac ggcgatagat tgactatttt ggagcaaaac     360
tacggcggga aacgttatcc cgtccgtaat tattacagcg ctgcaagcta tcgtcaacag     420
gtcgtgcatt acatcacacc gcctggcacg gtcgcacagt cagcacccaa ccttgcaggc     480
tctcgttcct atcgcgagac gggcactatg actgtcacgg tcgatgctct caatgttcgc     540
agggcgccaa atacttcagg cgagattgta gcagtataca agcgtggtga atcatttgac     600
tatgatactg tcatcatcga tgtcaatggc tatgtctggg tgtcttacat aggcggcagc     660
ggcaaacgta actacgttgc gacgggcgct accaaagacg gtaagcgttt cggcaatgct     720
tggggtacat ttaaataa                                                   738

<210> SEQ ID NO 3
<211> LENGTH: 139
<212> TYPE: PRT
<213> ORGANISM: Streptococcus suis

<400> SEQUENCE: 3

Leu Asn Asn Val Arg Ala Gln Val Gly Ser Gly Val Ser Val Gly Asn
1               5                   10                  15

Gly Glu Cys Tyr Ala Leu Ala Ser Trp Tyr Glu Arg Met Ile Ser Pro
            20                  25                  30

Asp Ala Thr Val Gly Leu Gly Ala Gly Val Gly Trp Val Ser Gly Ala
        35                  40                  45
```

```
Ile Gly Asp Thr Ile Ser Ala Lys Asn Ile Gly Ser Ser Tyr Asn Trp
        50                  55                  60

Gln Ala Asn Gly Trp Thr Val Ser Thr Ser Gly Pro Phe Lys Ala Gly
 65                  70                  75                  80

Gln Ile Val Thr Leu Gly Ala Thr Pro Gly Asn Pro Tyr Gly His Val
                85                  90                  95

Val Ile Val Glu Ala Val Asp Gly Asp Arg Leu Thr Ile Leu Glu Gln
            100                 105                 110

Asn Tyr Gly Gly Lys Arg Tyr Pro Val Arg Asn Tyr Ser Ala Ala
            115                 120                 125

Ser Tyr Arg Gln Gln Val Val His Tyr Ile Thr
            130                 135

<210> SEQ ID NO 4
<211> LENGTH: 67
<212> TYPE: PRT
<213> ORGANISM: Streptococcus suis

<400> SEQUENCE: 4

Arg Ser Tyr Arg Glu Thr Gly Thr Met Thr Val Thr Val Asp Ala Leu
 1               5                  10                  15

Asn Val Arg Arg Ala Pro Asn Thr Ser Gly Glu Ile Val Ala Val Tyr
            20                  25                  30

Lys Arg Gly Glu Ser Phe Asp Tyr Asp Thr Val Ile Ile Asp Val Asn
        35                  40                  45

Gly Tyr Val Trp Val Ser Tyr Ile Gly Gly Ser Gly Lys Arg Asn Tyr
    50                  55                  60

Val Ala Thr
 65

<210> SEQ ID NO 5
<211> LENGTH: 280
<212> TYPE: PRT
<213> ORGANISM: Staphylococcus aureus

<400> SEQUENCE: 5

Met Glu Thr Leu Lys Gln Ala Glu Ser Tyr Ile Lys Ser Lys Val Asn
 1               5                  10                  15

Thr Gly Thr Asp Phe Asp Gly Leu Tyr Gly Tyr Gln Cys Met Asp Leu
            20                  25                  30

Ala Val Asp Tyr Ile Tyr His Val Thr Asp Gly Lys Ile Arg Met Trp
        35                  40                  45

Gly Asn Ala Lys Asp Ala Ile Asn Asn Ser Phe Gly Gly Thr Ala Thr
    50                  55                  60

Val Tyr Lys Asn Tyr Pro Ala Phe Arg Pro Lys Tyr Gly Asp Val Val
 65                  70                  75                  80

Val Trp Thr Thr Gly Asn Phe Ala Thr Tyr Gly His Ile Ala Ile Val
                85                  90                  95

Thr Asn Pro Asp Pro Tyr Gly Asp Leu Gln Tyr Val Thr Val Leu Glu
            100                 105                 110

Gln Asn Trp Asn Gly Asn Gly Ile Tyr Lys Thr Glu Leu Ala Thr Ile
            115                 120                 125

Arg Thr His Asp Tyr Thr Gly Ile Thr His Phe Ile Arg Pro Asn Phe
        130                 135                 140

Ala Thr Glu Ser Ser Val Lys Lys Lys Asp Thr Lys Lys Lys Pro Lys
145                 150                 155                 160
```

```
Pro Ser Asn Arg Asp Gly Leu Asn Lys Asp Lys Ile Val Tyr Asp Arg
            165                 170                 175

Thr Asn Ile Asn Tyr Asn Met Val Leu Gln Gly Lys Ser Ala Ser Lys
            180                 185                 190

Ile Thr Val Gly Ser Lys Ala Pro Tyr Asn Leu Lys Trp Ser Lys Gly
        195                 200                 205

Ala Tyr Phe Asn Ala Lys Ile Asp Gly Leu Gly Ala Thr Ser Ala Thr
        210                 215                 220

Arg Tyr Gly Asp Asn Arg Thr Asn Tyr Arg Phe Asp Val Gly Gln Ala
225                 230                 235                 240

Val Tyr Ala Pro Gly Thr Leu Ile Tyr Val Phe Glu Ile Ile Asp Gly
            245                 250                 255

Trp Cys Arg Ile Tyr Trp Asn Asn His Asn Glu Trp Ile Trp His Glu
            260                 265                 270

Arg Leu Ile Val Lys Glu Val Phe
            275             280
```